(12) United States Patent
Zeng et al.

(10) Patent No.: US 9,493,435 B2
(45) Date of Patent: Nov. 15, 2016

(54) IRE-1α INHIBITORS

(75) Inventors: Qingping Zeng, Thousand Oaks, CA (US); Warren S. Wade, San Diego, CA (US); John Bruce Patterson, Ventura, CA (US)

(73) Assignee: MannKing Corporation, Valencia, CA (US)

( * ) Notice: Subject to any disclaimer, the term of this patent is extended or adjusted under 35 U.S.C. 154(b) by 348 days.

(21) Appl. No.: 13/505,530

(22) PCT Filed: Nov. 1, 2010

(86) PCT No.: PCT/US2010/054940
§ 371 (c)(1),
(2), (4) Date: Jul. 12, 2012

(87) PCT Pub. No.: WO2011/056744
PCT Pub. Date: May 12, 2011

(65) Prior Publication Data
US 2012/0270877 A1    Oct. 25, 2012

Related U.S. Application Data

(60) Provisional application No. 61/257,696, filed on Nov. 3, 2009.

(51) Int. Cl.
| | | |
|---|---|---|
| *C07D 295/192* | (2006.01) |
| *C07D 413/06* | (2006.01) |
| *C07D 417/06* | (2006.01) |
| *C07D 417/04* | (2006.01) |
| *C07D 403/04* | (2006.01) |
| *C07D 405/06* | (2006.01) |
| *C07D 295/112* | (2006.01) |
| *C07D 277/56* | (2006.01) |
| *C07D 417/12* | (2006.01) |
| *C07D 239/38* | (2006.01) |
| *C07D 249/06* | (2006.01) |
| *C07C 235/78* | (2006.01) |
| *C07D 207/16* | (2006.01) |
| *C07D 307/68* | (2006.01) |
| *C07D 239/26* | (2006.01) |
| *C07C 59/74* | (2006.01) |
| *C07C 65/30* | (2006.01) |
| *C07C 69/738* | (2006.01) |
| *C07C 235/84* | (2006.01) |
| *C07D 211/62* | (2006.01) |
| *C07D 211/66* | (2006.01) |
| *C07D 211/98* | (2006.01) |
| *C07D 213/36* | (2006.01) |
| *C07D 213/74* | (2006.01) |
| *C07D 213/81* | (2006.01) |
| *C07D 213/82* | (2006.01) |

(Continued)

(52) U.S. Cl.
CPC .......... *C07D 295/192* (2013.01); *C07C 235/78* (2013.01); *C07D 207/16* (2013.01); *C07D 239/26* (2013.01); *C07D 239/38* (2013.01); *C07D 249/06* (2013.01); *C07D 277/56* (2013.01); *C07D 295/112* (2013.01); *C07D 307/68* (2013.01); *C07D 403/04* (2013.01); *C07D 405/06* (2013.01); *C07D 413/06* (2013.01); *C07D 417/04* (2013.01); *C07D 417/06* (2013.01); *C07D 417/12* (2013.01); C07C 59/74 (2013.01); C07C 65/30 (2013.01); C07C 69/738 (2013.01); C07C 235/84 (2013.01); *C07D 211/62* (2013.01); *C07D 211/66* (2013.01); *C07D 211/98* (2013.01); *C07D 213/36* (2013.01); *C07D 213/74* (2013.01); *C07D 213/81* (2013.01); *C07D 213/82* (2013.01); *C07D 263/34* (2013.01); *C07D 277/42* (2013.01); *C07D 295/185* (2013.01); *C07D 333/38* (2013.01); *C07D 333/40* (2013.01); *C07D 401/12* (2013.01); *C07D 405/12* (2013.01); *C07D 409/12* (2013.01); *C07D 487/08* (2013.01)

(58) Field of Classification Search
CPC ............ C07D 295/192; C07D 413/06; C07D 417/06; C07D 417/04; C07D 403/04; C07D 405/06; C07D 295/112; C07D 277/56; C07D 417/12; C07D 239/38; C07D 249/06; C07D 207/16; C07D 307/68; C07D 239/26; C07C 235/78
See application file for complete search history.

(56) References Cited

U.S. PATENT DOCUMENTS

| | | |
|---|---|---|
| 3,053,831 A | 9/1962 | Childress |
| 3,859,350 A | 1/1975 | Sahm et al. |

(Continued)

FOREIGN PATENT DOCUMENTS

| | | |
|---|---|---|
| WO | WO 2007/101224 A2 | 9/2007 |
| WO | WO 2008154484 A1 * | 12/2008 |

(Continued)

OTHER PUBLICATIONS

Morgan et al. Journal of the Chemical Society, Transactions, 1921, 119, 177-187.*

(Continued)

*Primary Examiner* — Matthew Coughlin
(74) *Attorney, Agent, or Firm* — Banner & Witcoff, Ltd.

(57) ABSTRACT

The invention provides compounds which directly inhibit IRE-1α activity in vitro, prodrugs, and pharmaceutically acceptable salts thereof. Such compounds and prodrugs are useful for treating diseases associated with the unfolded protein response and can be used as single agents or in combination therapies.

17 Claims, 1 Drawing Sheet

(51) Int. Cl.

| | |
|---|---|
| C07D 263/34 | (2006.01) |
| C07D 277/42 | (2006.01) |
| C07D 295/185 | (2006.01) |
| C07D 333/38 | (2006.01) |
| C07D 333/40 | (2006.01) |
| C07D 401/12 | (2006.01) |
| C07D 405/12 | (2006.01) |
| C07D 409/12 | (2006.01) |
| C07D 487/08 | (2006.01) |

(56) References Cited

U.S. PATENT DOCUMENTS

| | | | |
|---|---|---|---|
| 6,313,160 | B1 | 11/2001 | Guillaumet |
| 7,858,666 | B2 * | 12/2010 | Patterson et al. ............. 514/700 |
| 8,614,253 | B2 * | 12/2013 | Patterson et al. ............. 514/700 |
| 2009/0186893 | A1 | 7/2009 | Patterson et al. |
| 2011/0319436 | A1 | 12/2011 | Walter et al. |

FOREIGN PATENT DOCUMENTS

| | | |
|---|---|---|
| WO | WO 2010/031056 A2 | 3/2010 |
| WO | WO 2011/047384 A2 | 4/2011 |

OTHER PUBLICATIONS

CAS Registry No. 92262-76-5, which entered STN on Nov. 16th, 1984.*
Sheridan, R.P. J. Chem. Inf. Comput. Sci. 2002, 42, 103-108.*
International Search Report mailed Mar. 24, 2011 for PCT/US10/054940.
Extended European Search Report mailed Apr. 4, 2013 for Serial No. 10828948.9.
Adams et al., "Restricted Rotation in Aryl Olefins. VI. Substituted β-(2,7-Dimethoxy-1-naph-thyl)-α-methylacrylic Acids," Journal of the American Chemical Society, vol. 64, No. 8, Aug. 1, 1942, pp. 1795-1801.
Brooke et al., "Reactions of polyfluoro-arenols and -heteroarenols with activated dimethyl sulphoxide. Facile [2,3]-sigmatropic rearangement reactions giving de-aromatised products," Journal of the Chemical Society, Jan. 1, 1987, pp. 2091-2097.
Yoo et al., "Three naphthalenes from root bark of *Hibiscus syriacus*," Phytochemistry, vol. 47, No. 5, Mar. 1, 1998, pp. 799-802.
Pittelkow et al., "Carbocations in Action. Design, Synthesis, and Evaluation of a Highly Acid-Sensitive Naphthalene-Based Backbone Amide Linker for Solid-Phase Synthesis," Organic Letters, vol. 8, No. 25, Dec. 1, 2006, pp. 5817-5820.
Prudent et al., "Salicylaldehyde derivatives as new protein kinase CK2 inhibitors," Biochimica et Biophysica Acta, vol. 1780, No. 12, Dec. 1, 2008, pp. 1412-1420.
Sankaram et al., "New sesquiterpenoids of *Bombax malabaricum*," Phytochemistry, vol. 20, No. 8, Jan. 1, 1981, pp. 1877-1881.
Buisson & Royer, "Synthèse et essais exploratoires contre les bactéries et les protozoaires de dérivés polyméthoxylés du nitro-2 naphto[2,1-b]furanne," European Journal of Medicinal Chemistry, vol. 19, No. 3, p. 249-253 (1984), English abstract and compounds.
Carey & Thomson, "New Routes to Phenalenones from 2,7-Dihydroxynaphthalene. X-Ray Crystal Structure of 4-(a-Hydroxybenzyl)-2-phenyl-6H-phenaleno-{1,9-bc]pyran-6-one," Journal of the Chemical Society, Perkin Transactions I, No. 6, p. 1267-1274 (1983).
Chatterjea et al., "Studies on Furano Compounds: Part XLVIII-Syntheses of 2,5-Dimethyl- & 2-Ehtyl-5-methylnaphtho [2,r-b]furans," Indian Journal of Chemistry, Section B, vol. 20B, No. 4, p. 264-267 (1981).
Choubal et al., "The Action of Hexamethylenetetramine of Phenols and the Methyl Esters of Phenolcarboxylic Acids Part VI. The Synthesis and Study of the Arylamides of x-Formyl-2-Hydroxy-3-Naphthoic Acid," Journal of the Indian Chemical Society, vol. 35, No. 12, p. 860-864 (1958).
Chu et al., "Synthesis and Pharmacological Analysis of High Affinity Melatonin Receptor Ligands," Chemical & Pharmaceutical Bulletin, vol. 50, No. 2, p. 272-275 (2002).
Einhorn et al., Synthèse et activités contre les microorganismes d'acides carboxyliques dérivés du nitro-2 naphto[2,1-b]furanne, European Journal of Medicinal Chemistry, vol. 19, No. 2, p. 143-147 (1984), English abstract and compounds.
Haraldsson & Baldwin, "A Selective Cleavage of Aromatic Benzyl Ethers Located Ortho to a Carbonyl Group by Magnesium Bromide," Tetrahedron, vol. 53, No. 1, p. 215-224 (1997).

* cited by examiner

FIG. 1B Liver
FIG. 1C Kidney

IRE-1α INHIBITORS

This application incorporates by reference the contents of an 883 byte text file created on Apr. 26, 2012 and named "sequencelisting.txt," which is the sequence listing for this application.

This application claims the benefit of and incorporates by reference Ser. No. 61/257,696 filed Nov. 3, 2009.

FIELD OF THE INVENTION

The invention relates to IRE-1α inhibitors and their therapeutic uses.

BACKGROUND OF THE INVENTION

Protein folding stress in the endoplasmic reticulum of a cell initiates a signal transduction cascade termed the unfolded protein response or UPR. A key enzyme, inositol requiring enzyme 1 (IRE-1α), relieves protein folding stress by enhancing molecular chaperone activity and therefore protects cells from stress induced apoptosis. Inhibitors of IRE-1α are useful for treating at least B cell autoimmune diseases, certain cancers, and some viral infections.

BRIEF DESCRIPTION OF THE DRAWINGS

FIG. 1B and FIG. 1C are reverse images of RT-PCR products separated on 4% agarose gels, which demonstrate dose-dependent inhibition of XBP-1 splicing by compound 12-4 (CN-4) in liver (FIG. 1B) and kidney (FIG. 1C). See Example 29.

DETAILED DESCRIPTION OF THE INVENTION

Figure 1A:
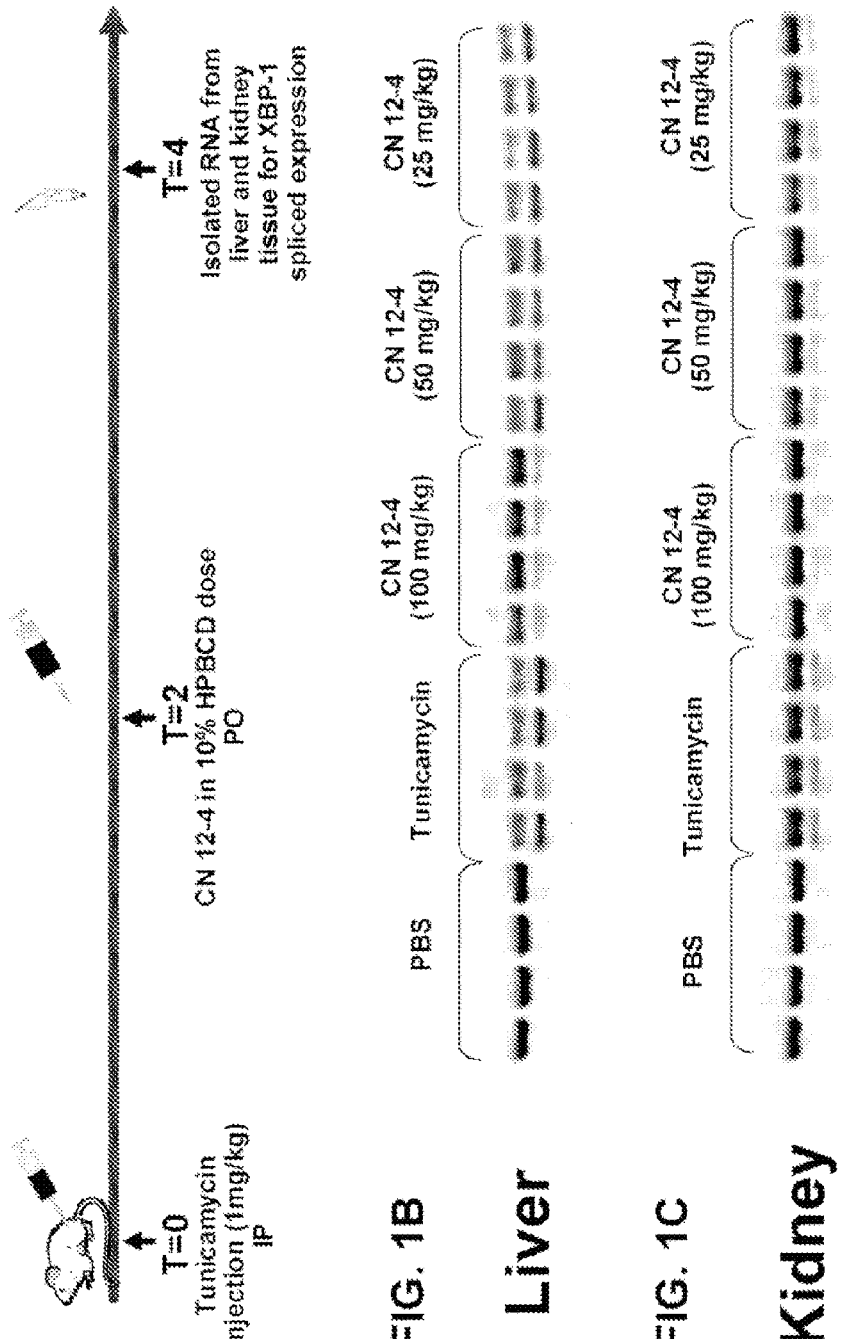
FIG. 1A is a schematic diagram of the experiment described in Example 29.

The invention provides IRE-1α inhibitor compounds and prodrugs and pharmaceutically acceptable salts thereof. The invention also provides pharmaceutical compositions and methods of using the IRE-1α inhibitor compounds, prodrugs, and pharmaceutically acceptable salts thereof therapeutically to treat disorders associated with the unfolded protein response. Patients who can be treated include those with B cell autoimmune diseases, certain cancers, and some viral infections.

IRE-1α Inhibitor Compounds

IRE-1α inhibitor compounds of the invention directly inhibit IRE-1α. The compounds are understood to act through inhibition of the RNAse activity of enzyme. In particular embodiments of the invention this activity is detected as cleavage of a human mini-XBP-1 mRNA stemloop substrate 5'-CAGUCCGCAGGACUG-3' (SEQ ID NO:1) by IRE-1α in vitro by 10 to 100%. Other substrates also can be used to detect cleavage. See US 2007/0105123.

IRE-1α inhibitor compounds of the invention can meet either or both of the following criteria:

a. Some compounds of the invention inhibit IRE-1α in the in vitro assay with an $IC_{50}$ of approximately 0.0005-20 μM. Some of these compounds have an $IC_{50}$ in this assay of approximately 1-20 μM. Others have an $IC_{50}$ in this assay of approximately 0.1-1 μM. Still others have an $IC_{50}$ of approximately 0.0005-0.1 μm.

b. Some compounds of the invention inhibit IRE-1α in an in vivo XBP-1 splicing assay (e.g., in myeloma cells) with an $EC_{50}$ in the range of approximately 0.05-80 μM. Some of these compounds have an $EC0_{50}$ in this assay of approximately 10-80 μM. Others have an $EC0_{50}$ in this assay of approximately 1-10 μM. Still others have an $EC0_{50}$ in this assay of approximately 0.05-1 μM.

DEFINITIONS

The following terms are used in this specification.

"Halogen" includes fluorine, chlorine, bromine, and iodine.

Unless otherwise specified, the term "alkyl" as used herein means a saturated monovalent hydrocarbon radical having 1, 2, 3, 4, 5, or 6 carbon atoms ("C1-C6 alkyl") and can be linear, branched, or a combination thereof. "C1-C6 alkyl" includes C1-C5 alkyl, C1-C4 alkyl, and C1-C3 alkyl. Examples of C1-C6 alkyls include methyl, ethyl, propyl, isopropyl, sec-butyl, tert-butyl, n-butyl, 2-butyl, pentyl, and hexyl.

"Alkoxy" as used herein means —O-alkyl groups, where "alkyl" is as defined above, and can be linear, branched, or a combination thereof. Examples of C1-C6 alkoxys include, for example, methoxy, ethoxy, propoxy, 2-propoxy, butoxy, sec-butoxy, and tert-butoxy.

The term "perfluoroalkyl" means an alkyl group as defined above in which all of the hydrogen atoms are replaced by fluorine atoms. The term "perfluoroalkoxy" means an alkoxy group in which the alkyl moiety is a perfluoroalkyl group as defined above.

The term "hydroxylalkyl" as used herein means an alkyl group as defined above which is substituted with a hydroxyl group.

The term "alkoxylalkyl" means radicals of the formula $C_aH_{2a+1}$—O—$(CH_2)_b$—, in which a and b independently are 1, 2, 3, 4, 5, or 6.

A "cycloalkyl" is a saturated or partially saturated 3- to 14-membered (i.e., a 3-, 4-, 5-, 6, 7-, 8-, 9-, 10-, 11-, 12-, 13-, or 14-membered) monocyclic or polycyclic ring, such as a 5-, 6-, or 7-membered monocyclic ring or a 10-membered bicyclic ring, in which all of the ring members are carbon atoms. Examples of cycloalkyls include cyclobutyl, cyclopentyl, cyclohexyl, cycloheptyl, and cyclooctyl.

"Aryl," when used alone or as part of another term, means a carbocyclic aromatic ring containing 5 to 14 members (e.g., 5, 6, 7, 8, 9, 10, 11, 12, 13, or 14 members) and can be monocyclic or polycyclic. Examples of aryls include phenyl, naphthyl, anthryl, and phenanthryl.

A "heterocycle," "heterocyclic group," and "heterocyclic ring" is a saturated or a partially saturated 4- to 14-membered (i.e., 4-, 5-, 6-, 7-, 8-, 9-, 10-, 11-, 12-, 13-, or 14-membered) monocyclic or polycyclic (fused) ring, such as a 5-, 6-, or 7-membered monocyclic ring or a 10-membered bicyclic ring which has 1, 2, 3, or 4 heteroatoms selected from nitrogen (N), oxygen (O), and sulfur (S). Any of the nitrogen and sulfur heteroatoms optionally can be oxidized, and any nitrogen heteroatom optionally can be quaternized. A heterocyclic ring can be attached at any suitable heteroatom or carbon atom. Examples of heterocycles include azepinyl, furyl, thienyl, pyrrolyl, pyrazolyl, imidazolyl, pyridyl, pyrazinyl, pyrimidinyl, pyridazinyl, triazolyl, isobenzofuranyl, furazanyl, indolyl, quinolinyl, oxazolyl, imidazolinyl, isoxazolyl, quinolyl, naphthyridinyl, phenoxazinyl, phenanthridinyl, chromenyl, triazinyl, purinyl, benzothienyl, benzimidazolyl, benzopyranyl, benzothiazolyl, benzoazolyl, benzo[b]thienyl, naphtho[2,3-b]-thienyl, isothiazolyl, thiazolyl, isothiazolyl, isoquinolinyl, thiadiazolyl, oxadiazolyl, tetrahydroquinolinyl, indolizinyl, isoindolyl, indazolyl, isoquinolyl, phthalazinyl, tetrahydroquinolinyl, and cinnolinyl.

A "heteroaryl" is a saturated 4- to 14-membered (i.e., 4-, 5-, 6-, 7-, 8-, 9-, 10-, 11-, 12-, 13-, or 14-membered) monocyclic or polycyclic (fused) ring, such as a 5-, 6-, or 7-membered monocyclic ring or a 10-membered bicyclic ring which has 1, 2, 3, or 4 heteroatoms selected from nitrogen (N), oxygen (O), and sulfur (S). Any of the nitrogen and sulfur heteroatoms optionally can be oxidized, and any nitrogen heteroatom optionally can be quaternized. A heteroaryl can be attached at any suitable heteroatom or carbon atom. Examples of heteroaryls include pyridyl, imidazolyl, pyrrolyl, thienyl, furyl, pyranyl, pyrimidinyl, pyridazinyl, indolyl, quinolyl, naphthyridinyl, and isoxazolyl.

Compounds

Compounds of the invention fall into one or more of the structural formulae described below. Non-limiting examples of compounds falling within the scope of these formulae are provided in Table 1 and in the Examples.

Some embodiments of the invention include only compounds which have structural formula (1):

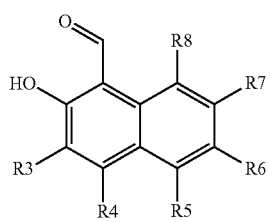

(1)

which encompasses formula (1a), (1b), (1c), and (1d), in which:

in formula (1a):
R3, R4, and R8 independently are hydrogen, halogen, perfluoroalkyl, —CN, —CONH$_2$, —CON(CH$_3$)$_2$, alkyl, perfluoroalkoxy, alkoxy, hydroxylalkyl, or alkoxylalkyl;
R5 is hydrogen or R7;
R6 is hydrogen, halogen, perfluoroalkyl, perfluoroalkoxy, —CN, alkyl, alkoxy, hydroxylalkyl, or alkoxylalkyl;
R7 is halogen; —CN; —CONH$_2$; —CON(CH$_3$)$_2$; alkyl; perfluoroalkyl; alkoxy; hydroxylalkyl; alkoxylalkyl; perfluoroalkoxyl;

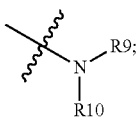

phenyl, optionally substituted with 1, 2, or 3 substituents independently selected from the group consisting of halogen, —CN, alkyl, perfluoroalkyl, alkoxy, hydroxylalkyl, alkoxylalkyl, perfluoroalkoxyl,

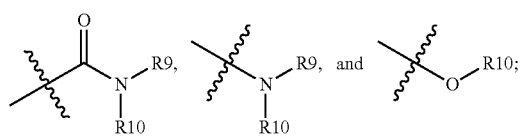

a 5- or 6-membered heteroaryl that is substituted with 1, 2, or 3 substituents independently selected from the group consisting of halogen, —CN, alkyl, perfluoroalkyl, alkoxy, hydroxylalkyl, alkoxylalkyl, perfluoroalkoxyl,

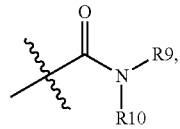

amino,

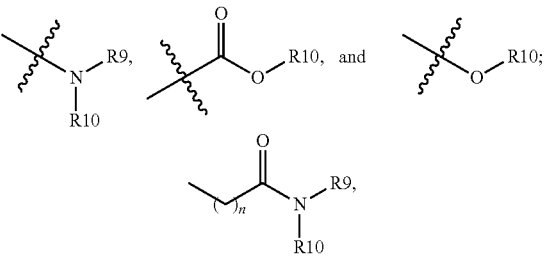

wherein n is 0, 1, or 2;

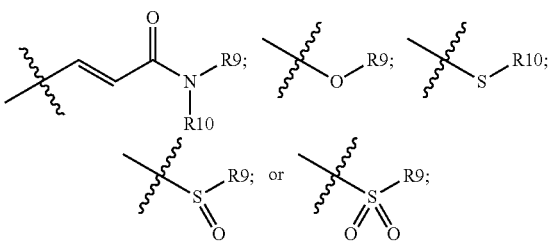

R9 is alkyl; alkoxylalkyl; perfluoroalkoxylalkyl; aryl, optionally substituted with 1, 2, or 3 substituents independently selected from the group consisting of halogen, perfluoroalkyl, perfluoroalkoxy, —CN, —CONH$_2$, —CON(CH$_3$)$_2$, alkyl, alkoxy, hydroxylalkyl, and alkoxylalkyl; a 5- or 6-membered heterocycle, optionally substituted with 1, 2, or 3 substituents independently selected from the group consisting of halogen, perfluoroalkyl, perfluoroalkoxy, —CN, —CONH$_2$, —CON(CH$_3$)$_2$, alkyl, alkoxy, hydroxylalkyl, and alkoxylalkyl; a 5- or 6-membered heteroaryl, optionally substituted with 1, 2, or 3 substituents independently selected from the group consisting of halogen, perfluoroalkyl, perfluoroalkoxy, —CN, —CONH$_2$, —CON(CH$_3$)$_2$, alkyl, alkoxy, hydroxylalkyl, and alkoxylalkyl; or

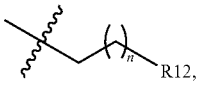

wherein n is 0, 1, 2, or 3; and R10 is hydrogen or R9; or
R9 and R10, together with the nitrogen atom to which they are attached, form a heterocycle containing 1, 2, 3, or 4 heteroatoms selected from N, O and S, optionally substituted with 1, 2, or 3 substituents selected independently from R11;

R11 is hydrogen; alkyl; aryl; heteroaryl containing 1 or 2 heteroatoms selected from N, O, and S; arylalkyl; heteroarylalkyl in which the heteroaryl contains 1 or 2 heteroatoms selected from N, O, and S;

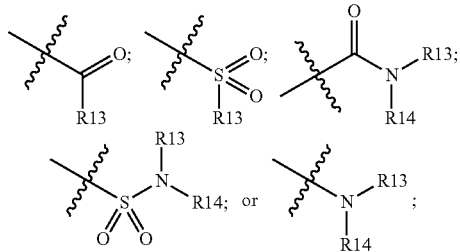

R12 is amino; alkoxy; aryl, optionally substituted with 1, 2, or 3 substitutents selected independently from R11; a 5- or 6-membered heterocycle having 1, 2, or 3 heteroatoms selected from N, O, and S and optionally substituted with 1, 2, or 3 substitutents selected independently from R11; or a 5- or 6-membered heteroaryl having 1, 2, or 3 heteroatoms selected from N, O, and S and optionally substituted with 1, 2, or 3 substitutents selected independently from R11;

R13 is alkyl; alkoxylalkyl; perfluoroalkoxylalkyl; aryl, optionally substituted with 1, 2, or 3 substituents independently selected from the group consisting of halogen, perfluoroalkyl, perfluoroalkoxyl, —CN, —CONH$_2$, —CON(CH$_3$)$_2$, alkyl, alkoxy, hydroxylalkyl, and alkoxylalkyl; a 5- or 6-membered heterocycle, optionally substituted with 1, 2, or 3 substituents independently selected from the group consisting of halogen, perfluoroalkyl, perfluoroalkoxy, —CN, —CONH$_2$, —CON(CH$_3$)$_2$, alkyl, alkoxy, hydroxylalkyl, and alkoxylalkyl; a 5- or 6-membered heteroaryl, optionally substituted with 1, 2, or 3 substituents independently selected from the group consisting of halogen, perfluoroalkyl, perfluoroalkoxy, —CN, —CONH$_2$, —CON(CH$_3$)$_2$, alkyl, alkoxy, hydroxylalkyl, and alkoxylalkyl; or

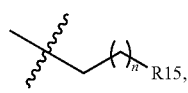

wherein n is 0, 1, 2, or 3; and R14 is hydrogen or R13; or

R13 and R14, together with the nitrogen to which they are attached, form a heterocycle containing 1, 2, or 3 heteroatoms selected independently from N, O, and S, optionally substituted with 1, 2, or 3 substitutents selected independently from R16;

R15 is amino; alkoxy; aryl, optionally substituted with 1, 2, or 3 substituents selected independently from the group consisting of halogen, perfluoroalkyl, perfluoroalkoxyl, —CN, —CONH$_2$, —CON(CH$_3$)$_2$, alkyl, alkoxy, hydroxylalkyl, and alkoxylalkyl; a 5- or 6-membered heterocycle having 1, 2, or 3 heteroatoms selected from N, O, and S and optionally substituted with 1, 2, or 3 substitutents selected from the group consisting of halogen, perfluoroalkyl, perfluoroalkoxy, —CN, —CONH$_2$, —CON(CH$_3$)$_2$, alkyl, alkoxy, hydroxylalkyl, and alkoxylalkyl; or a 5- or 6-membered heteroaryl having 1, 2, or 3 heteroatoms selected from N, O, and S and optionally substituted with 1, 2, or 3 substitutents selected from the group consisting of halogen, perfluoroalkyl, perfluoroalkoxy, —CN, —CONH$_2$, —CON(CH$_3$)$_2$, alkyl, alkoxy, hydroxylalkyl, and alkoxylalkyl;

R16 is hydrogen; alkyl; aryl; heteroaryl containing 1 or 2 heteroatoms selected from N, O, and S; arylalkyl; heteroarylalkyl in which the heteroaryl contains 1 or 2 heteroatoms selected from N, O, and S;

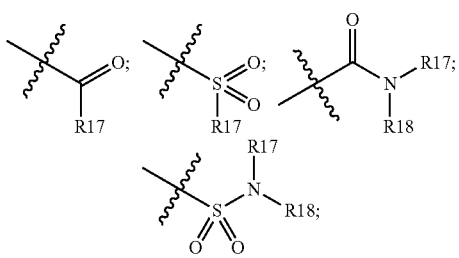

amino; or

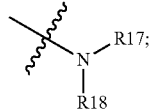

R17 is alkyl; alkoxylalkyl; perfluoroalkoxylalkyl; aryl, optionally substituted with 1, 2, or 3 substituents independently selected from the group consisting of halogen, perfluoroalkyl, perfluoroalkoxy, —CN, —CONH$_2$, —CON(CH$_3$)$_2$, alkyl, alkoxy, hydroxylalkyl, and alkoxylalkyl; a 5- or 6-membered heterocycle, optionally substituted with 1, 2, or 3 substituents independently selected from the group consisting of halogen, —CN, —CONH$_2$, —CON(CH$_3$)$_2$, perfluoroalkyl, perfluoroalkoxy, alkyl, alkoxy, hydroxylalkyl, and alkoxylalkyl; a 5- or 6-membered heteroaryl, optionally substituted with 1, 2, or 3 substituents independently selected from the group consisting of halogen, perfluoroalkyl, perfluoroalkoxy, —CN, —CONH$_2$, —CON(CH$_3$)$_2$, alkyl, alkoxy, hydroxylalkyl, and alkoxylalkyl; or

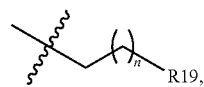

wherein n is 0, 1, 2, or 3; and R18 is hydrogen or R17; or

R17 and R18, together with the nitrogen to which they are attached, form a heterocycle containing 1, 2, 3, or 4 heteroatoms selected independently from N, O, and S, optionally substituted with 1, 2, or 3 substituents selected independently from R20;

R19 is alkoxy; aryl, optionally substituted with 1, 2, or 3 substituents selected independently from the group consisting of halogen, perfluoroalkyl, perfluoroalkoxyl, —CN, —CONH$_2$, —CON(CH$_3$)$_2$, alkyl, alkoxy, hydroxylalkyl, and alkoxylalkyl; a 5- or 6-membered heterocycle, optionally substituted with 1, 2, or 3 substituents independently selected from the group consisting of halogen, —CN, —CONH$_2$, —CON(CH$_3$)$_2$, perfluoroalkyl, perfluoroalkoxy, alkyl, alkoxy, hydroxylalkyl, and alkoxylalkyl; or a 5- or 6-membered heteroaryl, optionally substituted with 1, 2, or 3 substituents independently selected from the group consisting of halogen, perfluoroalkyl, perfluoroalkoxy, —CN, —CONH$_2$, —CON(CH$_3$)$_2$, alkyl, alkoxy, hydroxylalkyl, and alkoxylalkyl;

R20 is halogen; perfluoroalkyl; perfluoroalkoxy; —CN; —CONH$_2$; —CON(CH$_3$)$_2$; alkyl; alkoxy; hydroxylalkyl; alkoxylalkyl; and a 5- or 6-membered heterocycle having 1 or 2 heteroatoms selected from N, O, and S and optionally substituted with 1, 2, or 3 substituents selected independently from the group consisting of halogen, —CN, —CONH$_2$, —CON(CH$_3$)$_2$, perfluoroalkyl, perfluoroalkoxy, alkyl, alkoxy, hydroxylalkyl, and alkoxylalkyl; or a 5- or 6-membered heteroaryl, optionally substituted with 1, 2, or 3 substituents selected independently from the group consisting of halogen, —CN, —CONH$_2$, —CON(CH$_3$)$_2$, perfluoroalkyl, perfluoroalkoxy, alkyl, alkoxy, hydroxylalkyl, and alkoxylalkyl, with the exception of compounds in which R5, R6, R7, and R8 are independently hydrogen, halogen, —CH$_3$, —OCH$_3$, or hydroxymethyl;

in formula (1b):
R3, R4, R5, and R8 are hydrogen;
R6 and R7 independently are

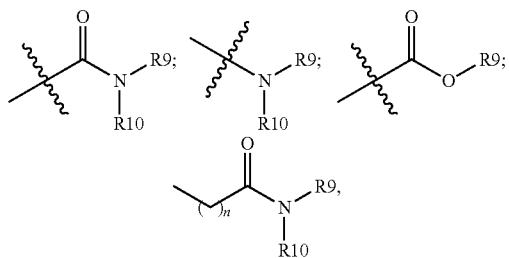

wherein n is 0, 1, or 2;

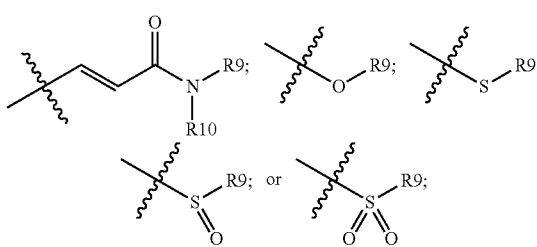

and
R9 and R10 are as defined above in connection with formula (1a), except that R7 and R6 cannot both be methoxy;

in formula (1c):
R3, R4, and R8 independently are hydrogen, halogen, —CN, —CONH$_2$, —CON(CH$_3$)$_2$, alkyl, C2-C6 alkoxy, hydroxylalkyl, or alkoxylalkyl;

R5, R6, and R7 independently are hydrogen; halogen; —CN; —CONH$_2$; —CON(CH$_3$)$_2$; alkyl; perfluoroalkyl; C2-C6 alkoxy; hydroxylalkyl; alkoxylalkyl; perfluoroalkoxyl;

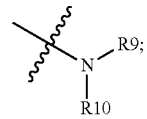

phenyl, optionally substituted with 1, 2, or 3 substituents independently selected from the group consisting of halogen, —CN, alkyl, perfluoroalkyl, alkoxy, hydroxylalkyl, alkoxylalkyl, perfluoroalkoxyl,

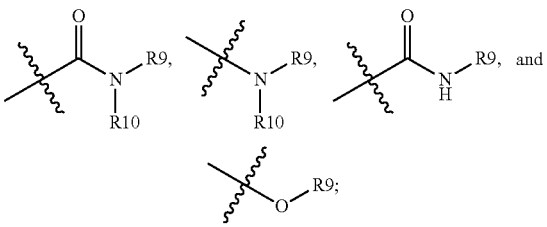

a 5- or 6-membered heteroaryl that is optionally mono-, or di-, or tri-substituted with halogen, —CN, alkyl, perfluoroalkyl, alkoxy, hydroxylalkyl, alkoxylalkyl, perfluoroalkoxyl,

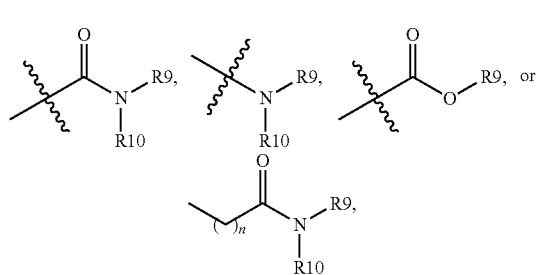

wherein n is 0, 1, or 2;

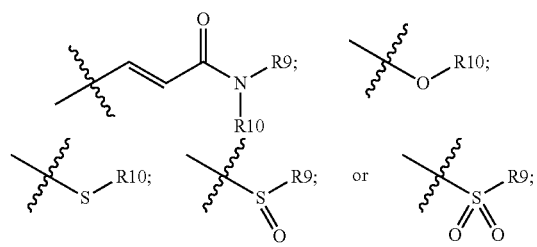

and
R9, R10, R11, and R12 are as defined above in connection with formula (1a), provided that either: (1) at least one of R3, R4, R5, and R8 is not hydrogen; or (2) if each of R4, R5, R6, R7, and R8 is hydrogen, R3 is not hydrogen, methoxy, or

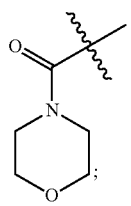 [SMILES: *C(=O)N1CCOCC1]

and
in formula (1d):
R3, R4, and R8 independently are hydrogen; halogen; perfluoroalkyl; —CN; —CONH$_2$; —CON(CH$_3$)$_2$; perfluoroalkoxy; alkyl; alkoxy; hydroxylalkyl; alkoxylalkyl;

R5, R6, and R7, provided that neither [R5, R6, and R7] nor [R3, R4, R5, R7, and R8] are simultaneously hydrogen, independently are hydrogen; halogen; —CN; —CONH$_2$; —CON(CH$_3$)$_2$; alkyl; perfluoroalkyl; C2-C6 alkoxy; hydroxylalkyl; alkoxylalkyl; perfluoroalkoxyl;

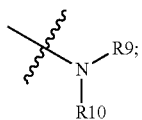

phenyl, optionally substituted with 1, 2, or 3 substitutents independently selected from the group consisting of —CN, perfluoroalkyl, alkoxy, alkoxylalkyl, perfluoroalkoxyl, and

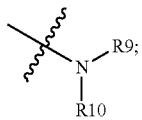

a 5- or 6-membered heteroaryl that is substituted with 1, 2, or 3 substitutents independently selected from the group consisting of —CN, alkyl, perfluoroalkyl, hydroxylalkyl, alkoxylalkyl, perfluoroalkoxyl,

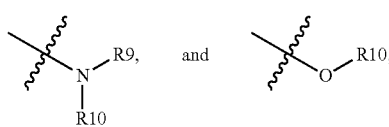

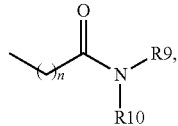 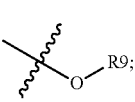

wherein n is 0, 1, or 2;

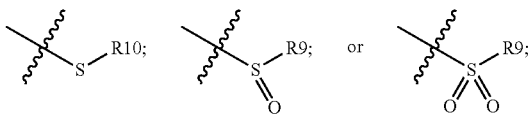

and

R9, R10, R11, and R12 are as defined above in connection with formula (1a), with the proviso that if R3, R4, R5, R8 and one of R6 and R7 are hydrogen, and the other of R6 and R7 is

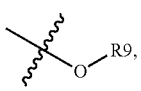

then R12 is not phenyl.

Examples of

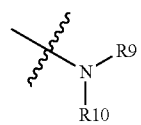

include the following, in which "X" is halogen, —CN, —CONH$_2$, —CON(CH$_3$)$_2$, C1-C4 alkyl, C1-C4 alkoxy, C1-C4 hydroxylalkyl, or C1-C4 alkoxylalkyl:

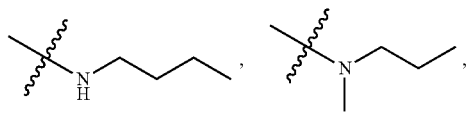

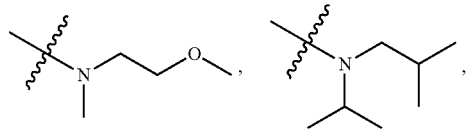

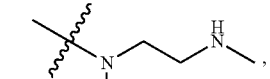

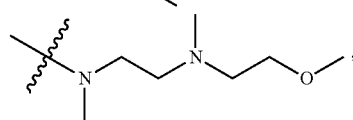

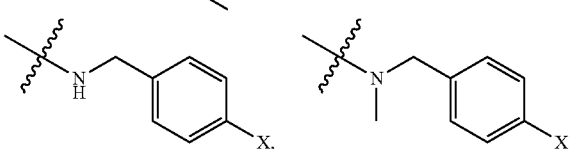

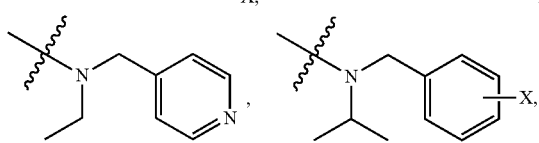

-continued

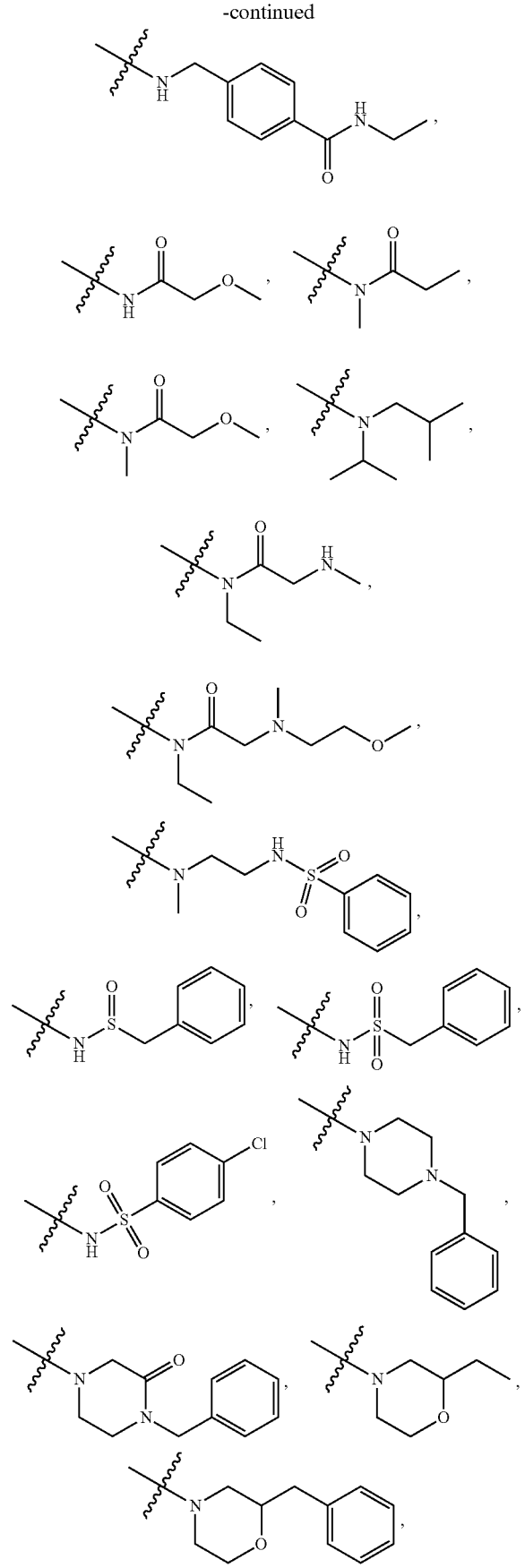
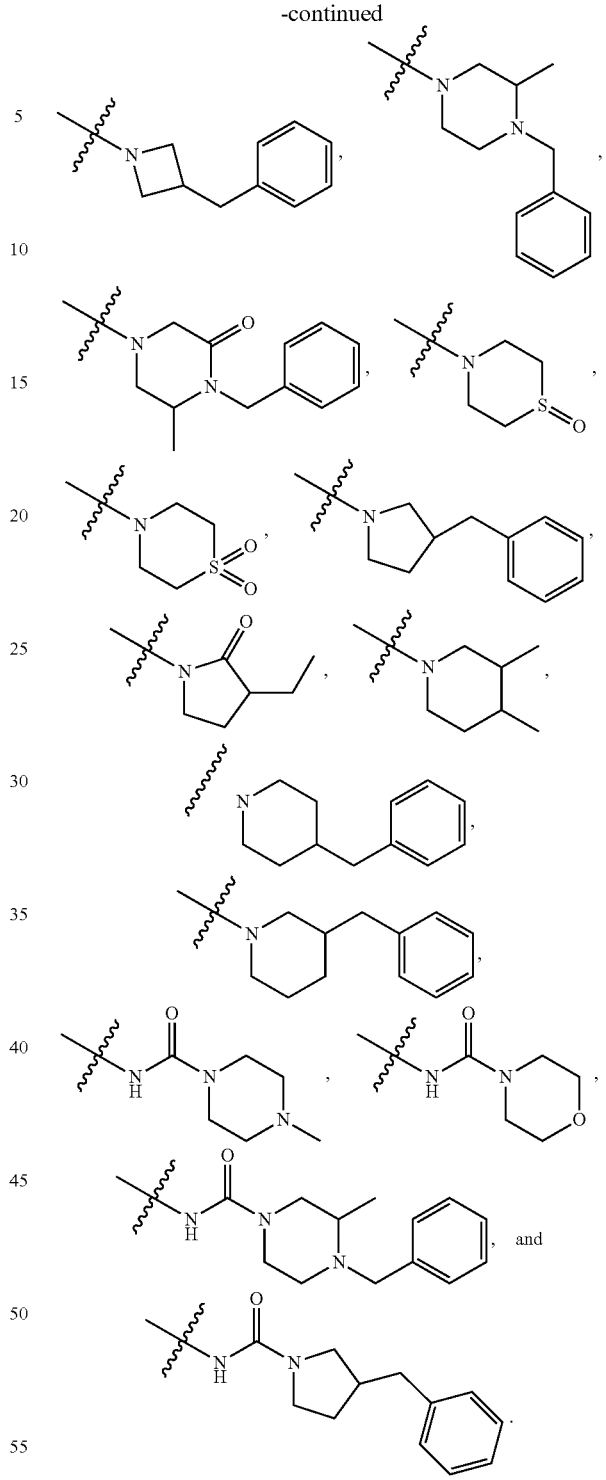

Another embodiment includes only those compounds of formula (1a) in which R6 is perfluoroalkyl, perfluoroalkoxy, —CN, alkyl, alkoxy, hydroxylalkyl, or alkoxylalkyl; and R7 is —CN; —CONH₂; —CON(CH₃)₂; alkyl; perfluoroalkyl; alkoxy; hydroxylalkyl; alkoxylalkyl; perfluoroalkoxyl; phenyl, optionally substituted with 1, 2, or 3 substituents independently selected from the group consisting of halogen, —CN, alkyl, perfluoroalkyl, alkoxy, hydroxylalkyl, alkoxylalkyl, perfluoroalkoxyl,

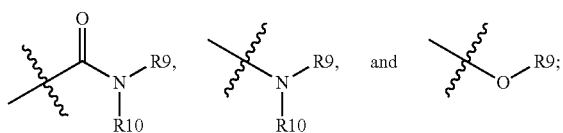 and a 5- or 6-membered heteroaryl attached via a carbon atom and that is substituted with 1, 2, or 3 substituents independently selected from the group consisting of halogen, —CN, alkyl, perfluoroalkyl, alkoxy, hydroxylalkyl, alkoxylalkyl, perfluoroalkoxyl,

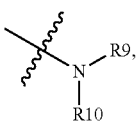

amino,

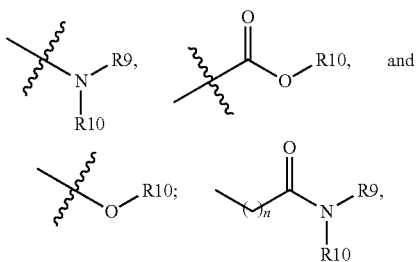

wherein n is 0, 1, or 2; and

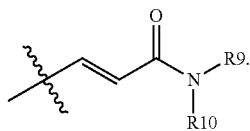

Another embodiment includes only those compounds of formula (1a) in which R5 is R7, and R7 is

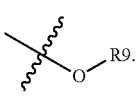

Another embodiment includes only those compounds of formula (1a) in which R5 is R7, and R7 is

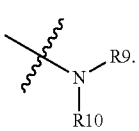

Another embodiment includes only those compounds of formula (1a) in which R5 is R7, and R7 is

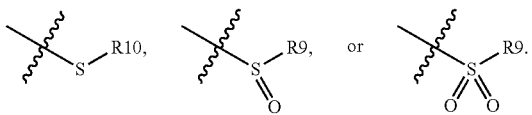

Another embodiment includes only those compounds of formula (1a) in which R9 and R10, together with the nitrogen atom to which they are attached, form a fused heterocycle containing 1, 2, 3, or 4 heteroatoms selected from N, O and S, with fewer than 12 atoms total, optionally substituted with 1, 2, or 3 substituents independently selected from R11.

Another embodiment includes only those compounds of formula (1a) in which R11 is aryl.

Another embodiment includes only those compounds of formula (1a) in which R11 is heteroaryl containing 1 or 2 heteroatoms selected from N, O, and S.

Another embodiment includes only those compounds of formula (1a) in which R11 is arylalkyl.

Another embodiment includes only those compounds of formula (1a) in which R11 is arylalkyl containing 1 or 2 heteroatoms selected from N, O, and S.

Another embodiment includes only those compounds of formula (1a) in which one or more of the alkyl, perfluoroalkyl, alkoxy, hydroxylalkyl, alkoxylalkyl, and perfluoroalkoxyl groups are C1-C4 alkyl, C1-C4 perfluoroalkyl, C1-C4 alkoxy, C1-C4 hydroxylalkyl, C1-C4 alkoxylalkyl, or C1-C4 perfluoroalkoxyl groups.

Another embodiment includes only those compounds of formula (1a) in which R4 and R8 are hydrogen. Among these compounds are those in which R5 is R7, and R7 is phenyl, optionally substituted with 1, 2, or 3 substituents independently selected from the group consisting of halogen, —CN, alkyl, perfluoroalkyl, alkoxy, hydroxylalkyl, alkoxylalkyl, perfluoroalkoxyl,

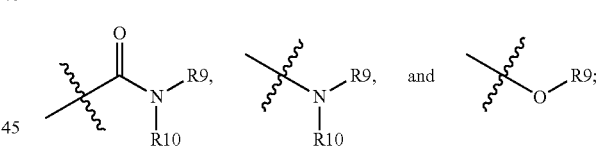 and or a 5- or 6-membered heteroaryl that is substituted with 1, 2, or 3 substituents independently selected from the group consisting of halogen, —CN, alkyl, perfluoroalkyl, alkoxy, hydroxylalkyl, alkoxylalkyl, perfluoroalkoxyl,

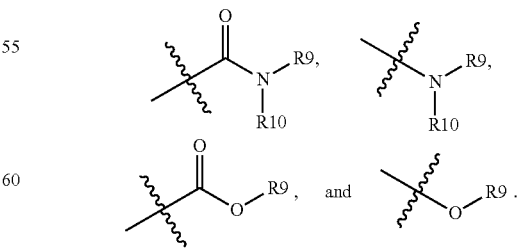

Another embodiment includes only those compounds of formula (1a) in which R4 and R8 are hydrogen; R5 is R7, and R7 is

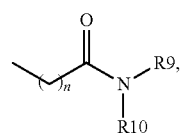

wherein n is 0, 1, or 2; or

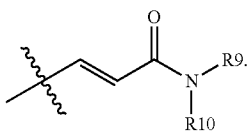

Another embodiment includes only those compounds of formula (1a) in which R4 and R8 are hydrogen; R5 is R7, and R7 is

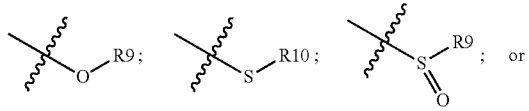

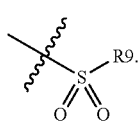

Another embodiment includes only those compounds of formula (1b) in which R6 and R7 independently are

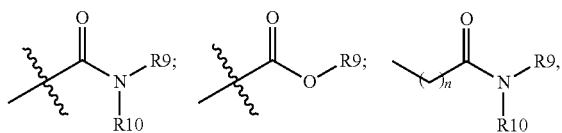

wherein n is 0, 1, or 2;

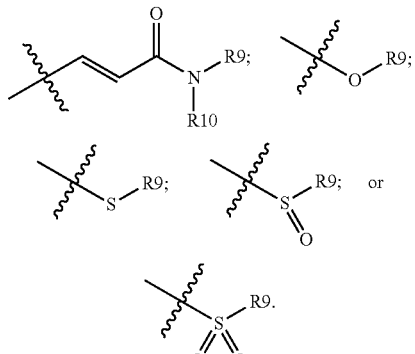

Another embodiment includes only those compounds of formula (1b) in which R6 and R7 independently are

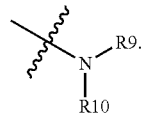

Another embodiment includes only those compounds of formula (1b) in which R6 and R7 independently are

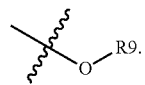

Another embodiment includes only those compounds of formula (1b) in which R6 and R7 independently are

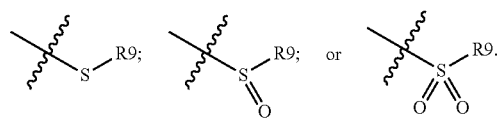

Another embodiment includes only those compounds of formula (1c) in which R5, R6, and R7 independently are

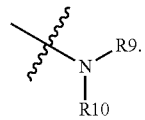

Another embodiment includes only those compounds of formula (1c) in which R5, R6, and R7 independently are —CN; —CONH$_2$; —CON(CH$_3$)$_2$; alkyl; perfluoroalkyl; C2-C6 alkoxy; hydroxylalkyl; alkoxylalkyl; perfluoroalkoxyl; phenyl, optionally substituted with 1, 2, or 3 substituents independently selected from the group consisting of halogen, —CN, alkyl, perfluoroalkyl, alkoxy, hydroxylalkyl, alkoxylalkyl, perfluoroalkoxyl,

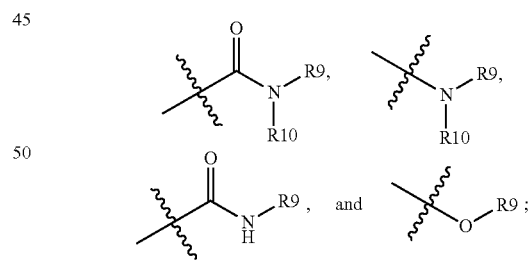

a 5- or 6-membered heteroaryl attached via a carbon and optionally mono-, or di-, or tri-substituted with halogen, —CN, alkyl, perfluoroalkyl, alkoxy, hydroxylalkyl, alkoxylalkyl, perfluoroalkoxyl,

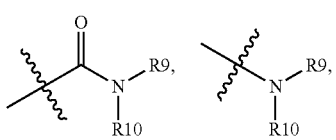

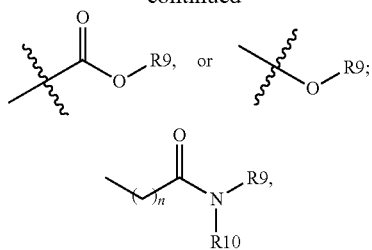

wherein n is 0, 1, or 2; or

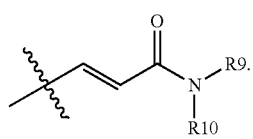

Another embodiment includes only those compounds of formula (1c) in which R5, R6, and R7 independently are

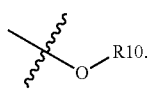

Another embodiment includes only those compounds of formula (1c) in which R5, R6, and R7 independently are

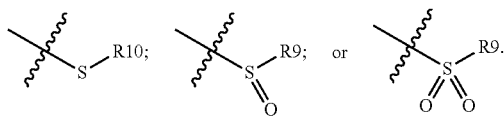

Another embodiment includes only those compounds of formula (1c) in which one or more of the alkyls, alkoxys, hydroxylalkyls, or alkoxylalkyls in formula (1d) independently are C1-C4 alkyl, C1-C4 alkoxy, C1-C4 hydroxylalkyl, or C1-C4 alkoxylalkyl.

Another embodiment includes only those compounds of formula (1d) in which R5, R6, and R7 independently are —CN; —CONH$_2$; —CON(CH$_3$)$_2$; alkyl; perfluoroalkyl; C2-C6 alkoxy; hydroxylalkyl; alkoxylalkyl; perfluoroalkoxyl; phenyl, optionally substituted with 1, 2, or 3 substitutents independently selected from the group consisting of —CN, perfluoroalkyl, alkoxy, alkoxylalkyl, perfluoroalkoxyl, and

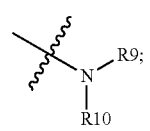

a 5- or 6-membered heteroaryl that is substituted with 1, 2, or 3 substitutents independently selected from the group consisting of —CN, alkyl, perfluoroalkyl, hydroxylalkyl, alkoxylalkyl, perfluoroalkoxyl,

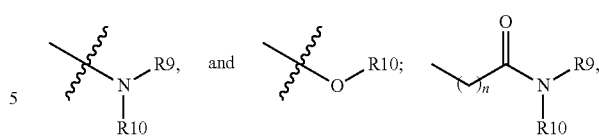

wherein n is 0, 1, or 2;

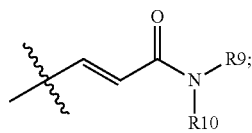

Another embodiment includes only those compounds of formula (1d) in which R5, R6, and R7 independently are

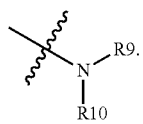

Another embodiment includes only those compounds of formula (1d) in which R5, R6, and R7 independently are

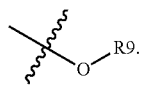

Another embodiment includes only those compounds of formula (1d) in which R5, R6, and R7 independently are

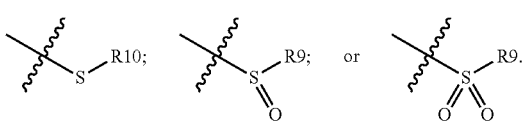

Another embodiment includes only those compounds of formula (1d) in which one or more of the alkyls, alkoxys, hydroxylalkyls, or alkoxylalkyls independently are C1-C4 alkyl, C2-C6 or C2-C4 alkoxy, C1-C4 hydroxylalkyl, or C1-C4 alkoxylalkyl.

Some embodiments of the invention include only compounds which have structural formula (2):

(2)

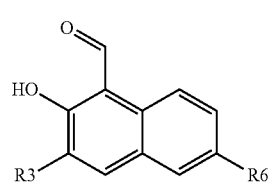

which encompasses structural formulae (2a), (2b), and (2c), wherein:

in formula (2a):
R3 is hydrogen; halogen; or alkyl;
R6 is

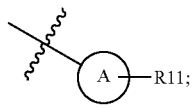

A is
(a) a 4-, 5-, or 6-membered saturated cycloalkyl; or
(b) a 4-, 5-, or 6-membered saturated heterocycle containing 1 or 2 heteroatoms selected from N, O, and S; and R11 is as defined above in connection with formula (1a);
in formula (2b):
R3 is hydrogen or —CN;
R6 is

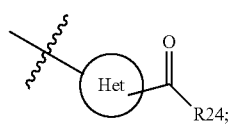

Het is a five-membered heteroaryl containing 1, 2, or 3 heteroatoms atoms selected from N, S, and O and optionally substituted with alkyl, provided that Het is not unsubstituted

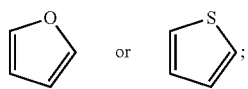 [SMILES: c1ccoc1 ; c1ccsc1]

R24 is —OH or

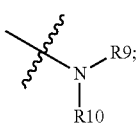

R9 and R10 independently are alkyl; or
R9 and R10, together with the atoms to which they are attached, form a 4-, 5-, 6-, or 7-membered heteroaryl or heterocycle containing 1 or 2 heteroatoms selected from N, O and S, optionally substituted with alkyl; or
R9 is hydrogen and R10 is

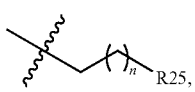

wherein n is 0, 1, 2, or 3; and
R25 is C1-C3 alkoxy or a 5- or 6-membered heteroaryl or heterocycle having one or two heteroatoms selected from N, O, and S and optionally substituted with alkyl, with the proviso that when Het is

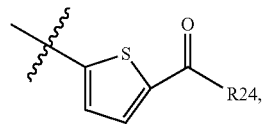

then R24 is not —OH,

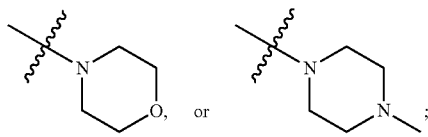

and
in formula (2c):
R3 is —OH, —CN, halogen, C1-C6 alkyl,

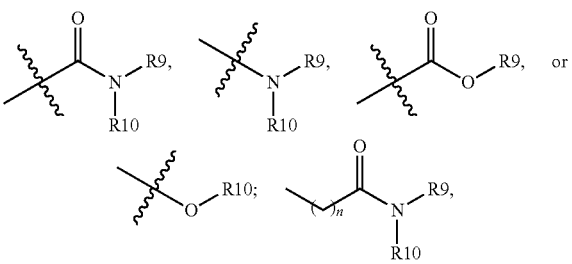

wherein n is 0, 1, or 2;
R6 is hydrogen or halogen; and
R9 and R10 are as defined above in connection with formula (1a).

Some embodiments include only those compounds of formula (2) in which R6 is linked via a carbon atom.

Some embodiments include only those compounds of formula (2) in which R6 is linked via a nitrogen atom.

Some embodiments include only those compounds of formula (2a) in which R3 is C1-C6 alkyl.

Another embodiment includes only those compounds of formula (2a) in which A is attached via a carbon atom.

Another embodiment includes only those compounds of formula (2a) in which A is a 4-, 5-, or 6-membered saturated heterocycle containing a nitrogen atom and is attached via the nitrogen atom.

Another embodiment includes only those compounds of formula (2a) in which A is

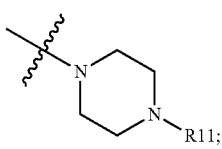

and R11 is as defined above in connection with formula (1a). In some of these compounds, R11 is selected from the group consisting of hydrogen; alkyl;

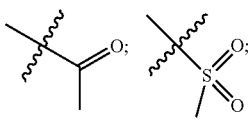

aryl; heteroaryl containing 1 or 2 heteroatoms selected from N, O, and S; arylalkyl; heteroarylalkyl in which the heteroaryl contains 1 or 2 heteroatoms selected from N, O, and S;

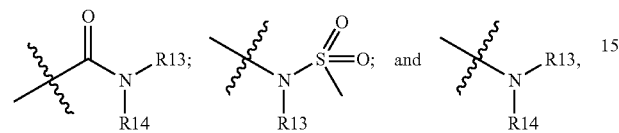

and R13 and R14 are as defined above in connection with formula (1a). In some of these compounds, the alkyl is C1-C6 or C1-C4 alkyl; the arylalkyl is aryl-C1-C6- or aryl-C1-C4 alkyl; and/or R3 is hydrogen, halogen, or alkyl (including C1-C6 and C1-C4 alkyl).

Another embodiment includes only those compounds of formula (2a) in which A is

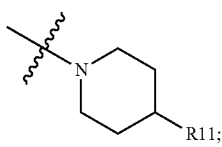

R11 is

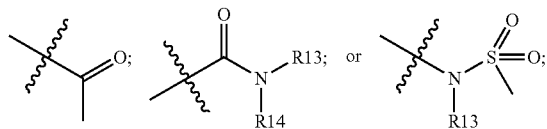

and R13 and R14 are as defined above in connection with formula (1a). In some compounds, the alkyl is C1-C4 alkyl. In some compounds, R3 is hydrogen.

Another embodiment includes only those compounds of formula (2a) in which A is

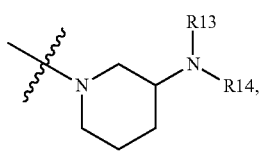

in which R13 is

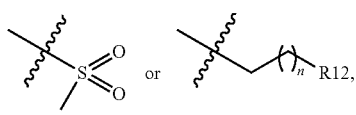

wherein n is 0, 1, 2, or 3; R14 is hydrogen or methyl; and R12 is C1-C3 alkoxy or a 6-membered heterocycle containing 0, 1, or 2 heteroatoms selected from N, O, and S.

Another embodiment includes only those compounds of formula (2a) in which A is

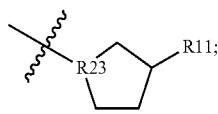

R23 is carbon or nitrogen; R11 is hydrogen,

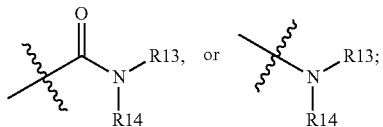

and R13 and R14 are as defined above in connection with formula (1a).

Another embodiment includes only those compounds of formula (2a) in which R13 is methyl; benzyl; or

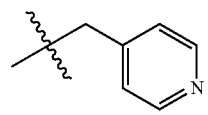 [SMILES: *Cc1ccncc1]

and R14 is R13 or hydrogen.

Another embodiment includes only those compounds of formula (2a) in which R13 and R14, together with the nitrogen to which they are attached, form a 6-membered heterocycle containing 1, 2, or 3 heteroatoms selected from N, O, and S, optionally substituted with C1-C6 or C1-C4 alkyl.

Another embodiment includes only those compounds of formula (2a) in which one or more of the alkyls, alkoxys, hydroxylalkyls, or alkoxylalkyls in formula (1d) independently are C1-C4 alkyl, C1-C4 alkoxy, C1-C4 hydroxylalkyl, or C1-C4 alkoxylalkyl.

Another embodiment includes only those compounds of formula (2b) in which Het is linked via a carbon atom.

Another embodiment includes only those compounds of formula (2b) in which Het is linked via a nitrogen atom.

Another embodiment includes only those compounds of formula (2b) in which one or more of the alkyls in formula (5b) is C1-C4 alkyl.

Another embodiment includes only those compounds of formula (2c) in which R3 is —CN, C1-C6 alkyl,

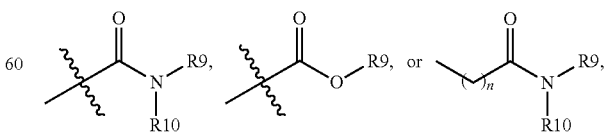

wherein n is 0, 1, or 2.

Another embodiment includes only those compounds of formula (2c) in which R3 is

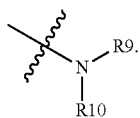

Another embodiment includes only those compounds of formula (2c) in which R3 is

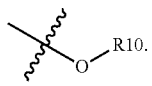

Some embodiments of the invention include only compounds which have structural formula (3):

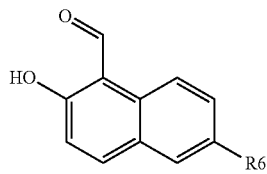

(3)

which encompasses formula (3a), (3b), (3c), (3d), (3e), (3f), (3g), and (3h), in which R6 is selected from the group consisting of:

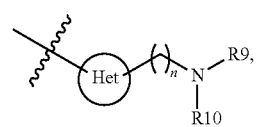

(3a)

in which
Het is a five-membered heteroaryl containing 1, 2, or 3 atoms selected from N, S, and O and optionally substituted with alkyl;
n is 0 or 1; and
R9 and R10, together with the nitrogen atom to which they are attached, form a 4-, 5-, 6-, or 7-membered heterocycle containing 1 or 2 heteroatoms selected from N, O, and S, optionally substituted with alkyl;

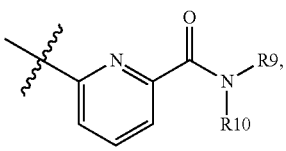

(3b)

wherein R9 and R10 are independently but not simultaneously hydrogen; or independently C1-C6 linear alkyl or C6 branched alkyl;

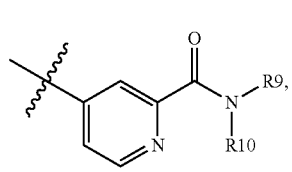

(3c)

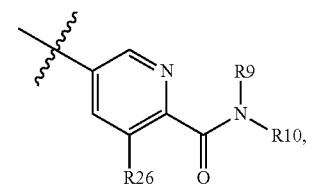

wherein R9 and R10 are as defined above in connection with formula (1a); and R26 is hydrogen or —NH$_2$;

(3d) pyrimidine substituted with halogen, C1-C3 alkoxy,

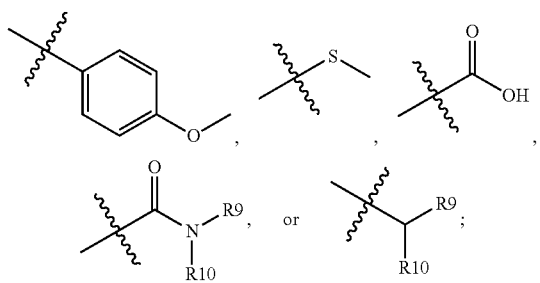

R9 and R10, together with the nitrogen atom to which they are attached, form a 4-, 5-, 6-, or 7-membered saturated heterocycle containing 1 or 2 heteroatoms and optionally substituted with alkyl; or R9 and R10 independently are alkyl; or R9 is hydrogen and R10 is

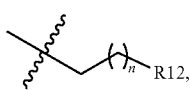

wherein n is 0, 1, 2, or 3; and R12 is alkoxy or a 5- or 6-membered saturated heterocycle having one or two heteroatoms selected from O, N, and S and optionally substituted with alkyl;

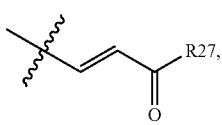
(3e)

in which R27 is —OH, alkoxy, or

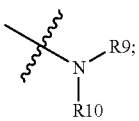

R9 and R10 independently are hydrogen, methyl, benzyl, or

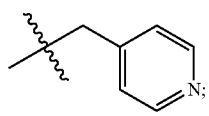 [SMILES: *Cc1ccncc1]

or R9 and R10, together with the nitrogen to which they are attached, form a 6-membered heterocycle containing 1 or 2 heteroatoms selected from N, O, and S, optionally substituted with alkyl;

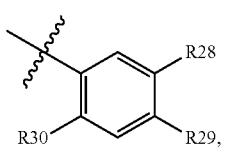
(3f)

in which R30 is hydrogen or halogen; one of R28 and R29 is hydrogen and the other is

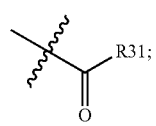

R31 is —OH or

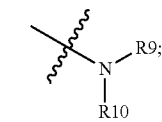

R9 and R10 independently are hydrogen, methyl, benzyl, or

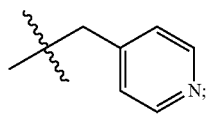

or R9 and R10, together with the nitrogen to which they are attached, form a 6-membered saturated heterocycle, optionally substituted with C1-C3 alkyl, provided that either (1) R30 and R28 are not both hydrogen; or (2) R30 and R29 are not both hydrogen;

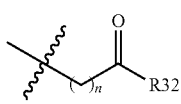
(3g)

in which R32 is alkoxy, —OH, or

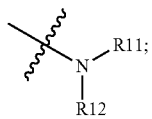

R12 is hydrogen and R11 is benzyl, optionally substituted with C1-C3 alkoxy; cyclohexane; a 6-membered saturated heterocycle with 1 or 2 heteroatoms selected from O, N, and S; or phenyl, optionally substituted with 1-methyl-piperazine or dimethyl-piperazine; or R11 and R12, together with the nitrogen atom to which they are attached, form a six-membered heterocycle containing 2 heteroatoms selected from N, O, and S, optionally substituted with C1-C3 alkyl or phenyl; and n is 1, 2, or 3; and

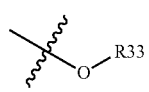
(3h)

in which R33 is C2-C6 alkyl; C2-C6 alkoxylalkyl; C2-C6 perfluoroalkoxylalkyl; aryl; a 5- or 6-membered heterocycle bonding through a carbon; or a 5- or 6-membered heteroaryl bonding through a carbon. Any of the C2-C6 alkyl, the C2-C6 alkoxylalkyl, the C2-C6 perfluoroalkoxylalkyl, the aryl, the 5- or 6-membered heterocycle, or the 5- or 6-membered heteroaryl are optionally substituted with 1, 2, or 3 substituents independently selected from the group consisting of halogen, perfluoroalkyl, perfluoroalkoxy, —CN, alkyl, alkoxy, hydroxylalkyl, alkoxylalkyl and

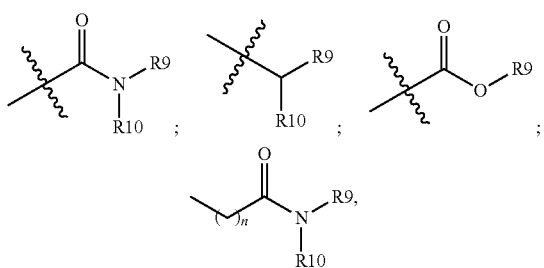

wherein n is 0, 1, or 2;

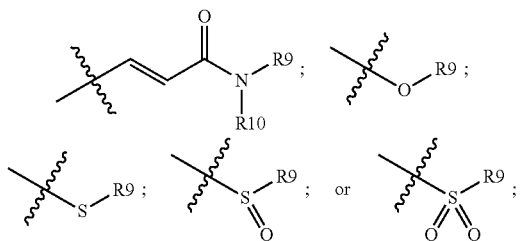

and R9 and R10 are as defined above in connection with formula (1a).

Another embodiment includes only those compounds of formula (3) in which R6 is linked via a carbon atom.

Another embodiment includes only those compounds of formula (3) in which R6 is linked via a nitrogen atom.

Another embodiment includes only those compounds of formula (3a) in which Het is linked via a carbon atom.

Another embodiment includes only those compounds of formula (3a) in which Het is substituted with C1-C6 or C1-C4 alkyl.

Another embodiment includes only those compounds of formula (3d) in which R6 is attached via a carbon atom.

Another embodiment includes only those compounds of formula (3d) in which R6 is attached via a nitrogen atom.

Another embodiment includes only those compounds of formula (3d) in which one or more of the alkyls is C1-C4 alkyl.

Another embodiment includes only those compounds of formula (3d) in which one or more of the alkoxys is C1-C4 alkoxy.

Another embodiment includes only those compounds of formula (3e) in which one or more of the alkyls is C1-C4 alkyl.

Another embodiment includes only those compounds of formula (3e) in which the alkoxy is C1-C4 alkoxy.

Another embodiment includes only those compounds of formula (3g) in which n is 2.

Another embodiment includes only those compounds of formula (3g) in which n is 2, R32 is —OH, alkoxy, or

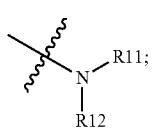

and R11 and R12 are independently hydrogen, C1-C4 alkyl, benzyl, or

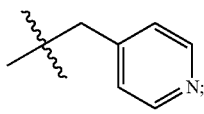 [SMILES: *Cc1ccncc1]

or R11 and R12, together with the nitrogen to which they are attached, form a 6-membered saturated heterocycle, optionally substituted with C1-C6 alkyl.

Some embodiments of the invention include only compounds which have structural formula (4):

(4)

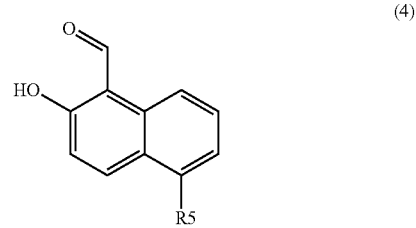

in which
R5 is

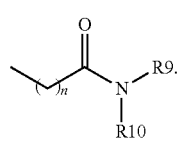

and
R9 and R10 are as defined above in connection with formula (1a).

Another embodiment includes only those compounds of formula (4) in which R9 is not —OH or methoxy.

Another embodiment includes only those compounds of formula (4) in which R5 is

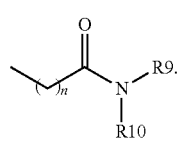

Another embodiment includes only those compounds of formula (4) in which R5 is

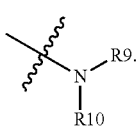

Another embodiment includes only those compounds of formula (4) in which R5 is

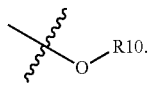

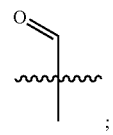

;

Table 1 provides examples of compounds encompassed by one or more of the structural formulas described above. In Table 1, "CHO" indicates "Bn" is benzyl; "Ph" is phenyl; and "Me" is methyl. The average $IC_{50}$ and $EC_{50}$ were determined as described in the Examples below.

TABLE 1

| Compound | Structure | IC50_av (μM) | EC50_av (μM) | Synthesis Example |
|---|---|---|---|---|
| 1 | 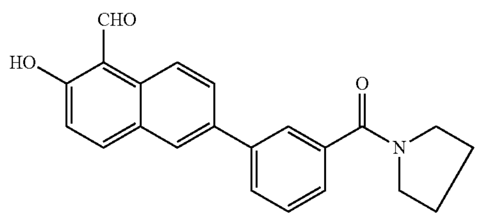 [SMILES: O=Cc1c(O)ccc2cc(-c3cccc(C(=O)N4CCCC4)c3)ccc12] | <0.1 | <10 | 12-16 |
| 2 | 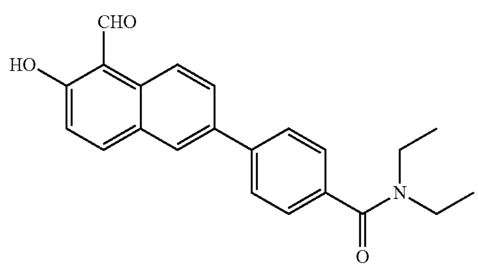 [SMILES: CCN(CC)C(=O)c1ccc(-c2ccc3c(C=O)c(O)ccc3c2)cc1] | <1 | <10 | 12-17 |
| 3 | 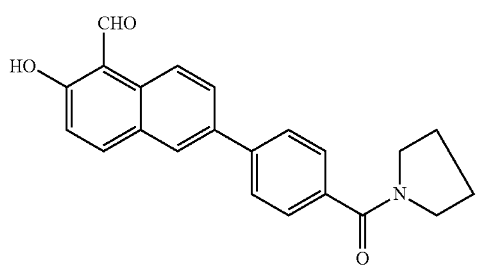 [SMILES: O=Cc1c(O)ccc2cc(-c3ccc(C(=O)N4CCCC4)cc3)ccc12] | <1 | <10 | 12-18 |
| 4 | 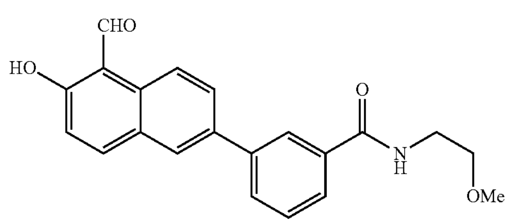 [SMILES: COCCNC(=O)c1cccc(-c2ccc3c(C=O)c(O)ccc3c2)c1] | <0.1 | <10 | 19-2 |
| 5 | 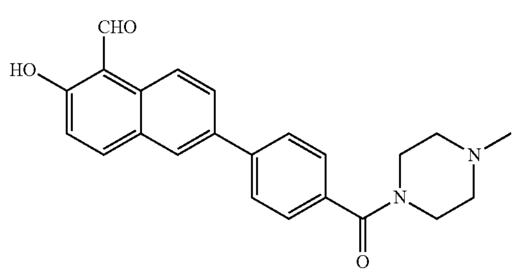 | <0.1 | <10 | 12-19 |

TABLE 1-continued

| Compound | Structure | IC50_av (μM) | EC50_av (μM) | Synthesis Example |
|---|---|---|---|---|
| 6 | 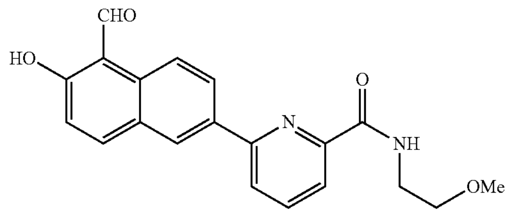 [SMILES: COCCNC(=O)c1cccc(-c2ccc3c(C=O)c(O)ccc3c2)n1] | <0.1 | >10 | 19-11 |
| 7 | 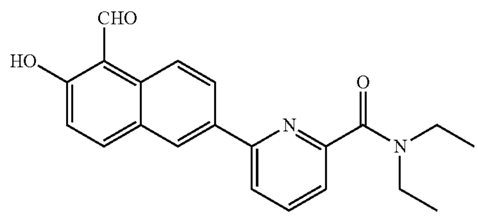 [SMILES: CCN(CC)C(=O)c1cccc(-c2ccc3c(C=O)c(O)ccc3c2)n1] | <1 | 10 | 19-22 |
| 8 | 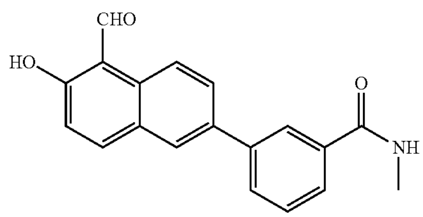 [SMILES: CNC(=O)c1cccc(-c2ccc3c(C=O)c(O)ccc3c2)c1] | <0.1 | <10 | 19-3 |
| 9 | 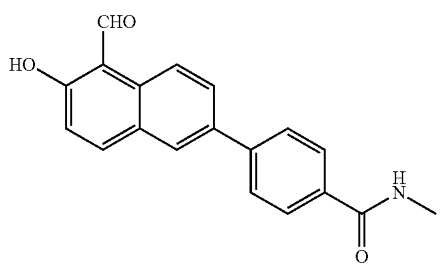 [SMILES: CNC(=O)c1ccc(-c2ccc3c(C=O)c(O)ccc3c2)cc1] | >1 | >10 | 19-12 |
| 10 | 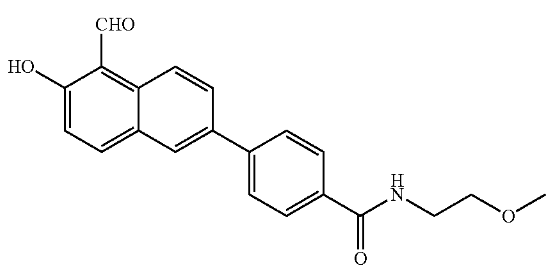 [SMILES: COCCNC(=O)c1ccc(-c2ccc3c(C=O)c(O)ccc3c2)cc1] | <1 | <10 | 19-4 |
| 11 | 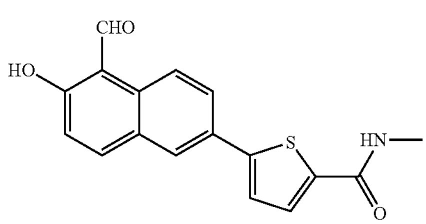 [SMILES: CNC(=O)c1ccc(-c2ccc3c(C=O)c(O)ccc3c2)s1] | <1 | 10 | 19-15 |

TABLE 1-continued

| Compound | Structure | IC50_av (μM) | EC50_av (μM) | Synthesis Example |
|---|---|---|---|---|
| 12 | 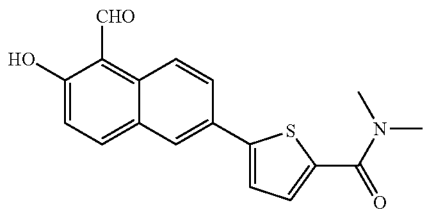 [SMILES: CN(C)C(=O)c1ccc(-c2ccc3c(C=O)c(O)ccc3c2)s1] | <1 | 10 | 19-18 |
| 13 | 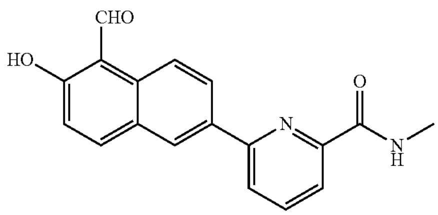 [SMILES: CNC(=O)c1cccc(-c2ccc3c(C=O)c(O)ccc3c2)n1] | <0.1 | >10 | 19-14 |
| 14 | 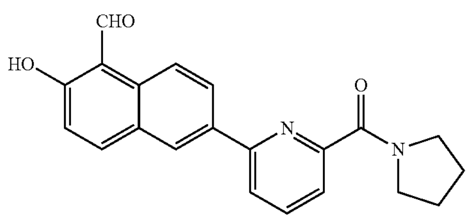 [SMILES: O=Cc1c(O)ccc2cc(-c3cccc(C(=O)N4CCCC4)n3)ccc12] | <0.1 | <10 | 19-23 |
| 15 | 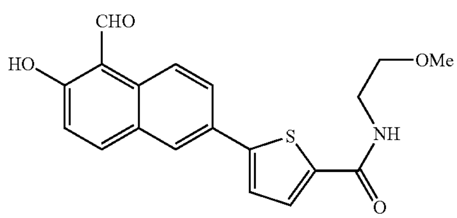 [SMILES: COCCNC(=O)c1ccc(-c2ccc3c(C=O)c(O)ccc3c2)s1] | <1 | >10 | 19-16 |
| 16 | 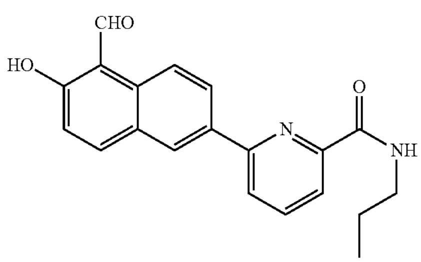 [SMILES: CCCNC(=O)c1cccc(-c2ccc3c(C=O)c(O)ccc3c2)n1] | <0.1 | 10 | 19-5 |
| 17 | 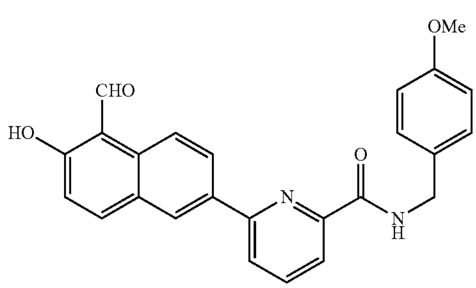 [SMILES: COc1ccc(CNC(=O)c2cccc(-c3ccc4c(C=O)c(O)ccc4c3)n2)cc1] | <1 | >10 | 19-13 |

TABLE 1-continued

| Compound | Structure | IC50_av (μM) | EC50_av (μM) | Synthesis Example |
|---|---|---|---|---|
| 18 | 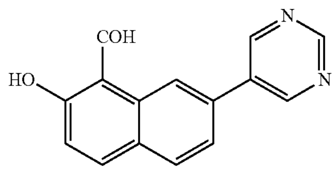 | <1 | 10 | 17-2 |
| 19 | 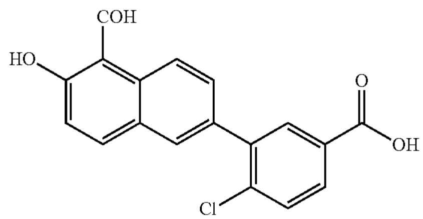 | <0.1 | nd | 17-1 |
| 20 | 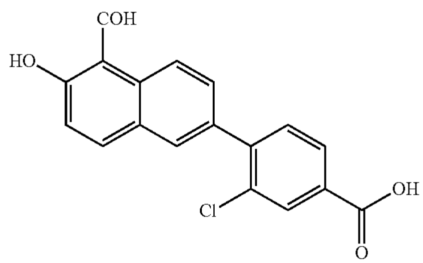 | <1 | nd | 17-3 |
| 21 | 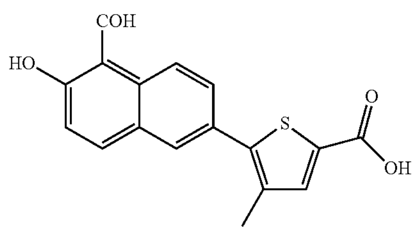 | 0.1 | <10 | 18-1 |
| 22 | 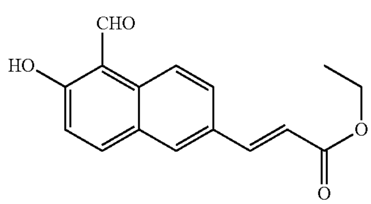 [SMILES: CCOC(=O)/C=C/c1ccc2c(C=O)c(O)ccc2c1] | <1 | <10 | 15-1 |
| 23 | 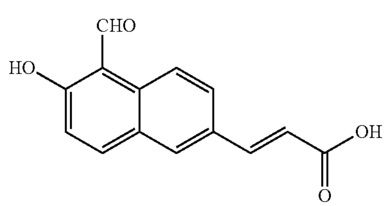 [SMILES: O=Cc1c(O)ccc2cc(/C=C/C(=O)O)ccc12] | <1 | 10 | 15-2 |
| 24 | 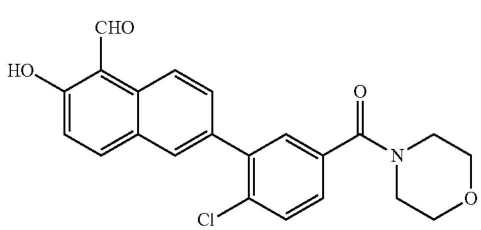 [SMILES: O=Cc1c(O)ccc2cc(-c3cc(C(=O)N4CCOCC4)ccc3Cl)ccc12] | >1 | >10 | 19-1 |

TABLE 1-continued

| Compound | Structure | IC50_av (μM) | EC50_av (μM) | Synthesis Example |
|---|---|---|---|---|
| 25 | 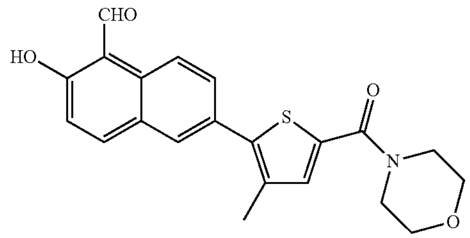 [SMILES: Cc1cc(C(=O)N2CCOCC2)sc1-c1ccc2c(C=O)c(O)ccc2c1] | <0.1 | >10 | 19-17 |
| 26 | 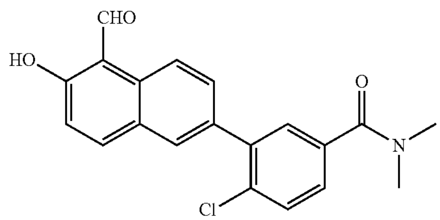 [SMILES: CN(C)C(=O)c1ccc(Cl)c(-c2ccc3c(C=O)c(O)ccc3c2)c1] | >1 | >10 | 19-6 |
| 27 | 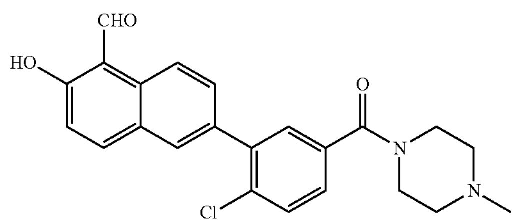 [SMILES: CN1CCN(C(=O)c2ccc(Cl)c(-c3ccc4c(C=O)c(O)ccc4c3)c2)CC1] | <1 | >10 | 19-7 |
| 28 | 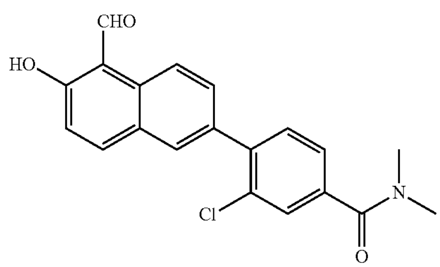 [SMILES: CN(C)C(=O)c1ccc(-c2ccc3c(C=O)c(O)ccc3c2)c(Cl)c1] | >1 | >10 | 19-8 |
| 29 | 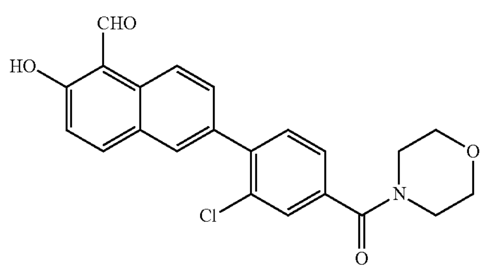 | <1 | >10 | 19-9 |
| 30 | 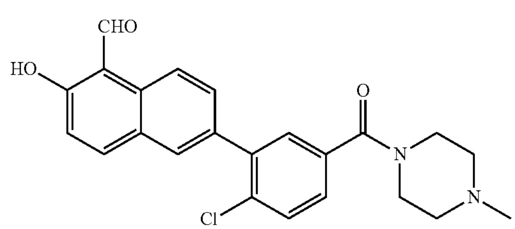 [SMILES: CN1CCN(C(=O)c2ccc(Cl)c(-c3ccc4c(C=O)c(O)ccc4c3)c2)CC1] | <1 | >10 | 19-10 |

TABLE 1-continued

| Compound | Structure | IC50_av (μM) | EC50_av (μM) | Synthesis Example |
|---|---|---|---|---|
| 31 | 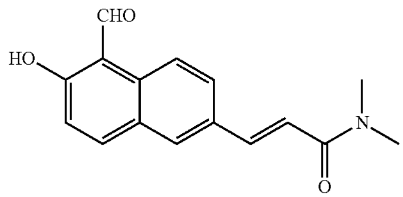 [SMILES: CN(C)C(=O)/C=C/c1ccc2c(C=O)c(O)ccc2c1] | <0.1 | >10 | 15-4 |
| 32 | 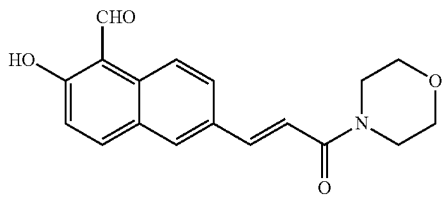 [SMILES: O=Cc1c(O)ccc2cc(/C=C/C(=O)N3CCOCC3)ccc12] | <0.1 | <10 | 15-3 |
| 33 | 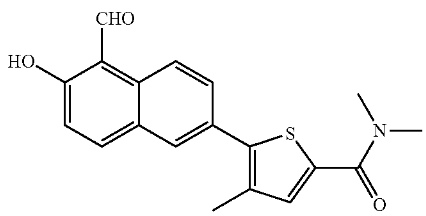 [SMILES: Cc1cc(C(=O)N(C)C)sc1-c1ccc2c(C=O)c(O)ccc2c1] | <0.1 | <10 | 19-24 |
| 34 | 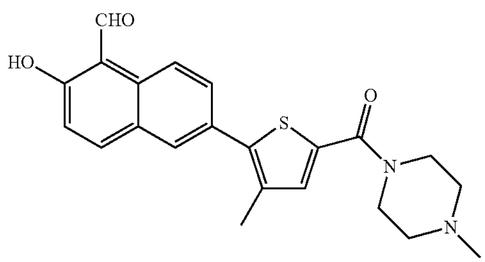 [SMILES: Cc1cc(C(=O)N2CCN(C)CC2)sc1-c1ccc2c(C=O)c(O)ccc2c1] | <0.1 | <10 | 19-19 |
| 35 | 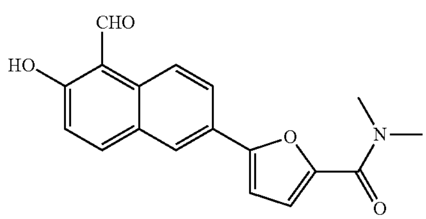 [SMILES: CN(C)C(=O)c1ccc(-c2ccc3c(C=O)c(O)ccc3c2)o1] | <0.1 | <10 | 19-25 |
| 36 | 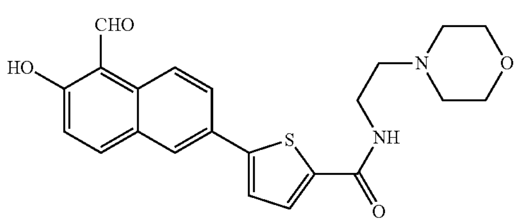 [SMILES: O=Cc1c(O)ccc2cc(-c3ccc(C(=O)NCCN4CCOCC4)s3)ccc12] | <0.1 | <10 | 19-26 |
| 37 | 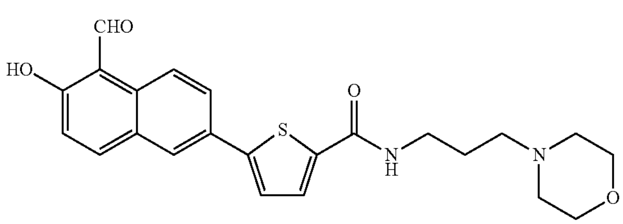 [SMILES: O=Cc1c(O)ccc2cc(-c3ccc(C(=O)NCCCN4CCOCC4)s3)ccc12] | <0.1 | <10 | 19-20 |

TABLE 1-continued

| Compound | Structure | IC50_av (μM) | EC50_av (μM) | Synthesis Example |
|---|---|---|---|---|
| 38 | 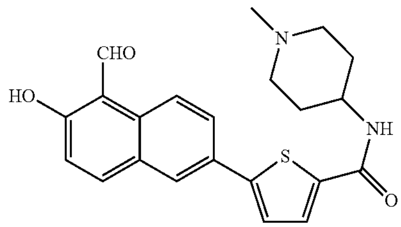 [SMILES: CN1CCC(NC(=O)c2ccc(-c3ccc4c(C=O)c(O)ccc4c3)s2)CC1] | <1 | <10 | 19-21 |
| 39 | 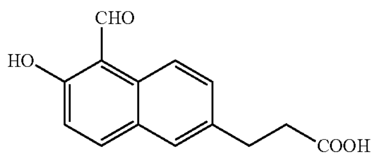 | <1 | >10 | 16-2 |
| 40 | 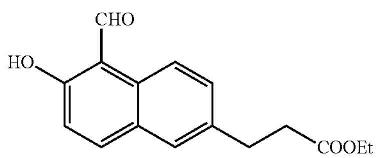 [SMILES: CCOC(=O)CCc1ccc2c(C=O)c(O)ccc2c1] | >1 | >10 | 16-1 |
| 41 | 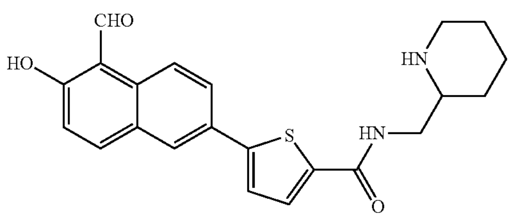 [SMILES: O=Cc1c(O)ccc2cc(-c3ccc(C(=O)NCC4CCCCN4)s3)ccc12] | <0.1 | <10 | 14-2 |
| 42 | 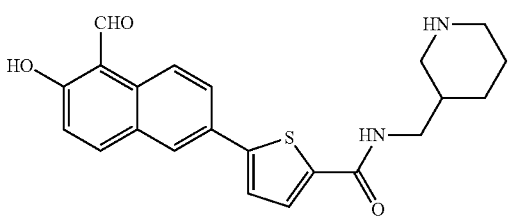 [SMILES: O=Cc1c(O)ccc2cc(-c3ccc(C(=O)NCC4CCCNC4)s3)ccc12] | <0.1 | <10 | 14-3 |
| 43 | 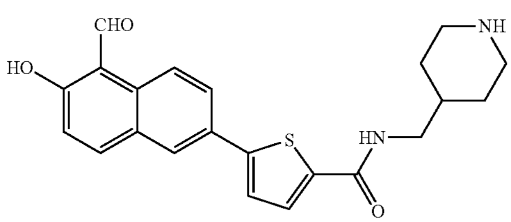 [SMILES: O=Cc1c(O)ccc2cc(-c3ccc(C(=O)NCC4CCNCC4)s3)ccc12] | <0.1 | <10 | 14-4 |
| 44 | 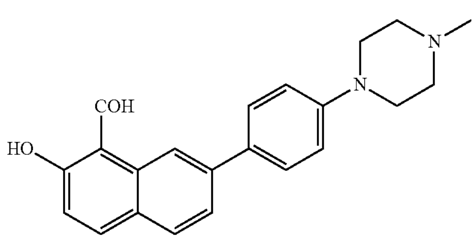 | >1 | <10 | 19-44 |

TABLE 1-continued

| Compound | Structure | IC50_av (μM) | EC50_av (μM) | Synthesis Example |
|---|---|---|---|---|
| 45 | 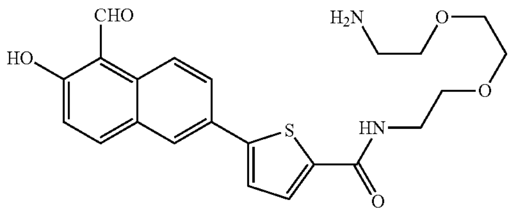 [SMILES: NCCOCCOCCNC(=O)c1ccc(-c2ccc3c(C=O)c(O)ccc3c2)s1] | <1 | <10 | 14-5 |
| 46 | 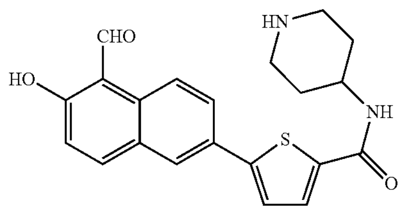 [SMILES: O=Cc1c(O)ccc2cc(-c3ccc(C(=O)NC4CCNCC4)s3)ccc12] | <0.1 | <10 | 14-6 |
| 47 | 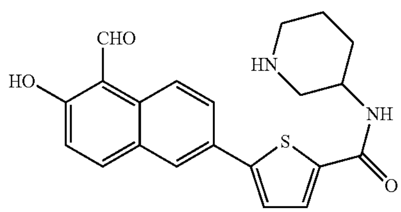 [SMILES: O=Cc1c(O)ccc2cc(-c3ccc(C(=O)NC4CCCNC4)s3)ccc12] | <0.1 | <10 | 14-7 |
| 48 | 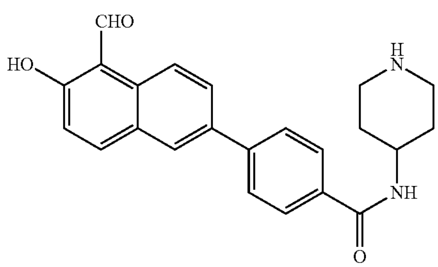 [SMILES: O=Cc1c(O)ccc2cc(-c3ccc(C(=O)NC4CCNCC4)cc3)ccc12] | <0.1 | <10 | 14-8 |
| 49 | 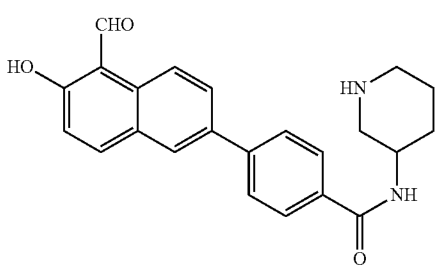 [SMILES: O=Cc1c(O)ccc2cc(-c3ccc(C(=O)NC4CCCNC4)cc3)ccc12] | <0.1 | <10 | 14-9 |
| 50 | 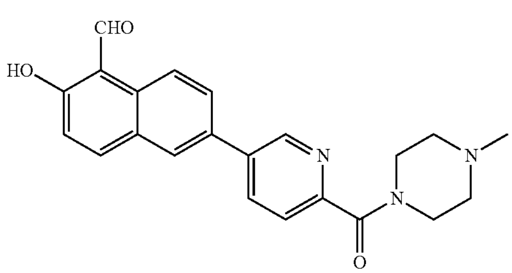 [SMILES: CN1CCN(C(=O)c2ccc(-c3ccc4c(C=O)c(O)ccc4c3)cn2)CC1] | <1 | <10 | 19-31 |

TABLE 1-continued

| Compound | Structure | IC50_av (μM) | EC50_av (μM) | Synthesis Example |
|---|---|---|---|---|
| 51 | 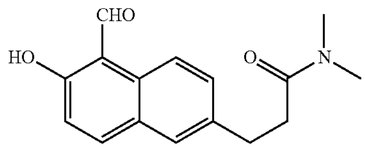 [SMILES: CN(C)C(=O)CCc1ccc2c(C=O)c(O)ccc2c1] | <1 | <10 | 16-4 |
| 52 | 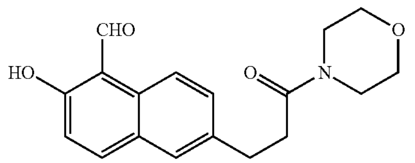 [SMILES: O=Cc1c(O)ccc2cc(CCC(=O)N3CCOCC3)ccc12] | <1 | <10 | 16-3 |
| 53 | 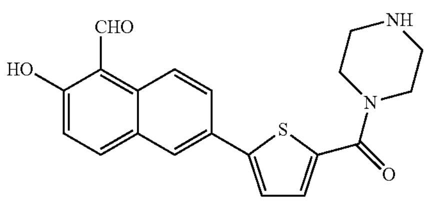 [SMILES: O=Cc1c(O)ccc2cc(-c3ccc(C(=O)N4CCNCC4)s3)ccc12] | <1 | <10 | 19-27 |
| 54 | 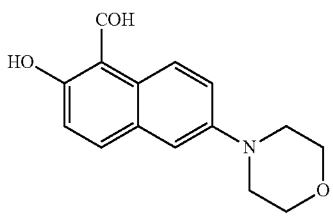 | >1 | >10 | 1-25 |
| 55 | 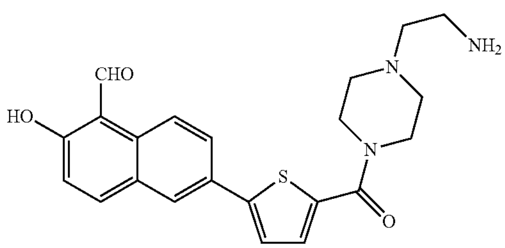 [SMILES: NCCN1CCN(C(=O)c2ccc(-c3ccc4c(C=O)c(O)ccc4c3)s2)CC1] | <1 | <10 | 19-28 |
| 56 | 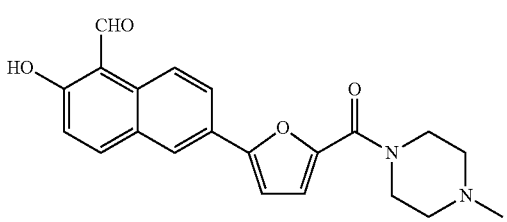 [SMILES: CN1CCN(C(=O)c2ccc(-c3ccc4c(C=O)c(O)ccc4c3)o2)CC1] | <1 | <10 | 19-29 |
| 57 | 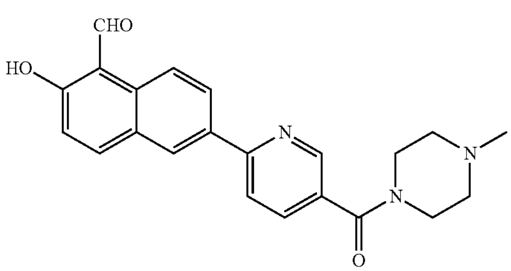 [SMILES: CN1CCN(C(=O)c2ccc(-c3ccc4c(C=O)c(O)ccc4c3)nc2)CC1] | <1 | <10 | 19-30 |

TABLE 1-continued

| Compound | Structure | IC50_av (μM) | EC50_av (μM) | Synthesis Example |
|---|---|---|---|---|
| 58 | 1-CHO, 2-OH, 6-(4-methylpiperazin-1-yl)naphthalene | >1 | <10 | 1-1 |
| 59 | 1-CHO, 2-OH, 6-(pyrrolidin-1-yl)naphthalene | >1 | >10 | 1-3 |
| 60 | 1-CHO, 2-OH, 6-[4-(4-methylpiperazine-1-carbonyl)thiazol-2-yl]naphthalene | <0.1 | <10 | 12-2 |
| 61 | 1-CHO, 2-OH, 6-[5-(4-methylpiperazine-1-carbonyl)thiazol-2-yl]naphthalene | <0.1 | <10 | 12-3 |
| 62 | 1-CHO, 2-OH, 6-{5-[(1-methylpiperidin-2-yl)methylcarbamoyl]thiophen-2-yl}naphthalene | <0.1 | <10 | 13-2 |
| 63 | 1-CHO, 2-OH, 6-[(E)-3-(4-methylpiperazin-1-yl)-3-oxoprop-1-en-1-yl]naphthalene | <1 | <10 | 15-5 |
| 64 | 1-CHO, 2-OH, 6-[2-(methylthio)pyrimidin-5-yl]naphthalene | >1 | >10 | 20-2 |

TABLE 1-continued

| Compound | Structure | IC50_av (μM) | EC50_av (μM) | Synthesis Example |
|---|---|---|---|---|
| 65 | (naphthalene with CHO and OH, connected to 4-methylthiazole-5-carbonyl-(4-methylpiperazine)) | <0.1 | <10 | 12-4 |
| 66 | (naphthalene with CHO and OH, connected to pyridine-2-carbonyl-(4-methylpiperazine)) | <1 | <10 | 19-31 |
| 67 | (naphthalene with CHO and OH, connected to pyridine-3-carbonyl-(4-methylpiperazine)) | <1 | <10 | 19-33 |
| 68 | (naphthalene with CHO and OH, connected to pyridine-4-carbonyl-(4-methylpiperazine)) | <1 | <10 | 19-34 |
| 69 | (naphthalene with CHO and OH, connected to thiophene-carboxamide-(1-methylpiperidin-3-yl)methyl) | <0.1 | <10 | 13-3 |
| 70 | (naphthalene with CHO and OH, connected to furan-carboxamide-(piperidin-3-yl)) | <1 | <10 | 14-10 |
| 71 | (naphthalene with CHO and OH, connected to furan-carboxamide-(2-morpholinoethyl)) | <0.1 | <10 | 12-8 |

TABLE 1-continued

| Compound | Structure | IC50_av (μM) | EC50_av (μM) | Synthesis Example |
|---|---|---|---|---|
| 72 | 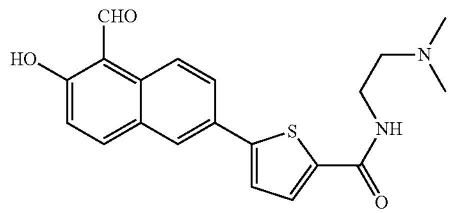 [SMILES: CN(C)CCNC(=O)c1ccc(-c2ccc3c(C=O)c(O)ccc3c2)s1] | <0.1 | <10 | 12-9 |
| 73 | 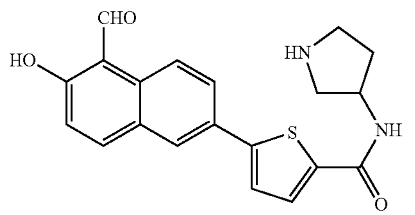 [SMILES: O=Cc1c(O)ccc2cc(-c3ccc(C(=O)NC4CCNC4)s3)ccc12] | <0.1 | <10 | 14-11 |
| 74 | 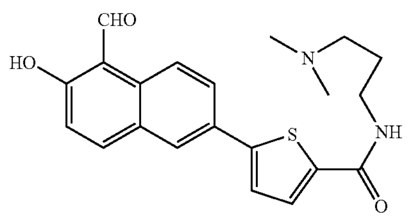 [SMILES: CN(C)CCCNC(=O)c1ccc(-c2ccc3c(C=O)c(O)ccc3c2)s1] | <1 | >10 | 12-10 |
| 75 | 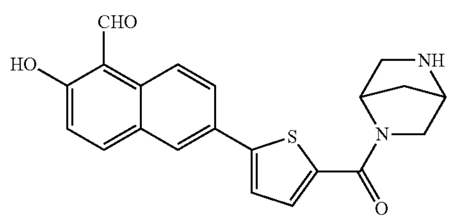 [SMILES: O=Cc1c(O)ccc2cc(-c3ccc(C(=O)N4CC5CC4CN5)s3)ccc12] | <0.1 | <10 | 19-35 |
| 76 | 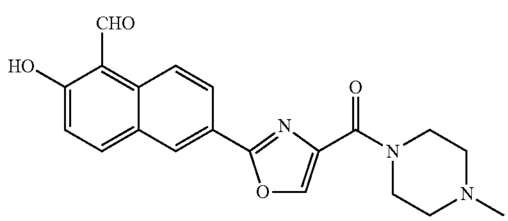 [SMILES: CN1CCN(C(=O)c2coc(-c3ccc4c(C=O)c(O)ccc4c3)n2)CC1] | <1 | <10 | 12-5 |
| 77 | 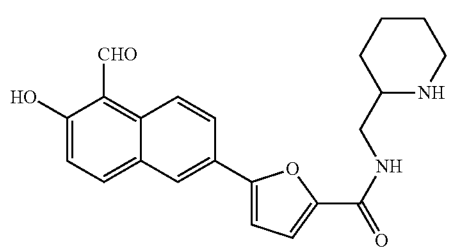 [SMILES: O=Cc1c(O)ccc2cc(-c3ccc(C(=O)NCC4CCCCN4)o3)ccc12] | >1 | <10 | 14-12 |
| 78 | 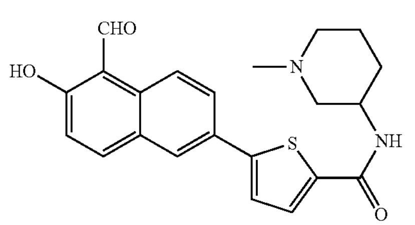 [SMILES: CN1CCCC(NC(=O)c2ccc(-c3ccc4c(C=O)c(O)ccc4c3)s2)C1] | <0.1 | <10 | 13-4 |

TABLE 1-continued
| Compound | Structure | IC50_av (μM) | EC50_av (μM) | Synthesis Example |
|---|---|---|---|---|
| 79 | 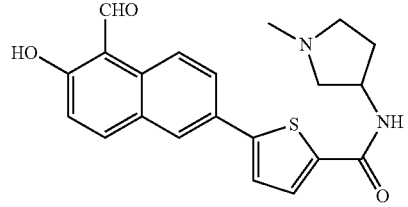 | <0.1 | <10 | 12-6 |
| 80 | 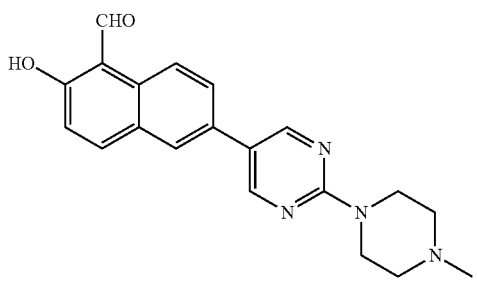 [SMILES: CN1CCN(c2ncc(-c3ccc4c(C=O)c(O)ccc4c3)cn2)CC1] | <0.1 | <10 | 20-3 |
| 81 | 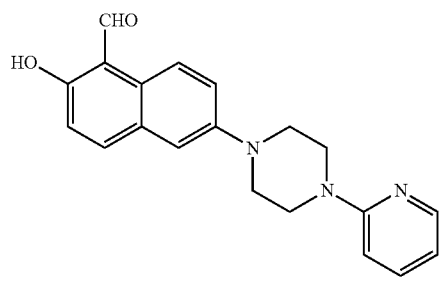 [SMILES: O=Cc1c(O)ccc2cc(N3CCN(c4ccccn4)CC3)ccc12] | >1 | >10 | 1-4 |
| 82 | 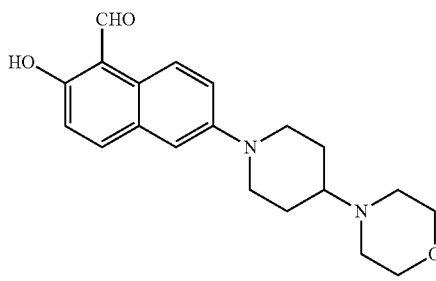 | <1 | <10 | 1-5 |
| 83 | 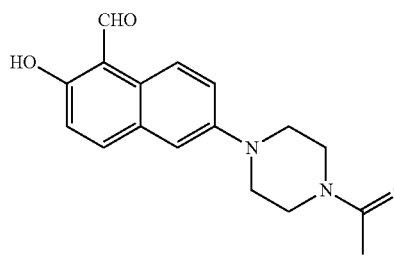 | <1 | >10 | 1-6 |
| 84 | 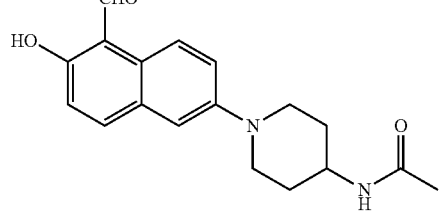 | <1 | >10 | 1-7 |

TABLE 1-continued

| Compound | Structure | IC50_av (μM) | EC50_av (μM) | Synthesis Example |
|---|---|---|---|---|
| 85 | 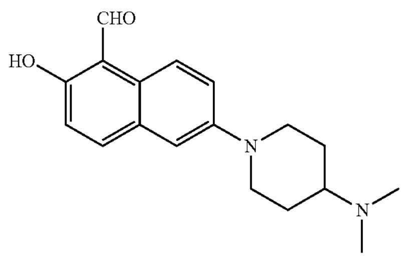 [SMILES: CN(C)C1CCN(c2ccc3c(C=O)c(O)ccc3c2)CC1] | <0.01 | <10 | 1-8 |
| 86 | 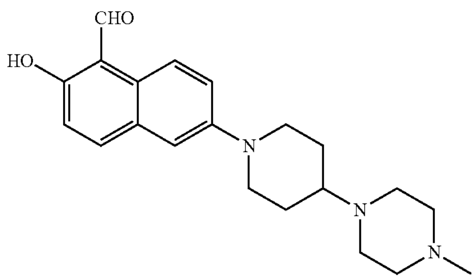 [SMILES: CN1CCN(C2CCN(c3ccc4c(C=O)c(O)ccc4c3)CC2)CC1] | <0.01 | <10 | 1-9 |
| 87 | 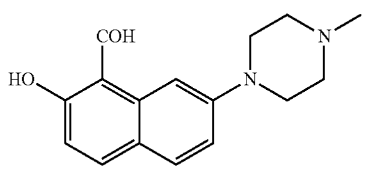 | >1 | >10 | 1-10 |
| 88 | 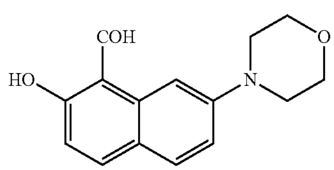 | >1 | <10 | 1-11 |
| 89 | 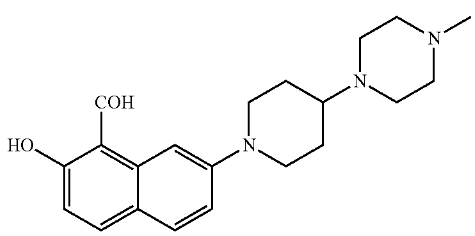 | >1 | >10 | 1-12 |
| 90 | 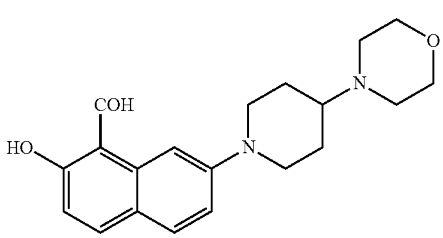 | >1 | <10 | 1-13 |

TABLE 1-continued

| Compound | Structure | IC50_av (μM) | EC50_av (μM) | Synthesis Example |
|---|---|---|---|---|
| 91 | 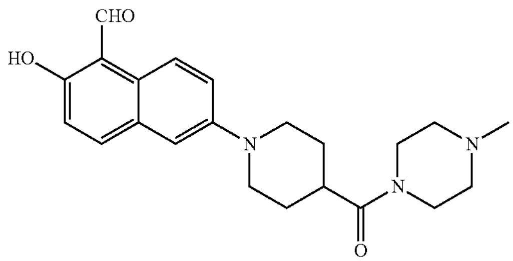 [SMILES: CN1CCN(C(=O)C2CCN(c3ccc4c(C=O)c(O)ccc4c3)CC2)CC1] | >1 | >10 | 2-3 |
| 92 | 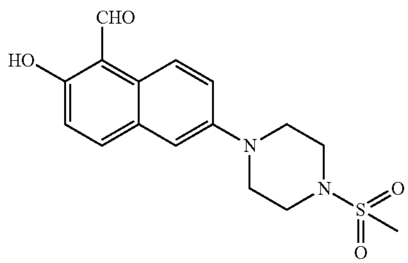 [SMILES: CS(=O)(=O)N1CCN(c2ccc3c(C=O)c(O)ccc3c2)CC1] | >1 | >10 | 4-1 |
| 93 | 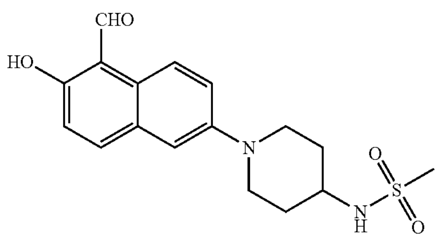 [SMILES: CS(=O)(=O)NC1CCN(c2ccc3c(C=O)c(O)ccc3c2)CC1] | >1 | <10 | 4-3 |
| 94 | 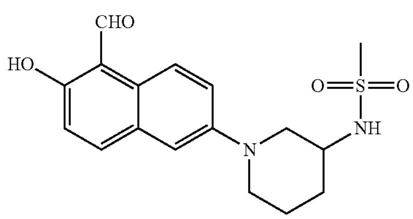 [SMILES: CS(=O)(=O)NC1CCCN(c2ccc3c(C=O)c(O)ccc3c2)C1] | >1 | >10 | 4-4 |
| 95 | 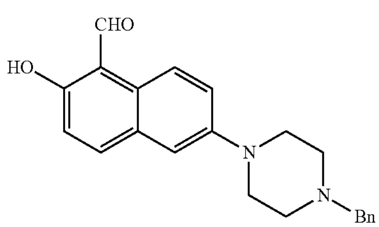 [SMILES: O=Cc1c(O)ccc2cc(N3CCN(Cc4ccccc4)CC3)ccc12] | >1 | >10 | 3-5 |
| 96 | 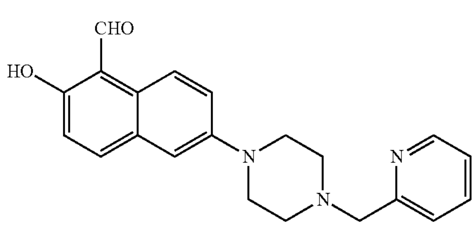 [SMILES: O=Cc1c(O)ccc2cc(N3CCN(Cc4ccccn4)CC3)ccc12] | 1 | >10 | 3-1 |

TABLE 1-continued

| Compound | Structure | IC50_av (μM) | EC50_av (μM) | Synthesis Example |
|---|---|---|---|---|
| 97 | 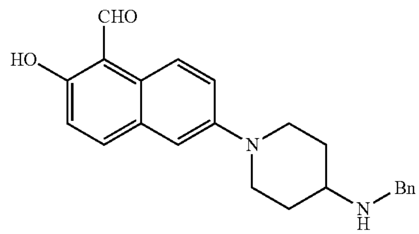 [SMILES: O=Cc1c(O)ccc2cc(N3CCC(NCc4ccccc4)CC3)ccc12] | <1 | >10 | 3-3 |
| 98 | 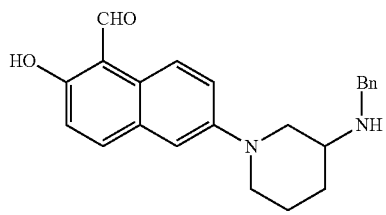 [SMILES: O=Cc1c(O)ccc2cc(N3CCCC(NCc4ccccc4)C3)ccc12] | 1 | <10 | 3-4 |
| 99 | 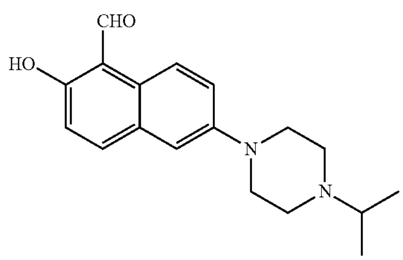 [SMILES: CC(C)N1CCN(c2ccc3c(C=O)c(O)ccc3c2)CC1] | >1 | <10 | 1-14 |
| 100 | 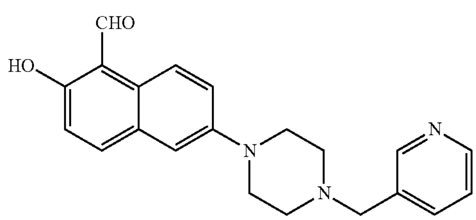 [SMILES: O=Cc1c(O)ccc2cc(N3CCN(Cc4cccnc4)CC3)ccc12] | <1 | >10 | 3-7 |
| 101 | 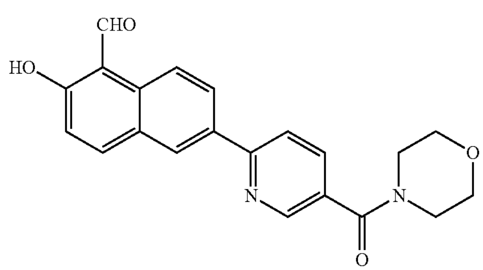 [SMILES: O=Cc1c(O)ccc2cc(-c3ccc(C(=O)N4CCOCC4)cn3)ccc12] | <1 | >10 | 19-36 |
| 102 | 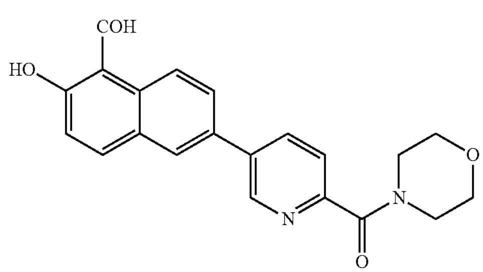 | <1 | <10 | 19-37 |

TABLE 1-continued

| Compound | Structure | IC50_av (μM) | EC50_av (μM) | Synthesis Example |
|---|---|---|---|---|
| 103 | 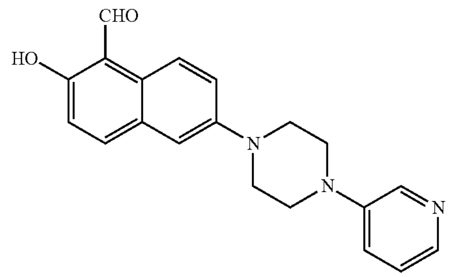 [SMILES: O=Cc1c(O)ccc2cc(N3CCN(c4cccnc4)CC3)ccc12] | >1 | >10 | 1-22 |
| 104 | 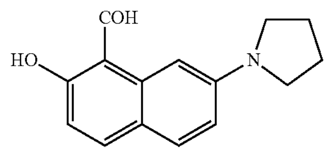 | >1 | >10 | 1-23 |
| 105 | 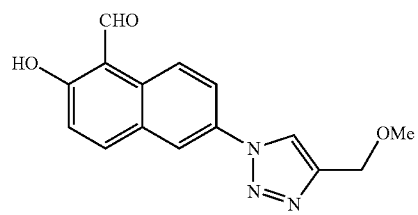 [SMILES: COCc1cn(-c2ccc3c(C=O)c(O)ccc3c2)nn1] | <1 | <10 | 1-26 |
| 106 | 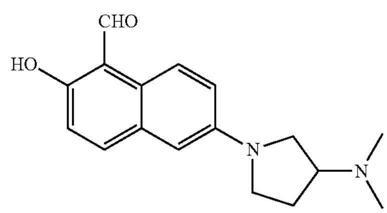 [SMILES: CN(C)C1CCN(c2ccc3c(C=O)c(O)ccc3c2)C1] | >1 | >10 | 1-2 |
| 107 | 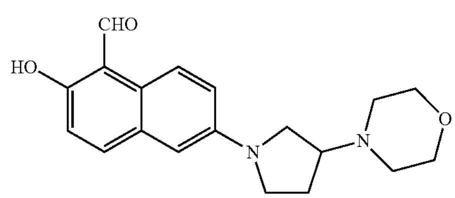 [SMILES: O=Cc1c(O)ccc2cc(N3CCC(N4CCOCC4)C3)ccc12] | >1 | >10 | 1-24 |
| 108 | 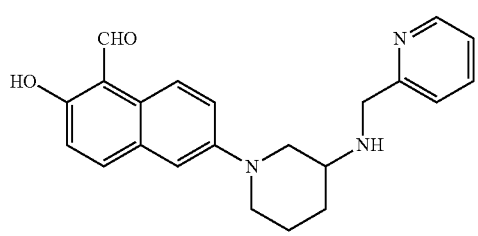 [SMILES: O=Cc1c(O)ccc2cc(N3CCCC(NCc4ccccn4)C3)ccc12] | >1 | >10 | 3-8 |
| 109 | 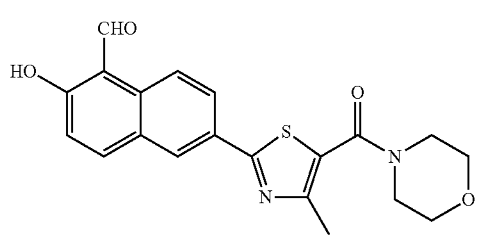 [SMILES: Cc1nc(-c2ccc3c(C=O)c(O)ccc3c2)sc1C(=O)N1CCOCC1] | <0.1 | <10 | 12-1 |

TABLE 1-continued

| Compound | Structure | IC50_av (μM) | EC50_av (μM) | Synthesis Example |
|---|---|---|---|---|
| 110 | 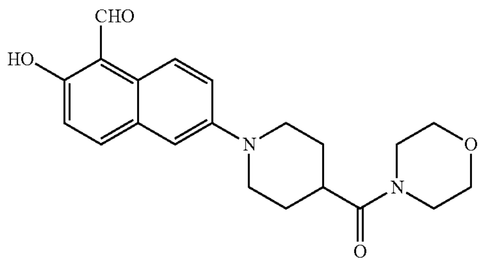 [SMILES: O=Cc1c(O)ccc2cc(N3CCC(C(=O)N4CCOCC4)CC3)ccc12] | <1 | >10 | 2-2 |
| 111 | 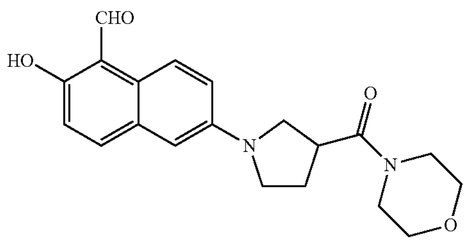 [SMILES: O=Cc1c(O)ccc2cc(N3CCC(C(=O)N4CCOCC4)C3)ccc12] | <1 | >10 | 2-1 |
| 112 | 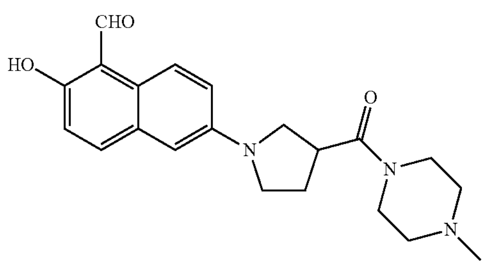 [SMILES: CN1CCN(C(=O)C2CCN(c3ccc4c(C=O)c(O)ccc4c3)C2)CC1] | <1 | <10 | 2-4 |
| 113 | 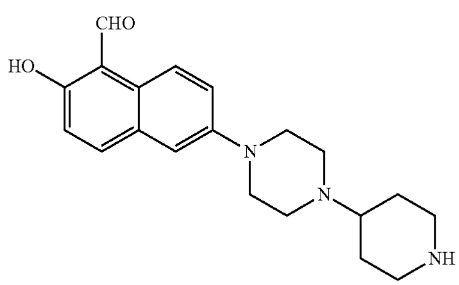 [SMILES: O=Cc1c(O)ccc2cc(N3CCN(C4CCNCC4)CC3)ccc12] | >1 | >10 | 1-15 |
| 114 | 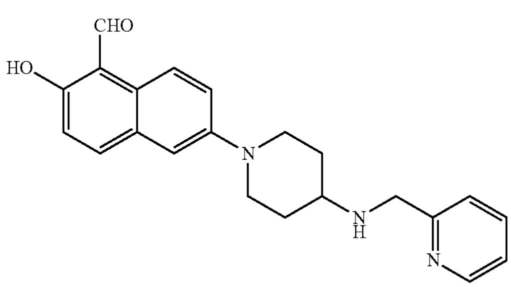 [SMILES: O=Cc1c(O)ccc2cc(N3CCC(NCc4ccccn4)CC3)ccc12] | <1 | >10 | 3-10 |
| 115 | 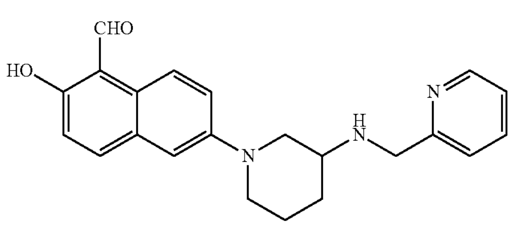 [SMILES: O=Cc1c(O)ccc2cc(N3CCCC(NCc4ccccn4)C3)ccc12] | <1 | >10 | 3-11 |

TABLE 1-continued

| Compound | Structure | IC50_av (μM) | EC50_av (μM) | Synthesis Example |
|---|---|---|---|---|
| 116 | 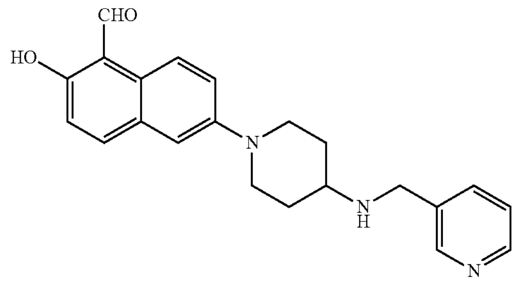 [SMILES: O=Cc1c(O)ccc2cc(N3CCC(NCc4cccnc4)CC3)ccc12] | >1 | <10 | 3-12 |
| 117 | 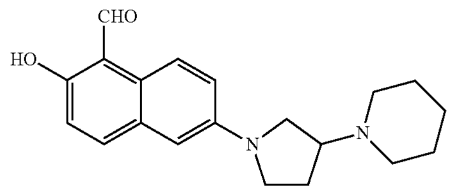 [SMILES: O=Cc1c(O)ccc2cc(N3CCC(N4CCCCC4)C3)ccc12] | <1 | <10 | 3-17 |
| 118 | 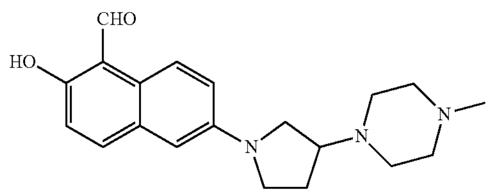 [SMILES: CN1CCN(C2CCN(c3ccc4c(C=O)c(O)ccc4c3)C2)CC1] | >1 | <10 | 3-18 |
| 119 | 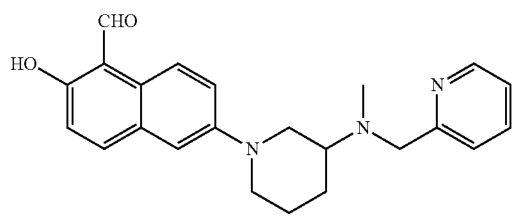 [SMILES: CN(Cc1ccccn1)C1CCCN(c2ccc3c(C=O)c(O)ccc3c2)C1] | >1 | >10 | 3-19 |
| 120 | 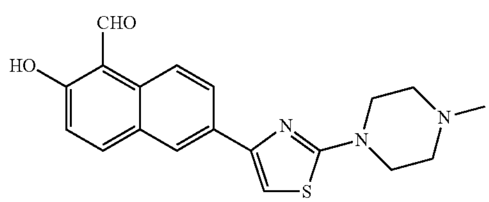 [SMILES: CN1CCN(c2nc(-c3ccc4c(C=O)c(O)ccc4c3)cs2)CC1] | <1 | 10 | 20-4 |
| 121 | 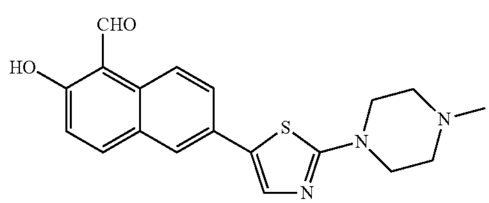 [SMILES: CN1CCN(c2ncc(-c3ccc4c(C=O)c(O)ccc4c3)s2)CC1] | <0.1 | <10 | 20-1 |
| 122 | 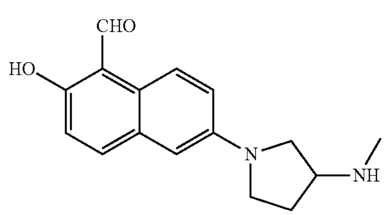 [SMILES: CNC1CCN(c2ccc3c(C=O)c(O)ccc3c2)C1] | >1 | <10 | 5-1 |

TABLE 1-continued

| Compound | Structure | IC50_av (μM) | EC50_av (μM) | Synthesis Example |
|---|---|---|---|---|
| 123 | 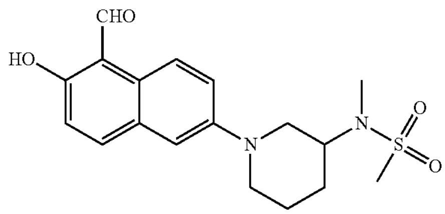 [SMILES: CN(C1CCCN(c2ccc3c(C=O)c(O)ccc3c2)C1)S(C)(=O)=O] | <1 | nd | 4-5 |
| 124 | 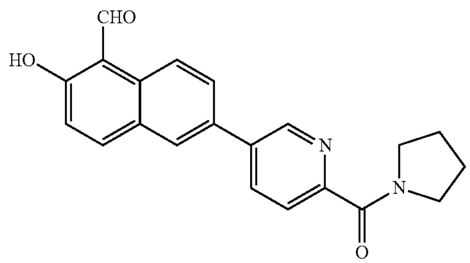 [SMILES: O=Cc1c(O)ccc2cc(-c3ccc(C(=O)N4CCCC4)nc3)ccc12] | <1 | <10 | 12-20 |
| 125 | 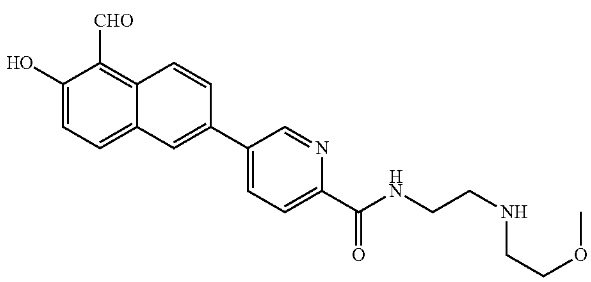 [SMILES: COCCNCCNC(=O)c1ccc(-c2ccc3c(C=O)c(O)ccc3c2)cn1] | <0.1 | <10 | 12-11 |
| 126 | 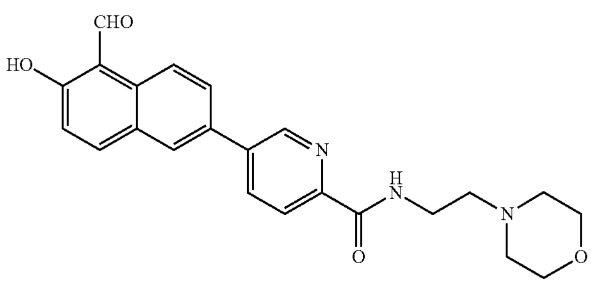 [SMILES: O=Cc1c(O)ccc2cc(-c3ccc(C(=O)NCCN4CCOCC4)nc3)ccc12] | <0.1 | <10 | 12-12 |
| 127 | 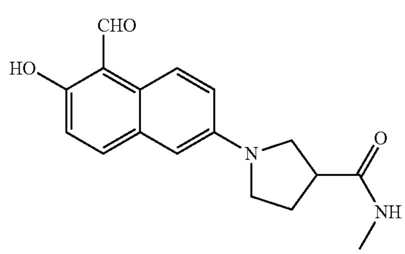 [SMILES: CNC(=O)C1CCN(c2ccc3c(C=O)c(O)ccc3c2)C1] | <1 | >10 | 2-5 |
| 128 | 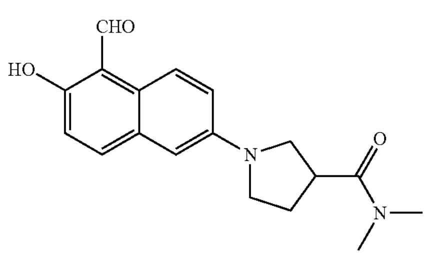 [SMILES: CN(C)C(=O)C1CCN(c2ccc3c(C=O)c(O)ccc3c2)C1] | >1 | >10 | 2-6 |

TABLE 1-continued
| Compound | Structure | IC50_av (μM) | EC50_av (μM) | Synthesis Example |
|---|---|---|---|---|
| 129 | 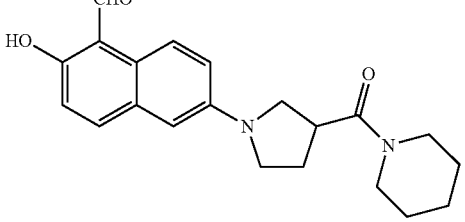 | >1 | >10 | 2-7 |
| 130 | 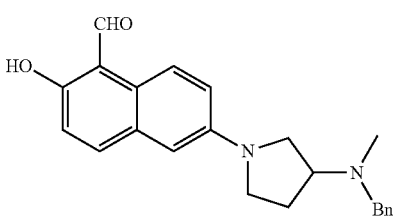 [SMILES: CN(Cc1ccccc1)C1CCN(c2ccc3c(C=O)c(O)ccc3c2)C1] | >1 | >10 | 2-8 |
| 131 | 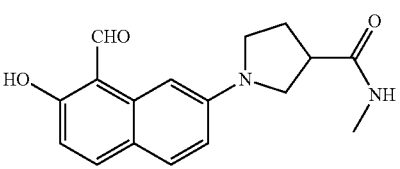 [SMILES: CNC(=O)C1CCN(c2ccc3ccc(O)c(C=O)c3c2)C1] | >1 | >10 | 2-9 |
| 132 | 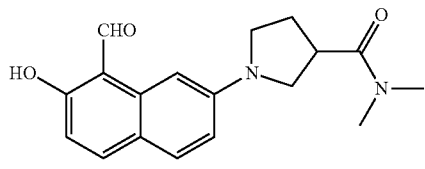 [SMILES: CN(C)C(=O)C1CCN(c2ccc3ccc(O)c(C=O)c3c2)C1] | >1 | >10 | 2-10 |
| 133 | 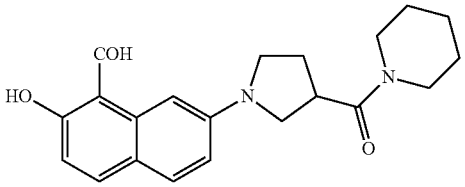 | >1 | >10 | 2-11 |
| 134 | 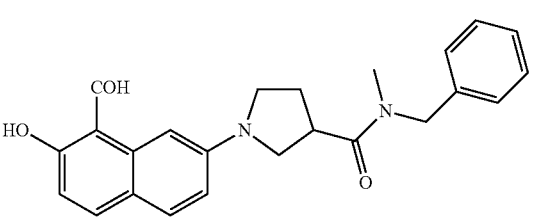 | >1 | >10 | 2-12 |
| 135 | 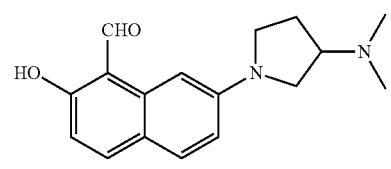 [SMILES: CN(C)C1CCN(c2ccc3ccc(O)c(C=O)c3c2)C1] | >1 | >10 | 1-16 |
| 136 | 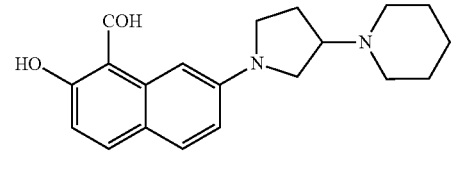 | >1 | >10 | 1-17 |

TABLE 1-continued

| Compound | Structure | IC50_av (µM) | EC50_av (µM) | Synthesis Example |
|---|---|---|---|---|
| 137 | 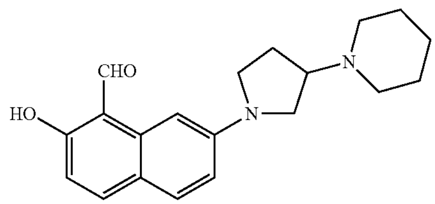 [SMILES: O=Cc1c(O)ccc2ccc(N3CCC(N4CCCCC4)C3)cc12] | >1 | >10 | 1-18 |
| 138 | 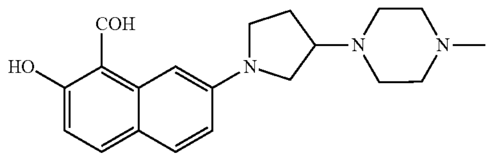 | >1 | >10 | 3-13 |
| 139 | 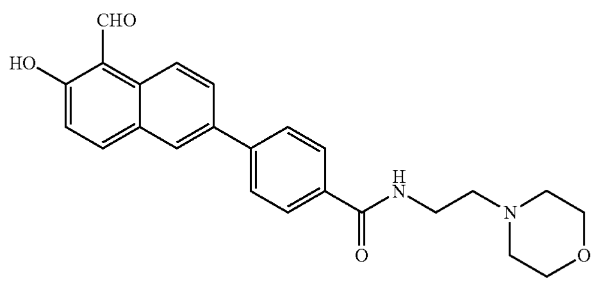 [SMILES: O=Cc1c(O)ccc2cc(-c3ccc(C(=O)NCCN4CCOCC4)cc3)ccc12] | <0.1 | <10 | 12-7 |
| 140 | 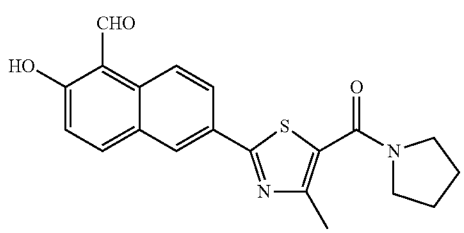 [SMILES: Cc1nc(-c2ccc3c(C=O)c(O)ccc3c2)sc1C(=O)N1CCCC1] | <0.1 | <10 | 12-13 |
| 141 | 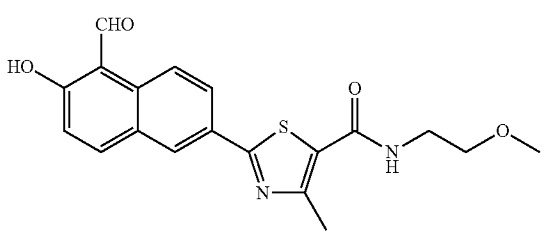 [SMILES: COCCNC(=O)c1sc(-c2ccc3c(C=O)c(O)ccc3c2)nc1C] | <0.1 | <10 | 12-14 |
| 142 | 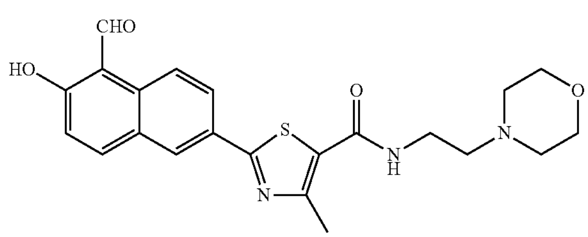 [SMILES: Cc1nc(-c2ccc3c(C=O)c(O)ccc3c2)sc1C(=O)NCCN1CCOCC1] | <0.1 | <10 | 12-15 |

TABLE 1-continued

| Compound | Structure | IC50_av (μM) | EC50_av (μM) | Synthesis Example |
|---|---|---|---|---|
| 143 | 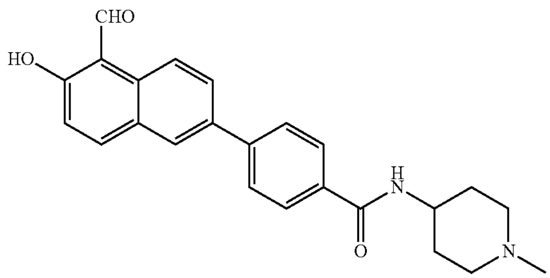 [SMILES: CN1CCC(NC(=O)c2ccc(-c3ccc4c(C=O)c(O)ccc4c3)cc2)CC1] | >1 | <10 | 13-5 |
| 144 | 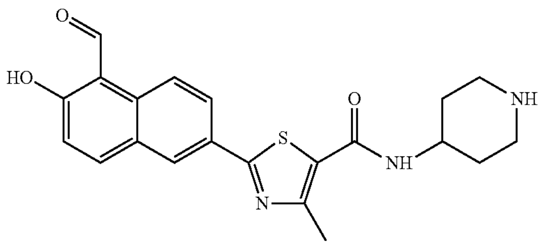 [SMILES: Cc1nc(-c2ccc3c(C=O)c(O)ccc3c2)sc1C(=O)NC1CCNCC1] | <0.1 | <10 | 14-1 |
| 145 | 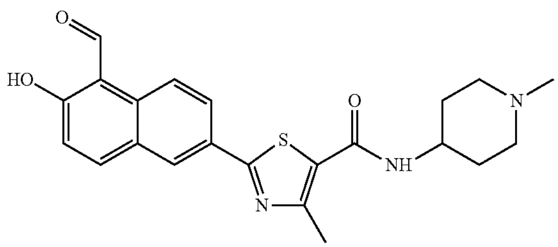 [SMILES: Cc1nc(-c2ccc3c(C=O)c(O)ccc3c2)sc1C(=O)NC1CCN(C)CC1] | <1 | <10 | 13-1 |
| 146 | 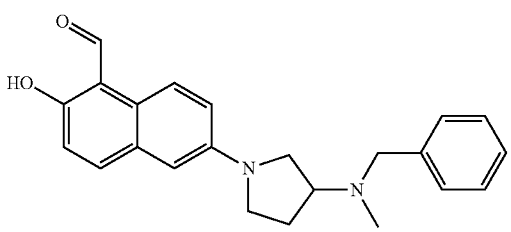 [SMILES: CN(Cc1ccccc1)C1CCN(c2ccc3c(C=O)c(O)ccc3c2)C1] | >1 | >10 | 3-20 |
| 147 | 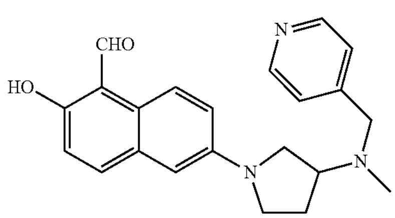 [SMILES: CN(Cc1ccncc1)C1CCN(c2ccc3c(C=O)c(O)ccc3c2)C1] | >1 | >10 | 3-21 |
| 148 | 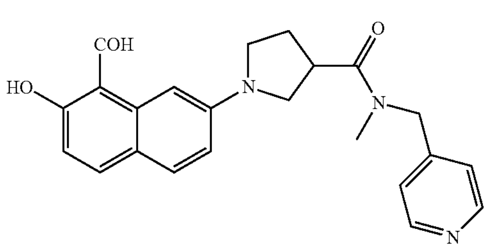 | >1 | >10 | 3-14 |

TABLE 1-continued

| Compound | Structure | IC50_av (μM) | EC50_av (μM) | Synthesis Example |
|---|---|---|---|---|
| 149 | 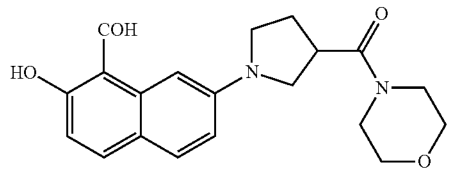 | >1 | >10 | 2-13 |
| 150 | 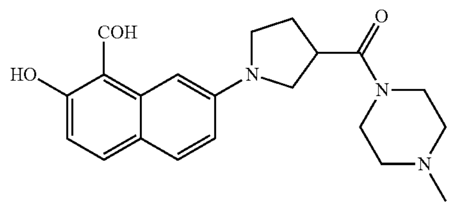 | >1 | >10 | 2-14 |
| 151 | 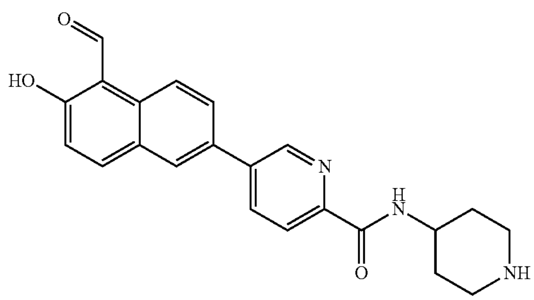 [SMILES: O=Cc1c(O)ccc2cc(-c3ccc(C(=O)NC4CCNCC4)nc3)ccc12] | <1 | <10 | 14-13 |
| 152 | 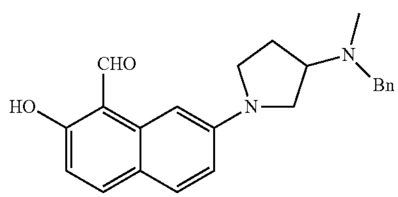 [SMILES: CN(Cc1ccccc1)C1CCN(c2ccc3ccc(O)c(C=O)c3c2)C1] | >1 | >10 | 3-22 |
| 153 | 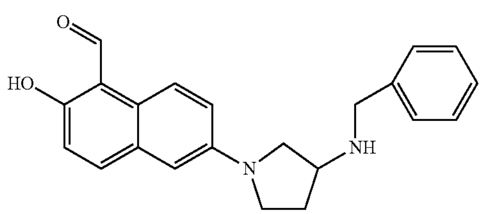 [SMILES: O=Cc1c(O)ccc2cc(N3CCC(NCc4ccccc4)C3)ccc12] | >1 | >10 | 3-15 |
| 154 | 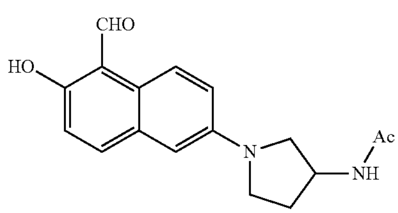 [SMILES: CC(=O)NC1CCN(c2ccc3c(C=O)c(O)ccc3c2)C1] | <1 | <10 | 6-1 |
| 155 | 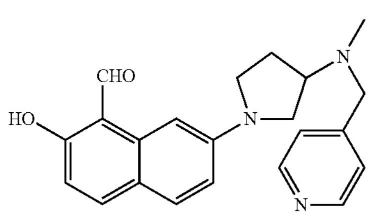 [SMILES: CN(Cc1ccncc1)C1CCN(c2ccc3ccc(O)c(C=O)c3c2)C1] | >1 | >10 | 3-24 |

TABLE 1-continued

| Compound | Structure | IC50_av (μM) | EC50_av (μM) | Synthesis Example |
|---|---|---|---|---|
| 156 | 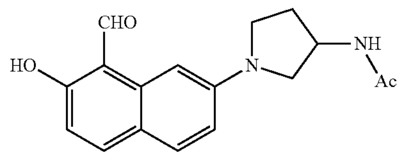 [SMILES: CC(=O)NC1CCN(c2ccc3ccc(O)c(C=O)c3c2)C1] | >1 | >10 | 1-19 |
| 157 | 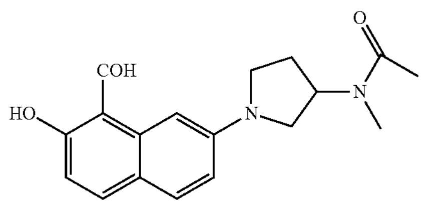 | >1 | >10 | 1-20 |
| 158 | 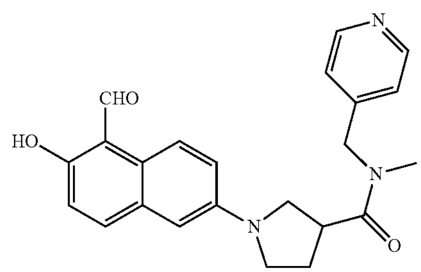 [SMILES: CN(Cc1ccncc1)C(=O)C1CCN(c2ccc3c(C=O)c(O)ccc3c2)C1] | <1 | >10 | 3-16 |
| 159 | 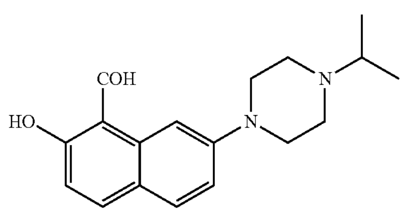 | >1 | >10 | 1-21 |
| 160 | 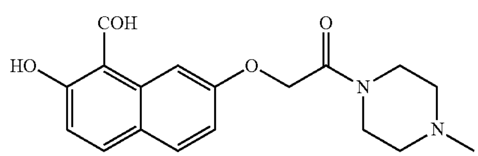 | >1 | >10 | 10-1 |
| 161 | 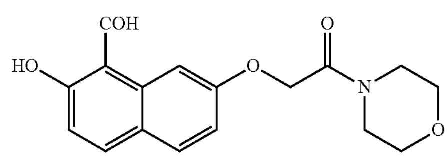 | >1 | >10 | 9-1 |
| 162 | 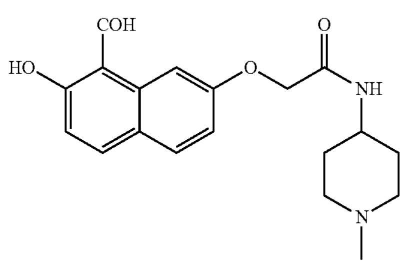 | >1 | >10 | 9-2 |

TABLE 1-continued

| Compound | Structure | IC50_av (μM) | EC50_av (μM) | Synthesis Example |
|---|---|---|---|---|
| 163 | 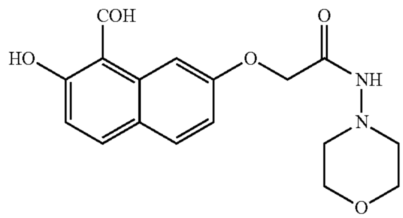 | >1 | >10 | 9-3 |
| 164 | 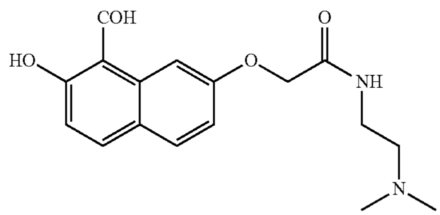 | >1 | >10 | 9-4 |
| 165 | 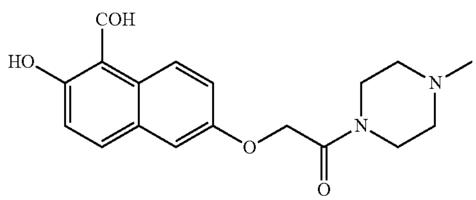 | >1 | >10 | 9-5 |
| 166 | 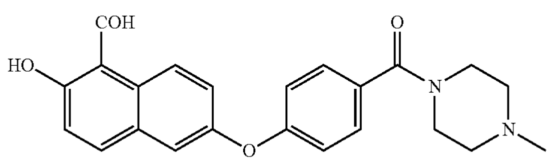 | <1 | <10 | 11-1 |
| 167 | 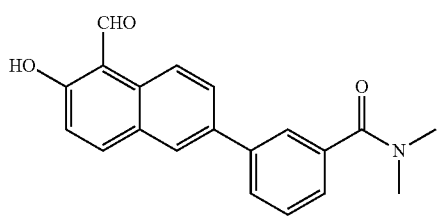 [SMILES: CN(C)C(=O)c1cccc(-c2ccc3c(C=O)c(O)ccc3c2)c1] | <1 | <10 | 19-38 |
| 168 | 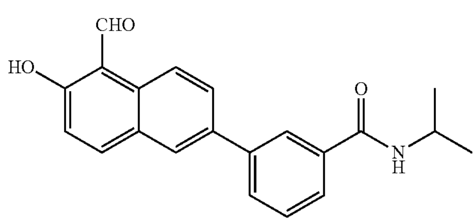 [SMILES: CC(C)NC(=O)c1cccc(-c2ccc3c(C=O)c(O)ccc3c2)c1] | <1 | >10 | 19-39 |
| 169 | 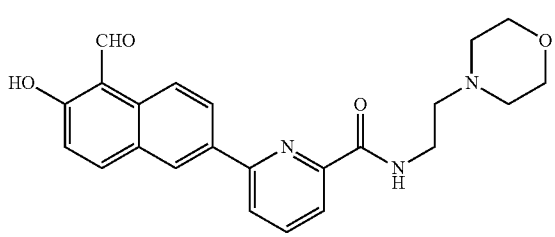 [SMILES: O=Cc1c(O)ccc2cc(-c3cccc(C(=O)NCCN4CCOCC4)n3)ccc12] | <0.1 | <10 | 19-40 |

TABLE 1-continued

| Compound | Structure | IC50_av (μM) | EC50_av (μM) | Synthesis Example |
|---|---|---|---|---|
| 170 | 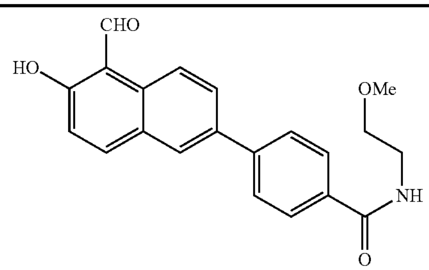 | >1 | <10 | 19-41 |
| 171 | 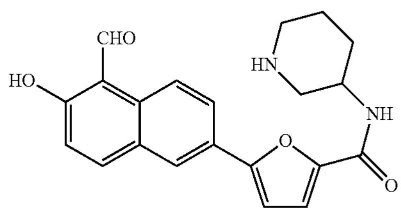 | <0.1 | <10 | 19-42 |
| 172 | 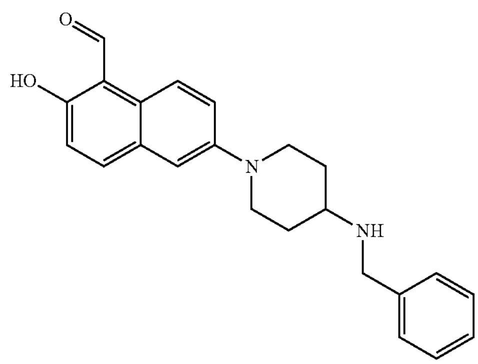 [SMILES: O=Cc1c(O)ccc2cc(N3CCC(NCc4ccccc4)CC3)ccc12] | <1 | >10 | 3-2 |
| 173 | 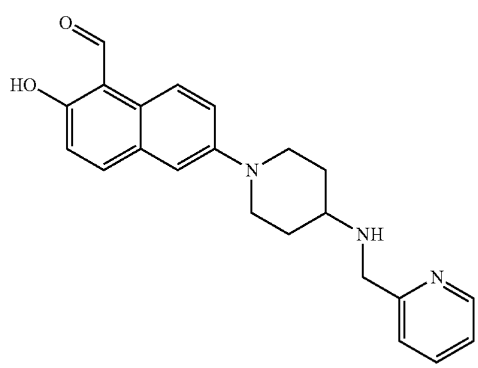 [SMILES: O=Cc1c(O)ccc2cc(N3CCC(NCc4ccccn4)CC3)ccc12] | <1 | >10 | 3-6 |
| 174 | 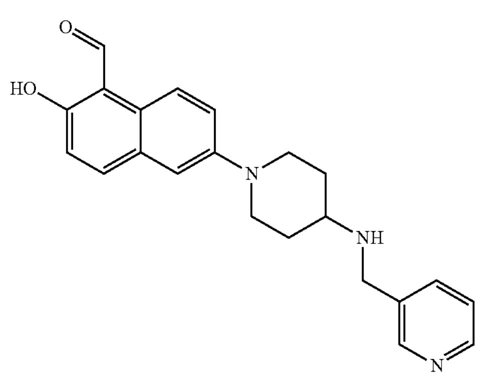 [SMILES: O=Cc1c(O)ccc2cc(N3CCC(NCc4cccnc4)CC3)ccc12] | >1 | <10 | 3-9 |

TABLE 1-continued

| Compound | Structure | IC50_av (μM) | EC50_av (μM) | Synthesis Example |
|---|---|---|---|---|
| 175 | 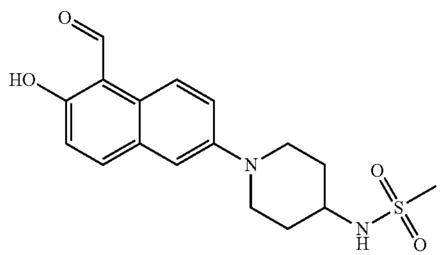 [SMILES: CS(=O)(=O)NC1CCN(c2ccc3c(C=O)c(O)ccc3c2)CC1] | >1 | <10 | 4-2 |
| 176 | 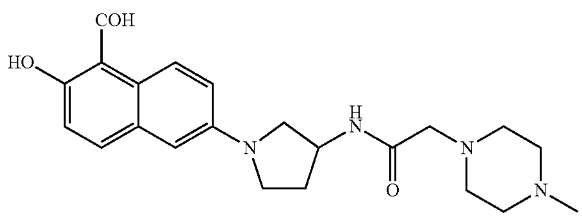 | >1 | >10 | 6-2 |
| 177 | 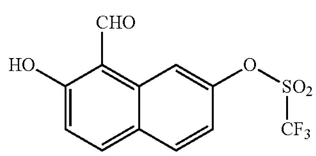 [SMILES: O=Cc1c(O)ccc2ccc(OS(=O)(=O)C(F)(F)F)cc12] | <1 | >10 | 7-1 |
| 178 | 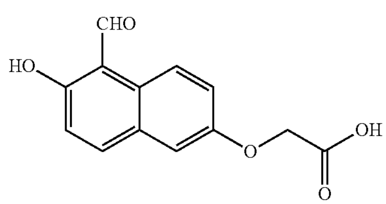 [SMILES: O=Cc1c(O)ccc2cc(OCC(=O)O)ccc12] | >1 | >10 | 8-1 |
| 179 | 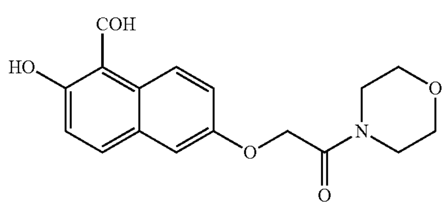 | >1 | >10 | 9-6 |
| 180 | 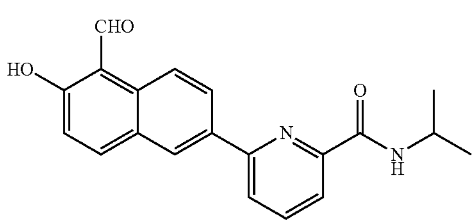 [SMILES: CC(C)NC(=O)c1cccc(-c2ccc3c(C=O)c(O)ccc3c2)n1] | <0.1 | <10 | 19-43 |
| 181 | 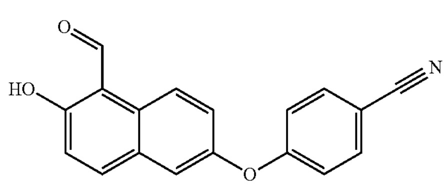 [SMILES: N#Cc1ccc(Oc2ccc3c(C=O)c(O)ccc3c2)cc1] | <1 | <10 | 11b |

TABLE 1-continued

| Compound | Structure | IC50_av (μM) | EC50_av (μM) | Synthesis Example |
|---|---|---|---|---|
| 182 | 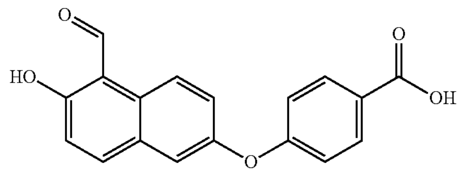 [SMILES: O=Cc1c(O)ccc2cc(Oc3ccc(C(=O)O)cc3)ccc12] | <0.1 | <10 | 11c |

Pharmaceutically Acceptable Salts; Stereoisomers; Tautomers

IRE-1α inhibitor compounds include both the free form of the compounds and the pharmaceutically acceptable salts and stereoisomers thereof. Some of the specific IRE-1α inhibitor compounds described herein are the protonated salts of amine compounds. The term "free form" refers to the amine compounds in non-salt form. The encompassed pharmaceutically acceptable salts not only include the salts described for the specific compounds disclosed herein, but also all the typical pharmaceutically acceptable salts of the free form of IRE-1α inhibitor compounds of the invention and prodrugs thereof.

The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the disclosed IRE-1α inhibitor compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Pharmaceutically acceptable salts of IRE-1α inhibitor compounds include the conventional non-toxic salts of the compounds as formed by reacting a basic compound with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, benzenesulfonic, methanesulfonic, ethane disulfonic, oxalic, isethionic, trifluoroacetic and the like.

When an IRE-1α inhibitor compound is acidic, suitable pharmaceutically acceptable salts include salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particular salts are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N1-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like. The preparation of the pharmaceutically acceptable salts described above and other typical pharmaceutically acceptable salts is more fully described by Berg et al., "Pharmaceutical Salts," *J. Pharm. Sci.,* 1977: 66:1-19.

Some IRE-1α compounds or prodrugs are potentially internal salts or zwitterions, because under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

IRE-1α inhibitor compounds or prodrugs thereof may have asymmetric centers, chiral axes, and chiral planes (as described in: E. L. Eliel and S. H. Wilen, Stereochemistry of Carbon Compounds, John Wiley & Sons, New York, 1994, pages 1119-1190), and may occur as racemates, racemic mixtures, and as individual diastereomers, with all possible isomers and mixtures thereof, including optical isomers, being included in the present invention.

An IRE-1α inhibitor compound or prodrug thereof may be of such a nature that its constituent atoms are capable of being arranged spatially in two or more ways, despite having identical bonds. As a consequence, this compound exists in the form of stereoisomers. Cis/trans isomerism is only one type of stereoisomerism. If the stereoisomers are image and mirror image which cannot be superimposed, they are enantiomers which have chirality or handedness since one or more asymmetric carbon atoms are present in the structure forming them. Enantiomers are optically active and therefore distinguishable since they rotate the plane of polarized light to an equal extent, but in opposite directions.

If two or more asymmetric carbon atoms are present in an IRE-1α compound, two possible configurations exist at each of these carbon atoms. If two asymmetric carbon atoms are present, four possible stereoisomers exist, for example. Furthermore, these four possible stereoisomers can be divided into six possible pairs of stereoisomers that differ from each other. In order for a pair of molecules with more than one asymmetric carbon to be enantiomers, they must have different configurations at each asymmetric carbon. Those pairs that do not behave as enantiomers have a different stereochemical relationship, which is known as a diastereomeric relationship. Stereoisomers that are not enantiomers are known as diastereoisomers, or, more frequently, diastereomers.

All of these well-known aspects of the stereochemistry of the compounds of the invention are considered to be part of the present invention. The present invention therefore covers IRE-1α inhibitor compounds which are stereoisomers, and, if these are enantiomers, the individual enantiomers, racemic mixtures of these enantiomers, and artificial, i.e. synthetic, mixtures comprising proportions of these enantiomers which are different from the proportions of these enantiomers observed in a racemic mixture. If an IRE-1α inhibitor compound has stereoisomers that are diastereomers, this compound includes the individual diastereomers as well as mixtures of any two or more of these diastereomers in any desired proportions.

The following is intended to serve for explanation: if a single asymmetric carbon atom exists in an IRE-1α inhibitor compound that results in the (−)(R) and (+)(S) enantiomers thereof, this an IRE-1α inhibitor compound includes all pharmaceutically acceptable salt forms, prodrugs and metabolites thereof which are therapeutically active and useful for the treatment of or preventing the diseases and conditions described further herein. If an IRE-1α inhibitor compound exists in the form of (−)(R) and (+)(S) enantiomers, this compound also includes the (+)(S) enantiomer alone or the (−)(R) enantiomer alone if all, substantially all or a predominant share of the therapeutic activity resides in only one of these enantiomers or undesired side effects reside in only one of these enantiomers. If essentially no difference exists between the biological properties of the two enantiomers, this compound of the invention furthermore includes the (+)(S) enantiomer and the (−)(R) enantiomer together as a racemic mixture or non-racemic mixture in any desired ratio of corresponding proportions.

The specific biological effects and/or physical and chemical properties of a pair or set of enantiomers of an IRE-1α inhibitor compound—if present—may make it obvious to use these enantiomers in certain ratios, for example to form a final therapeutic product. The following is intended to serve for illustration: if a pair of enantiomers exists, the enantiomers can be used in ratios such as 90% (R)-10% (S), 80% (R)-20% (S), 70% (R)-30% (S), 60% (R)-40% (S), 50% (R)-50% (S), 40% (R)-60% (S), 30% (R)-70% (S), 20% (R)-80% (S), and 10% (R)-90% (S). After evaluation of the properties of the various enantiomers of an IRE-1α inhibitor compound—if they exist—the corresponding amount of one or more of these enantiomers having certain desired properties which form the final therapeutic product can be determined in a simple manner.

For IRE-1α inhibitor compounds disclosed herein which may exist as tautomers, both tautomeric forms are encompassed within the invention, even though only one tautomeric structure is depicted. For example, a compound such as that below drawn as the keto tautomer includes the enol tautomer, and vice versa, as well as mixtures thereof.

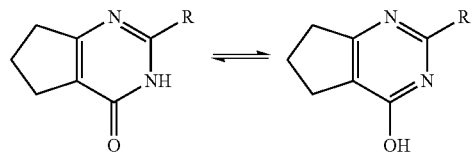

The invention also includes pharmaceutically usable stereoisomers, E/Z isomers, enantiomers, racemates, diastereomers, hydrates, and solvates of the disclosed compounds. "Solvates" are adductions of inert solvent molecules onto the compounds which form owing to their mutual attractive force. Solvates are, for example, monohydrates, dihydrates or alcoholates.

Prodrugs

The invention also provides prodrugs which are metabolized to active IRE-1α inhibitor compounds after administration. For example, IRE-1α inhibitor compounds disclosed herein can be modified, for example, with alkyl or acyl groups, sugars, or oligopeptides and which are rapidly cleaved in vivo to release the active IRE-1α inhibitor compounds.

Derivatives of the corresponding aromatic alcohols can serve as prodrugs for aromatic aldehydes because alcohols and aldehydes are metabolically interconvertible, according to the following general scheme:

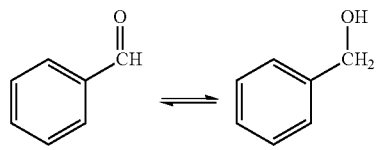 [SMILES: O=Cc1ccccc1 ; OCc1ccccc1]

Scheline, 1972, *Xenobiotica*, 2, 227-36.

Examples of prodrugs of aldehydes, ketones, alcohols and other functional groups are described in Wermuth et al., 1996, *Designing Prodrugs and Bioprecursors I: Carrier Prodrugs. In The Practice of Medicinal Chemistry*, pp. 672-696; and in Wermuth, 1996, "Preparation of Water-Soluble Compounds by Covalent Attachment of Solubilizing Moieties," in Wermuth, ed., *The Practice of Medicinal Chemistry*, pp. 756-776. Other general aldehyde derivatives and alcohol derivatives that can perform prodrug functions as well as methods for their preparation are described in Cheronis et al., 1965, *Semimicro Qualitative Organic Analysis*, New York: Interscience, pp. 465-518.

Methods of Preparing IRE-1α Inhibitor Compounds and Prodrugs of the Invention

IRE-1α inhibitor compounds and starting materials for their synthesis can be prepared by appropriate modification of methods known in the art as described in the literature, for example in standard works such as Houben-Weyl, Methoden der organischen Chemie, Georg-Thieme-Verlag, Stuttgart. Methods may also be found by computer search in The MDL® CrossFire Beilstein database, in which the reaction domain details the preparation of substances. See also the specific Examples, below.

Pharmaceutical Preparations

Any of the IRE-1α inhibitor compounds and prodrugs disclosed herein can be formulated as pharmaceuticals using methods well known in the art. Pharmaceutical formulations of the invention typically comprise at least one IRE-1α inhibitor compound or prodrug thereof mixed with a carrier, diluted with a diluent, and/or enclosed or encapsulated by an ingestible carrier in the form of a capsule, sachet, cachet, paper, or other container, or by a disposable container such as an ampoule.

A carrier or diluent can be a solid, semi-solid, or liquid material. Some examples of diluents or carriers which can be employed in the pharmaceutical compositions of the present invention are lactose, dextrose, sucrose, sorbitol, mannitol, propylene glycol, liquid paraffin, white soft paraffin, kaolin, microcrystalline cellulose, calcium silicate, silica polyvinylpyrrolidone, cetostearyl alcohol, starch, gum acacia, calcium phosphate, cocoa butter, oil of theobroma, arachis oil, alginates, tragacanth, gelatin, methyl cellulose, polyoxyethylene sorbitan monolaurate, ethyl lactate, propylhydroxybenzoate, sorbitan trioleate, sorbitan sesquioleate, and oleyl alcohol.

Pharmaceutical compositions of the invention can be manufactured by methods well known in the art, including conventional mixing, dissolving, granulating, dragee-making, levigating, emulsifying, encapsulating, entrapping, or lyophilizing processes.

For injection, the IRE-1α inhibitor compounds of the invention can be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art. If desired, any of the IRE-1α inhibitor compounds or prodrugs thereof disclosed herein can be provided in a pyrogen-free pharmaceutically acceptable vehicle.

For oral administration, an IRE-1α inhibitor compound or prodrug thereof can be combined with pharmaceutically acceptable carriers or vehicles which enable the IRE-1α inhibitor compound or prodrug thereof to be formulated as tablets, pills, dragees, capsules, liquids, gels, syrups, slurries, suspensions and the like. Fillers can be used, such as gelatin, sugars (e.g., lactose, sucrose, mannitol, or sorbitol), cellulose preparations (e.g., maize starch, wheat starch, rice starch, potato starch, gum tragacanth, methyl cellulose, hydroxypropylmethyl-cellulose, sodium carboxymethylcellulose), and/or polyvinylpyrrolidone (PVP). If desired, disintegrating agents can be added, such as the cross-linked polyvinyl pyrrolidone, agar, or alginic acid or a salt thereof, such as sodium alginate.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, binders such as starches, and/or lubricants such as talc or magnesium stearate and, optionally, stabilizers. In soft capsules, an IRE-1α inhibitor compound or prodrug thereof can be dissolved or suspended in a suitable liquid, such as fatty oils, liquid paraffin, or liquid polyethylene glycols. In addition, stabilizers can be added. All formulations for oral administration preferably are in dosages suitable for such administration.

For buccal administration, the compositions can take the form of tablets or lozenges formulated in conventional manners.

For administration by inhalation, pharmaceutical preparations of the invention can be delivered in the form of an aerosol sprays from a pressurized pack or a nebulizer, with the use of a suitable propellant, e.g., dichlorodifluoromethane, trichlorofluoromethane, dichlorotetrafluoroethane, carbon dioxide, or other suitable gas. If desired, a valve can be used to deliver a metered amount. Capsules and cartridges of, e.g., gelatin for use in an inhaler or insufflator, can be formulated containing a powder mix of an IRE-1α inhibitor compound or prodrug thereof and a suitable powder base, such as lactose or starch.

IRE-1α inhibitor compounds or prodrugs thereof can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions, or emulsions in oily or aqueous vehicles, and can contain formulatory agents such as suspending, stabilizing, and/or dispersing agents.

Pharmaceutical formulations for parenteral administration include aqueous solutions of an IRE-1α inhibitor compound or prodrug thereof. Additionally, a suspension of an IRE-1α inhibitor compound or prodrug thereof can be prepared as an appropriate oily injection suspension. Suitable lipophilic solvents or vehicles include fatty oils such as sesame oil, synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of an IRE-1α inhibitor compound or prodrug thereof to allow for the preparation of highly concentrated solutions.

Alternatively, an IRE-1α inhibitor compound or prodrug thereof can be in powder form for constitution with a suitable vehicle, e.g., sterile pyrogen-free water, before use.

IRE-1α inhibitor compounds or prodrugs thereof can also be formulated in rectal compositions such as suppositories or retention enemas, e.g., containing conventional suppository bases such as cocoa butter or other glycerides.

In addition to the formulations described previously, an IRE-1α inhibitor compound or prodrug thereof can also be formulated as a depot preparation. Such long-acting formulations can be administered by implantation (for example, subcutaneously or intramuscularly) or by intramuscular injection. Thus, for example, an IRE-1α inhibitor compound or prodrug thereof can be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also can comprise suitable solid or gel phase carriers or excipients. Examples of such carriers or excipients include but are not limited to, calcium carbonate, calcium phosphate, various sugars, starches, cellulose derivatives, gelatin, and polymers such as polyethylene glycols.

In addition to the common dosage forms set out above, an IRE-1α inhibitor compound or prodrug thereof can be administered by a controlled release means and/or delivery device, including ALZET® osmotic pumps (Alza Corporation). Suitable delivery devices are described in U.S. Pat. Nos. 3,845,770; 3,916,899; 3,536,809; 3,598,123; 3,944,064; and 4,008,719.

Therapeutic Methods

IRE-1α inhibitor compounds or prodrugs thereof can be administered to a patient, preferably a human patient, in pharmaceutical preparations as disclosed above, preferably with a pyrogen-free pharmaceutically acceptable vehicle, at doses effective to treat or ameliorate a symptom of a disorder associated with the unfolded protein response.

Disorders Associated with UPR

A fine balance exists between a cell's life and death depending on how protein folding stress is managed by the cell (proteostasis). Imbalances in proteostasis lead to many metabolic, oncological, neurodegenerative, inflammatory, cardiovascular disorders and infectious disease (Balch et al., Science 319, 916, 2008). The UPR relates specifically to the proteostasis of the endoplasmic reticulum where all secreted and membrane proteins are translated, folded and processed for delivery to their individual site of action. Therefore, activation of the UPR enhances protein folding in the ER allowing the cell to survive. If protein folding stress is not managed in the ER, the cells will initiate apoptosis.

Protein folding stress may be a natural hallmark of the type of cell for example insulin secreting β-islet cells or antibody secreting plasma cells. In both cases, the cell has fine tuned the machinery to deal with the stress by activating the UPR. Depending on the disease type, it may be therapeutically beneficial to induce or inhibit the UPR. For example, in type II diabetes or Alzheimer's disease, it may be therapeutically beneficial to activate the UPR in such a way where β-islet cells survive the stress of over producing insulin or neurons survive the apoptotic effects due to unfolded aggregates of β-amyloid protein. Diseases such as cancer, inflammation, and viral infection may be therapeutically modulated by inhibition of the UPR. In these types of conditions, cellular survival due to corruption of the UPR may be impacted. Protein folding in the ER is negatively impacted by such conditions in the tumor microenvironment as hypoxia, glucose starvation, amino acid deprivation, acidosis and mutant malfolded and oncgenic proteins. Additionally chemo-, bio-, and radiotherapy can lead to protein folding stress. It may be possible to induce apoptosis in these conditions by inhibiting the anti-apoptotic effects of the UPR. Myeloma derived from neoplastic antibody secreting plasma cells provides an example of a condition in which this approach can be applied.

Lastly, enveloped viruses must use and corrupt this system to ensure production of progeny from infected cells. Viruses often produce vast quantities of viral membrane glycoproteins which are folded and modified in the ER. Therefore, activation of the UPR by the virus for this purpose as a survival mechanism is entirely conceivable. It is therefore logical that inhibition of the UPR during viral infection can impact the outcome of the disease in a beneficial way.

Only specialized secretory cells and diseased cells activate the UPR for their own benefit. Most cells are not under such protein folding stress and therefore would not be impacted by a UPR inhibitor. Thus, "disorders associated with the UPR" as used herein means conditions for which pathogenesis can be advantageously impacted by inhibition of the UPR. In various embodiments of the invention such inhibition of the UPR is accomplished through inhibition of IRE-1α.

In some embodiments the IRE-1α inhibitor compounds or prodrugs thereof are useful to treat or ameliorate a symptom of a B cell autoimmune disease, certain cancers, and infections of enveloped viruses that use the endoplasmic reticulum as a viral factory for expressing viral surface and spike proteins for budding and infection. IRE-1α inhibitors and prodrugs thereof can be used as single agents or in combination therapies, as described below.

B cell autoimmune diseases which can be treated include, but are not limited to, Addison's disease, antiphospholipid syndrome, aplastic anemia, autoimmune hemolytic anemias, autoimmune hepatitis, autoimmune hypophysitis, autoimmune lymphoproliferative disorders, autoimmune myocarditis, Churg-Strauss syndrome, epidermolysis bullosa acquisita, giant cell arteritis, Goodpasture's syndrome, Graves' disease, Guillain-Barré syndrome, Hashimoto's thyroiditis, idiopathic thrombocytopenic purpura, IgA nephropathy, myasthenia gravis, pemphigus foliaceous, pemphigus vulgaris, polyarteritis nodosa, polymyositis/dermatomyositis, rheumatoid arthritis, scleroderma, Sjögren's syndrome, systemic lupus erythematosus, Takayasu's arteritis, and Wegener's granulomatosis.

Cancers which can be treated include solid tumors, such as tumors of the breast, bone, prostate, lung, adrenal gland (e.g., adrenocortical tumors), bile duct, bladder, bronchus, nervous tissue (including neuronal and glial tumors), gall bladder, stomach, salivary gland, esophagus, small intestine, cervix, colon, rectum, liver, ovary, pancreas, pituitary adenomas, and secretory adenomas. Methods of the invention are particularly useful for treating drug- or radiation-resistant solid tumors.

Cancers of the blood (e.g., lymphomas and leukemias) also can be treated including, but not limited to, multiple myeloma, Hodgkin's lymphoma, non-Hodgkin's lymphomas (e.g., cutaneous T cell lymphomas such as Sezary syndrome and Mycosis fungoides, diffuse large cell lymphoma, HTLV-1 associated T cell lymphoma, nodal peripheral T cell lymphoma, extranodal peripheral T cell lymphoma, central nervous system lymphoma, and AIDS-related lymphoma). Leukemias include acute and chronic types of both lymphocytic and myelogenous leukemia (e.g, acute lymphocytic or lymphoblastic leukemia, acute myelogenous leukemia, acute myeloid leukemia, chronic myelogenous leukemia, chronic lymphocytic leukemia, T cell prolymphocytic leukemia, adult T cell leukemia, and hairy cell leukemia). Monoclonal gammopathy of undetermined significance (MGUS), the precursor of myeloma, also can be treated.

Viral infections which can be treated include infections of enveloped viruses which use the unfolded protein response pathway when they replicate and form infectious progeny (e.g., measles, pox viruses, Ebola, etc.). Infections also include those of Epstein Barr virus (EBV), cytomegalovirus (CMV), Flaviviruses (e.g., Japanese Encephalitis Virus and West Nile Virus), and Hepatitis C virus (HCV).

Combination Therapies

Various types of physiological stress induce the unfolded protein response including, but not limited to, hypoxia, nutrient starvation, acidosis, and genetic damage resulting in mutant or over-expressed misfolded proteins (oncogenic stress). One or more of these conditions are manifest in cancer cells, which may in part be mediated by the microenviroment of the tumor. It is likely the cytoprotective arm of the unfolded protein response (UPR) plays an anti-apototic role in tumor survival. In addition, bio- and chemotherapeutic drugs and radiation treatments may further impact the protein folding and degradation cycle in the ER thereby inducing the UPR as a protective resistance mechanism. Patients succumb to cancer because either the tumor is resistant to conventional therapies or returns in a resistant form after an initial response to treatment and, therefore, new treatments and treatment combinations are needed.

Angiogenesis inhibitors block tumor growth by inhibiting new blood vessel formation, a process that would enhance the stress effects of the tumor microenvironment. A promising approach to further reduce tumor burden would be to administer anti-angiogenesis agents in combination with IRE-1α/XBP-1 inhibitors to obtain a similar effect as that demonstrated by RNAi knockdown of GRP78, the major chaperone of the ER and target of XBP-1s (Dong et al., Cancer Res. 2007 Jul. 15; 67(2):6700-7). In addition, IRE-1α itself regulates angiogensis by influencing the expression of VEGF.

Proteasome inhibitors and Hsp90 inhibitors are thought to act in part by blocking protein degradation and folding, respectively, inducing apoptosis (Davenport et al., Blood 2007 Oct. 1; 110(7):2641-9). Although it is clear that Hsp90 inhibitors induce XBP-1 splicing and activation of the UPR, it is less clear that proteasome inhibitors activate IRE-1α. Current scientific literature suggest that IRE-1α is not or is only minimally activated by proteasome inhibitors, such as bortezomib or MG-132 (Davenport et al., Blood 2007 Oct. 1; 110(7):2641-9).

Interference with UPR may sensitize cancer cells to various chemotherapeutics that elevate the cellular stress. Combination therapies which include IRE-1α inhibitors may become important therapies in conjunction with current and future standard of care in cancer.

Although the level of activation IRE-1α in solid tumors is currently not known, clearly, induction of the UPR in patient biopsies of drug resistant tumors is evidenced by induction of GRP78 (Moenner et al., Cancer Res. 2007 Nov. 15; 67(22):10631-4; Lee, Cancer Res. 2007 Apr. 15; 67(6e): 3496-9).

Inhibition of XBP-1 splicing may have a greater effect than anticipated as the un-spliced form of XBP-1 may act as a dominant negative to XBP-1 and ATF-6 transcriptional activity. Further inhibitors which block the RNAse activity but not kinase activity of IRE-1α may have the added benefit of signaling through the JNK pathway, a signal that can have pro-apoptotic consequences.

In some embodiments an IRE-1α inhibitor compound or prodrug thereof is administered in combination with a therapeutic agent that induces or up-regulates IRE-1α expression (e.g., Hsp90 and or HDAC inhibitors, both of which induce IRE-1α activation and XBP-1 splicing) or a therapeutic agent which is less effective when IRE-1α is expressed (e.g., 17-AAG (TANESPIMYCIN®) and suberoylanilide hydroxamic acid (SAHA)).

In some embodiments an IRE-1α inhibitor compound or prodrug thereof is administered in combination with a cancer therapeutic agent, for example radiation therapy or a cancer therapeutic agent (e.g., a chemotherapeutic agent or a biotherapeutic agent) as described below. The cancer therapeutic agent can be administered separately or together with the IRE-1α inhibitor compound. The cancer therapeutic agent can be administered at essentially the same time as the IRE-1α inhibitor compound or can be administered either before or after the IRE-1α inhibitor compound.

Cancer therapeutic agents which can be used according to the invention include, but are not limited to, agents in the following categories (which may overlap):

a. proteasome inhibitors, such as bortezomib ([(1R)-3-methyl-1-[[(2S)-1-oxo-3-phenyl-2-[(pyrazinylcarbonyl)amino]propyl]amino]butyl] boronic acid; MG-341; VELCADE®), MG-132 (N-[(phenylmethoxy)carbonyl]-L-leucyl-N-[(1S)-1-formyl-3-methylbutyl]-L-leucinamide);

b. antimetabolites, such as:
  i. pyrimidine analogs (e.g., 5-fluorouracil, floxuridine, capecitabine, gemcitabine and cytarabine);
  ii. purine analogs,
  iii. folate antagonists and related inhibitors (e.g., mercaptopurine, thioguanine, pentostatin and 2-chlorodeoxyadenosine [cladribine]);
  iv. folic acid analogs (e.g., methotrexate);

c. antimitotic agents, including:
  i. natural products such as vinca alkaloids (e.g., vinblastine, vincristine, and vinorelbine);
  ii. alkylating agents such as nitrogen mustards (e.g., mechlorethamine, cyclophosphamide and analogs, melphalan, chlorambucil), ethylenimines and methylmelamines (e.g., hexamethylmelamine and thiotepa), alkyl sulfonates-busulfan, nitrosoureas (e.g., carmustine (BCNU) and analogs, streptozocin), trazenes—dacarbazinine (DTIC);

d. microtubule disruptors such as taxane (paclitaxel, docetaxel), vincristin, vinblastin, nocodazole, epothilones and navelbine, and epipidopodophyllotoxins (e.g., teniposide);

e. DNA damaging agents, such as actinomycin, amsacrine, anthracyclines, bleomycin, busulfan, camptothecin, carboplatin, chlorambucil, cisplatin, cyclophosphamide, Cytoxan, dactinomycin, daunorubicin, docetaxel, doxorubicin, epirubicin, hexamethylmelamineoxaliplatin, iphosphamide, melphalan, merchlorethamine, mitomycin, mitoxantrone, nitrosourea, paclitaxel, plicamycin, procarbazine, teniposide, triethylenethiophosphoramide and etoposide (VP 16);

f. antibiotics, such as dactinomycin (actinomycin D), daunorubicin, doxorubicin (adriamycin), idarubicin, anthracyclines, mitoxantrone, bleomycins, plicamycin (mithramycin) and mitomycin;

g. enzymes, such as L-asparaginase;

h. antiplatelet agents;

i. platinum coordination complexes (e.g., cisplatin, carboplatin), procarbazine, hydroxyurea, mitotane, aminoglutethimide;

j. hormones, hormone analogs (e.g., estrogen, tamoxifen, goserelin, bicalutamide, nilutamide);

k. aromatase inhibitors (e.g., letrozole, anastrozole);

l. anticoagulants (e.g., heparin, synthetic heparin salts and other inhibitors of thrombin);

m. fibrinolytic agents (such as tissue plasminogen activator, streptokinase and urokinase), aspirin, COX-2 inhibitors, dipyridamole, ticlopidine, clopidogrel, abciximab;

n. antimigratory agents;

o. antisecretory agents (e.g., breveldin); immunosuppressives (e.g., cyclosporine, tacrolimus (FK-506), sirolimus (rapamycin), azathioprine, mycophenolate mofetil);

p. anti-angiogenic compounds (e.g., TNP-470, genistein) and growth factor inhibitors (e.g., vascular endothelial growth factor (VEGF) inhibitors, fibroblast growth factor (FGF) inhibitors, epidermal growth factor (EGF) inhibitors);

q. angiotensin receptor blockers;

r. nitric oxide donors;

s. anti-sense oligonucleotides;

t. antibodies (e.g., trastuzumab (HERCEPTIN®), AVASTIN®, ERBITUX®);

u. cell cycle inhibitors and differentiation inducers (e.g., tretinoin);

v. mTOR (mammalian target of rapamycin) inhibitors (e.g., everolimus, sirolimus);

w. topoisomerase inhibitors (e.g., doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan);

x. corticosteroids (e.g., cortisone, dexamethasone, hydrocortisone, methylprednisolone, prednisone, and prenisolone);

y. growth factor signal transduction kinase inhibitors;

z. mitochondrial dysfunction inducers;

aa. caspase activators; and bb. chromatin disruptors.

In some embodiments the cancer therapeutic agent is selected from the group consisting of alemtuzumab, aminoglutethimide, amsacrine, anastrozole, asparaginase, beg, bevacizumab, bicalutamide, bleomycin, bortezomib, buserelin, busulfan, campothecin, capecitabine, carboplatin, carmustine, CeaVac, cetuximab, chlorambucil, cisplatin, cladribine, clodronate, colchicine, cyclophosphamide, cyproterone, cytarabine, dacarbazine, daclizumab, dactinomycin, daunorubicin, dienestrol, diethylstilbestrol, docetaxel, doxorubicin, edrecolomab, epirubicin, epratuzumab, erlotinib, estradiol, estramustine, etoposide, exemestane, filgrastim, fludarabine, fludrocortisone, fluorouracil, fluoxymesterone, flutamide, gemcitabine, gemtuzumab, genistein, goserelin, huJ591, hydroxyurea, ibritumomab, idarubicin, ifosfamide, IGN-101, imatinib, interferon, irinotecan, ironotecan, letrozole, leucovorin, leuprolide, levamisole, lintuzumab, lomustine, MDX-210, mechlorethamine, medroxyprogesterone, megestrol, melphalan, mercaptopurine, mesna, methotrexate, mitomycin, mitotane, mitoxantrone, mitumomab, nilutamide, nocodazole, octreotide, oxaliplatin, paclitaxel, pamidronate, pentostatin, pertuzumab, plicamycin, porfimer, procarbazine, raltitrexed, rituximab, streptozocin, sunitinib, suramin, tamoxifen, temozolomide, teniposide, testosterone, thalidomide, thioguanine, thiotepa, titanocene dichloride, topotecan, tositumomab, trastuzumab, tretinoin, vatalanib, vinblastine, vincristine, vindesine, and vinorelbine.

Routes of Administration

Pharmaceutical preparations of the invention can be administered locally or systemically. Suitable routes of administration include oral, pulmonary, rectal, transmucosal, intestinal, parenteral (including intramuscular, subcutaneous, intramedullary routes), intranodal, intrathecal, direct intraventricular, intravenous, intraperitoneal, intranasal, intraocular, transdermal, topical, and vaginal routes. As described in more detail above, dosage forms include, but are not limited to, tablets, troches, dispersions, suspensions, suppositories, solutions, capsules, creams, patches, minipumps and the like. Targeted delivery systems also can be used (for example, a liposome coated with target-specific antibody).

Dosage

A pharmaceutical composition of the invention comprises at least one active ingredient (an IRE-1α inhibitor compound or prodrug thereof) in a therapeutically effective dose. A "therapeutically effective dose" is the amount of an IRE-1α inhibitor compound or prodrug thereof which, when administered to a patient over a treatment period, results in a measurable improvement in a characteristic of the disease being treated (e.g., improved laboratory values, retarded development of a symptom, reduced severity of a symptom, or improved levels of an appropriate biological marker).

Determination of therapeutically effective doses is well within the capability of those skilled in the art. A therapeutically effective dose initially can be estimated from in vitro enzyme assays, cell culture assays, and/or animal models. For example, a dose can be formulated in an animal model to achieve a circulating concentration range at least as concentrated as the $IC_{50}$ as determined in an in vitro enzyme assay or in a cell culture (i.e., the concentration of the test compound which achieves a half-maximal inhibition of IRE-1α activity). Such information can be used to more accurately determine useful doses in humans. See the FDA guidance document "Guidance for Industry and Reviewers Estimating the Safe Starting Dose in Clinical Trials for Therapeutics in Adult Healthy Volunteers" (HFA-305), which provides an equation for use in calculating a human equivalent dose (HED) based on in vivo animal studies.

Appropriate animal models for the relevant diseases are known in the art. See, e.g., Lupus. 1996 Oct.; 5(5b):451-5 (antiphospholipid syndrome); Blood. 1974 July; 44(1):49-56 (aplastic anemia); Autoimmunity. 2001; 33(5):265-74 (autoimmune hypophysitis); Methods. 2007 January; 41(1):118-22 (autoimmune myocarditis); Clin Exp Rheumatol. 2003 Nov.-Dec.; 21(6 Suppl 32):S55-63 (Churg-Strauss syndrome, Wegener's granulomatosis); J Clin Invest. 2005 April; 115(5):870-8 (epidermolysis bullosa acquisita); Circulation. 2005 Jun. 14; 111(23):3135-40. Epub 2005 Jun. 6 (giant cell arteritis; Takayusu's arteritis); Int J Immunopathol Pharmacol. 2005 Oct.-Dec.; 18(5):701-8 (IgA nephropathy); Vet Rec. 1984 May 12; 114(19):479 (pemphigus foliaceous); *J. Neuroimmunol.* 98, 130-35, 1999 (polymyositis); *Am. J. Pathol.* 120, 323-25, 1985 (dermatomyositis); *Cell. Mol. Immunol.* 2, 461-65, 2005 (myasthenia gravis); *Arthritis Rheum.* 50, 3250-59, 2004 (lupus erythymatosus); *Clin. Exp. Immunol.* 99, 294-302, 1995 (Grave's disease); *J. Clin. Invest.* 116, 961-973, 2006 (rheumatoid arthritis); *Exp Mol Pathol.* 77, 161-67, 2004 (Hashimoto's thyroiditis); *Rheumatol.* 32, 1071-75, 2005 (Sjögren's syndrome); *Brain Pathol.* 12, 420-29, 2002 (Guillain-Barré syndrome); *Vet. Pathol.* 32, 337-45, 1995 (polyarteritis nodosa); *Immunol. Invest.* 3, 47-61, 2006 (pemphigus vulgaris); *Arch. Dermatol. Res.* 297, 333-44, 2006 (scleroderma); *J. Exp. Med.* 191, 899-906, 2000 (Goodpasture's syndrome); *Clin. Exp. Immunol.* 99, 294-302, 1995 (Grave's disease); *J. Clin. Invest.* 91, 1507-15, 1993 (membranous nephropathy); *J. Immunol.* 169, 4889-96, 2002 (autoimmune hepatitis); *Surgery* 128, 999-1006, 2000 (Addison's disease); *Eur. J. Immunol.* 32, 1147-56, 2002 (autoimmune hemolytic anemia); and *Haematologica* 88, 679-87, 2003 (autoimmune thrombocytopenic purpura).

$LD_{50}$ (the dose lethal to 50% of the population) and the $ED_{50}$ (the dose therapeutically effective in 50% of the population) can be determined by standard pharmaceutical procedures in cell cultures and/or experimental animals. Data obtained from cell culture assays or animal studies can be used to determine initial human doses. As is known in the art, the dosage may vary depending upon the dosage form and route of administration used.

Usual dosages for systemic administration to a human patient range from 1 µg/kg to 100 mg/kg (e.g., 1-10 µg/kg, 20-80 µg/kg, 5-50 µg/kg, 75-150 µg/kg, 100-500 µg/kg, 250-750 µg/kg, 500-1000 µg/kg, 1-10 mg/kg, 5-50 mg/kg, 25-75 mg/kg, 50-100 mg/kg, 5 mg/kg, 20 mg/kg, or 50 mg/kg). In some embodiments, the treatment schedule can require that a plasma concentration of an IRE-1α inhibitor compound be maintained for a period of time (e.g., several days or a week) and then allowed to decay by ceasing administration for a period of time (e.g., 1, 2, 3, or 4 weeks). The amount of composition administered will, of course, be dependent on the subject being treated, on the subject's weight, the severity of the disorder, the manner of administration and the judgment of the prescribing physician.

All patents, patent applications, and references cited in this disclosure are expressly incorporated herein by reference. The above disclosure generally describes the present invention. A more complete understanding can be obtained by reference to the following specific examples, which are provided for purposes of illustration only and are not intended to limit the scope of the invention.

EXAMPLES

The analytical LC/MS method used in Examples 1-20 employed an Agilent 1200 with Variable Wavelength detector extracted at 220 nm and Agilent 6140 Single quadrupole mass spectrometer. The HPLC column was a Zorbax SB-C18, 3.5 μm, 2.1 mm×30 mm, maintained at 40° C. The HPLC Gradient was 0.4 mL/min, 95:5:0.1 water:acetonitrile:formic acid for 0.1 min then to 5:95:0.1 water:acetonitrile:formic acid in 3.9 min, maintaining for 0.5 min.

Example 1

Synthesis of 2-Hydroxy-6-(4-methyl-piperazin-1-yl)-naphthalene-1-carbaldehyde hydrochloride 1-1

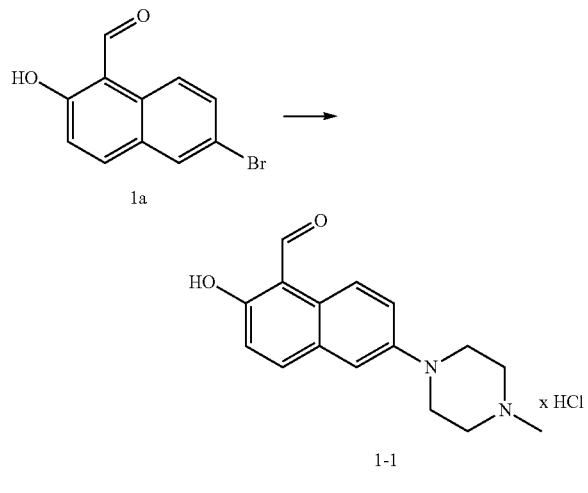

2-Hydroxy-6-(4-methyl-piperazin-1-yl)-naphthalene-1-carbaldehyde 1-1

6-Bromo-2-hydroxy-naphthalene-1-carbaldehyde (1a, WO2008154484) (100 mg, 0.4 mmol), 1-methyl-piperazine (44 mg, 0.44 mmol), sodium tert-butoxide (84 mg, 0.88 mmol), tris-(dibenzylideneacetone)dipalladium(0) (25 mg, 28 mol), (2-biphenyl)di-tert-butylphosphine (18 mg, 26 μmol) were dissolved in 12 mL of dry dioxane. The resulted tan slurry was heated to 100° C. for 1 h. The reaction mixture was evaporated and partitioned between 20 mL of chloroform and 20 mL of water. The pH of the aqueous phase was adjusted to neutral with acetic acid then was separated, and extracted with another 20 mL portion of chloroform. The combined organic phases were dried over sodium sulfate, filtered and evaporated. The resulted solid material was purified by chromatography with chloroform as eluent. The obtained crude product was triturated with diethyl ether to afford 1-1 (50 mg, 19 mmol, 46%).

LC/MS ESI: M+H=271, Rt: 2.70 min; $^1$H NMR (400 MHz, DMSO-d$_6$) δ ppm 11.72 (br. s., 1H), 11.03 (br. s., 1H), 10.76 (s, 1H), 8.85 (d, J=9.3 Hz, 1H), 7.99 (d, J=8.8 Hz, 1H), 7.49 (dd, J=9.4, 2.6 Hz, 1H), 7.32 (d, J=2.8 Hz, 1H), 7.23 (d, J=9.0 Hz, 1H), 3.84-3.97 (m, 2H), 3.45-3.58 (m, 2H), 3.17 (d, J=9.3 Hz, 4H), 2.81 (d, J=4.8 Hz, 3H).

The following compounds were made by the above procedure:

| No. | | MW | M + H | Rt |
|---|---|---|---|---|
| 1-1 | ![structure] | 270.3 | 271 | 2.70 |
| 1-2 | ![structure] | 284.4 | 285 | 2.64 |
| 1-3 | ![structure] | 241.3 | 242 | 4.05 |

-continued
| No. | | MW | M + H | Rt |
|---|---|---|---|---|
| 1-4 | 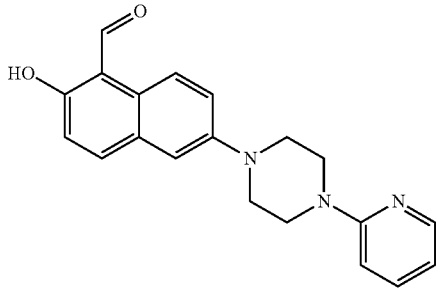 [SMILES: O=Cc1c(O)ccc2cc(N3CCN(c4ccccn4)CC3)ccc12] | 333.4 | 334 | 2.97 |
| 1-5 | 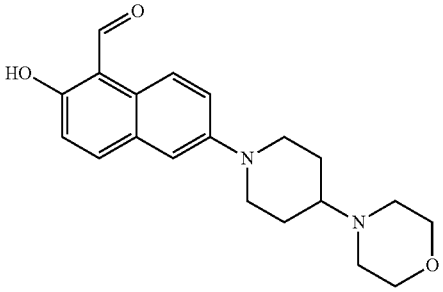 | 340.4 | 341 | 2.69 |
| 1-6 | 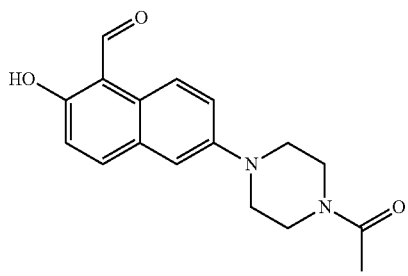 [SMILES: CC(=O)N1CCN(c2ccc3c(C=O)c(O)ccc3c2)CC1] | 298.3 | 299 | 3.23 |
| 1-7 | 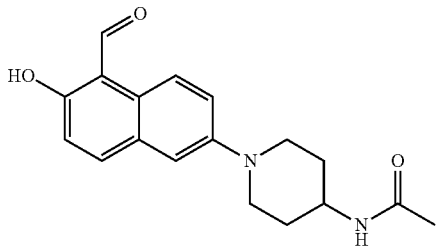 [SMILES: CC(=O)NC1CCN(c2ccc3c(C=O)c(O)ccc3c2)CC1] | 312.4 | 313 | 2.75 |
| 1-8 | 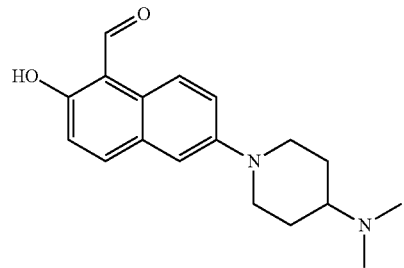 [SMILES: CC(C)N1CCN(c2ccc3c(C=O)c(O)ccc3c2)CC1] | 298.4 | 299 | 2.64 |

-continued

| No. | | MW | M + H | Rt |
|---|---|---|---|---|
| 1-9 | | 353.5 | 354 | 2.43 |
| 1-10 | | 270.3 | 271 | 2.63 |
| 1-11 | | 257.3 | 258 | 3.60 |
| 1-12 | | 353.5 | 354 | 2.55 |
| 1-13 | | 340.4 | 341 | 2.72 |
| 1-14 | | 298.4 | 299 | 2.65 |

-continued

| No. | | MW | M + H | Rt |
|---|---|---|---|---|
| 1-15 | | 339.4 | 340 | 2.01 |
| 1-16 | | 284.4 | 285 | 2.64 |
| 1-17 | | 326.4 | 327 | 2.65 |
| 1-18 | | 324.4 | 325 | 2.83 |
| 1-19 | | 298.3 | 299 | 3.27 |
| 1-20 | | 312.4 | 313 | 3.67 |
| 1-21 | | 298.4 | 299 | 2.67 |

| No. | | MW | M + H | Rt |
|---|---|---|---|---|
| 1-22 | 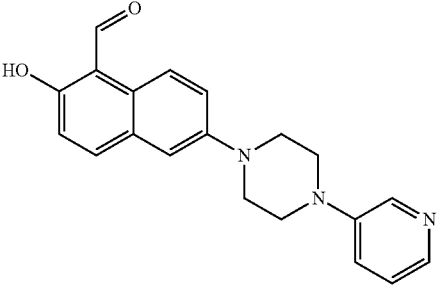 [SMILES: O=Cc1c(O)ccc2cc(N3CCN(c4cccnc4)CC3)ccc12] | 333.4 | 334 | 2.92 |
| 1-23 | 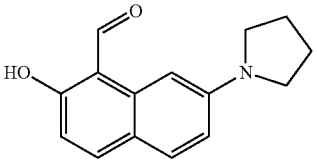 [SMILES: O=Cc1c(O)ccc2ccc(N3CCCC3)cc12] | 241.3 | 242 | 4.24 |
| 1-24 | 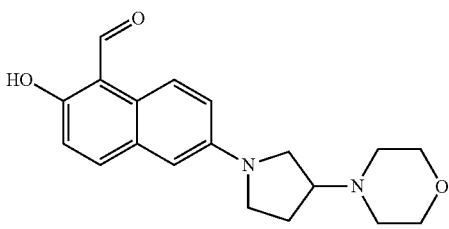 [SMILES: O=Cc1c(O)ccc2cc(N3CCC(N4CCOCC4)C3)ccc12] | 326.4 | 327 | 2.66 |
| 1-25 | 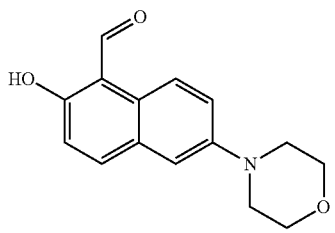 [SMILES: O=Cc1c(O)ccc2cc(N3CCOCC3)ccc12] | 257.3 | 258 | 3.20 |
| 1-26 | 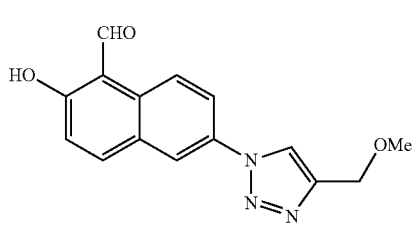 [SMILES: COCc1cn(-c2ccc3c(C=O)c(O)ccc3c2)nn1] | 283.1 | 284 | |

Example 2

Synthesis of 2-Hydroxy-6-[3-(morpholine-4-carbonyl)-pyrrolidin-1-yl]-naphthalene-1-carbaldehyde 2-1

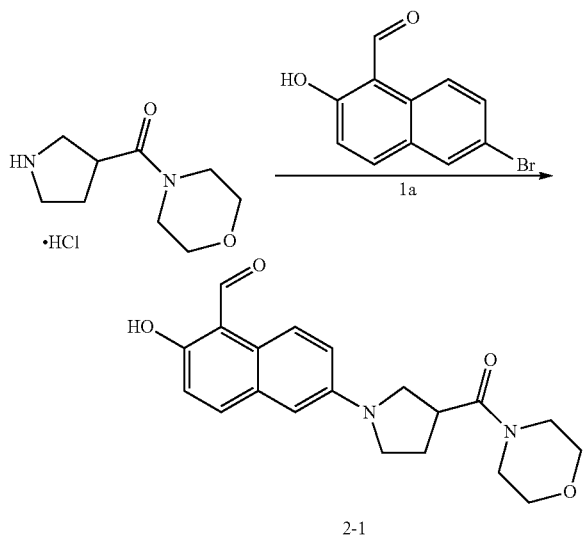

6-Bromo-2-hydroxy-naphthalene-1-carbaldehyde 1a (150 mg, 0.6 mmol), morpholin-4-yl-pyrrolidin-3-yl-methanone (158 mg, 0.72 mmol), sodium-tert-butoxide (207 mg, 2.16 mmol), tris-(dibenzylideneacetone)dipalladium(0) (38 mg, 41 mol), (2-biphenyl)di-tert-butylphosphine (25 mg, 84 μmol) were dissolved in 18 mL of dry dioxane. The resulted tan slurry was heated to 100° C. for 3 h. The reaction mixture was evaporated and partitioned between 30 mL of chloroform and 30 mL of water. The pH of the aqueous phase was adjusted to neutral with acetic acid then was separated, and extracted with another 30 mL portion of chloroform. The combined organic phases were dried over sodium sulfate, filtered and evaporated. The resulted solid material was purified by chromatography with chloroform as eluent. The obtained crude product was triturated with diethyl ether to afford 2-1 (108 mg, 31 mmol, 51%).

LC/MS ESI: M+H=355, Rt: 3.43 min; $^1$H NMR (400 MHz, CDCl$_3$) δ ppm 12.80 (s, 1H), 10.75 (s, 1H), 8.21 (d, J=9.3 Hz, 1H), 7.81 (d, J=9.0 Hz, 1H), 7.08 (dd, J=9.3, 2.5 Hz, 1H), 7.05 (d, J=9.0 Hz, 1H), 6.78 (d, J=2.5 Hz, 1H), 3.58-3.78 (m, 10H), 3.52-3.58 (m, 1H), 3.45-3.51 (m, 1H), 3.35-3.45 (m, 1H), 2.34-2.46 (m, 1H), 2.21-2.33 (m, 1H).

The following compounds were made by the above procedure:

| No. | | MW | M + H | Rt |
|---|---|---|---|---|
| 2-1 | | 354.4 | 355 | 3.43 |
| 2-2 | | 368.4 | 369 | 2.91 |
| 2-3 | | 381.5 | 382 | 2.41 |

| No. | | MW | M + H | Rt |
|---|---|---|---|---|
| 2-4 | (structure) | 367.4 | 368 | 2.81 |
| 2-5 | (structure) | 298.3 | 299 | 3.21 |
| 2-6 | (structure) | 312.4 | 313 | 3.45 |
| 2-7 | (structure) | 352.4 | 353 | 3.92 |
| 2-8 | (structure) | 388.5 | 389 | 4.09 |

-continued

| No. | | MW | M + H | Rt |
|---|---|---|---|---|
| 2-9 | | 298.3 | 299 | 2.28 |
| 2-10 | | 312.4 | 313 | 3.55 |
| 2-11 | | 352.4 | 353 | 3.96 |
| 2-12 | | 388.5 | 389 | 4.14 |
| 2-13 | | 354.4 | 355 | 3.48 |
| 2-14 | | 367.4 | 368 | 2.74 |

Example 3

Synthesis of 2-Hydroxy-6-(4-pyridin-2-ylmethyl-piperazin-1-yl)-naphthalene-1-carbaldehyde 3-1

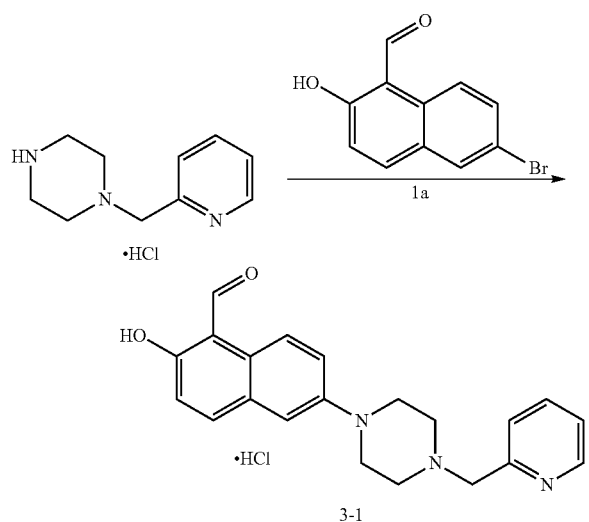

6-Bromo-2-hydroxy-naphthalene-1-carbaldehyde 1a (83 mg, 0.32 mmol), 1-pyridin-2-ylmethyl-piperazine hydrochloride (84 mg, 0.39 mmol), sodium-tert-butoxide (138 mg, 1.44 mmol), tris-(dibenzylideneacetone)dipalladium(0) (20 mg, 22 μmol), (2-biphenyl)di-tert-butylphosphine (25 mg, 47 μmol) were dissolved in 8 mL of dry dioxane. The resulted tan slurry was heated to 100° C. for 3 h. The reaction mixture was evaporated and partitioned between 15 mL of chloroform and 15 mL of water. The pH of the aqueous phase was adjusted to neutral with acetic acid then was separated, and extracted with another 15 mL portion of chloroform. The combined organic phases were dried over sodium sulfate, filtered and evaporated. The resulted solid material was purified by chromatography with chloroform/methanol (98/2) as eluent. The obtained crude product was suspended in 5 mL of HCl in dioxane, filtered and washed with diethyl ether to afford 3-1 (26 mg, 0.7 mmol, 21%).

LC/MS ESI: M+H=348, Rt: 2.75 min; $^1$H NMR (400 MHz, DMSO-$d_6$) δ ppm 11.64 (br. s., 1H), 10.76 (s, 1H), 8.85 (d, J=9.3 Hz, 1H), 8.71 (d, J=4.3 Hz, 1H), 7.94-8.02 (m, 2H), 7.74 (d, J=7.8 Hz, 1H), 7.53 (dd, J=7.2, 4.9 Hz, 1H), 7.47 (dd, J=9.3, 2.5 Hz, 1H), 7.30 (d, J=2.5 Hz, 1H), 7.24 (d, J=9.0 Hz, 1H), 4.58 (s, 2H), 3.58 (br. s., 4H), 3.44 (d, J=4.0 Hz, 4H).

The following compounds were made by the above procedure:

| No. | | MW | M + H | Rt |
|---|---|---|---|---|
| 3-1 | (structure) | 347.4 | 348 | 2.76 |
| 3-2 | (structure) | 374.5 | 375 | 3.01 |
| 3-3 | (structure) | 360.5 | 361 | 3.07 |

-continued
| No. | | MW | M + H | Rt |
|---|---|---|---|---|
| 3-4 | 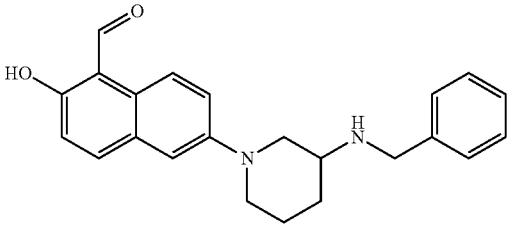 [SMILES: O=Cc1c(O)ccc2cc(N3CCCC(NCc4ccccc4)C3)ccc12] | 360.5 | 361 | 3.16 |
| 3-5 | 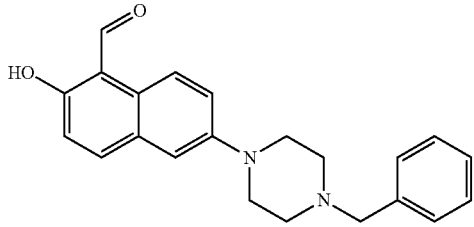 [SMILES: O=Cc1c(O)ccc2cc(N3CCN(Cc4ccccc4)CC3)ccc12] | 346.4 | 345 | 2.99 |
| 3-6 | 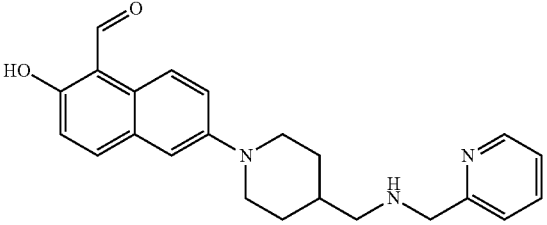 [SMILES: O=Cc1c(O)ccc2cc(N3CCC(CNCc4ccccn4)CC3)ccc12] | 375.5 | 376 | 2.70 |
| 3-7 | 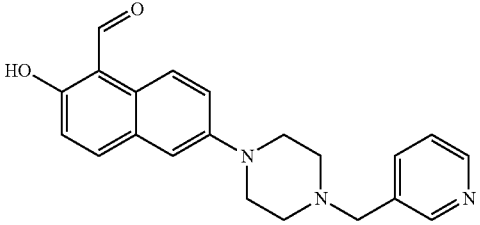 [SMILES: O=Cc1c(O)ccc2cc(N3CCN(Cc4cccnc4)CC3)ccc12] | 347.4 | 348 | 2.65 |
| 3-8 | 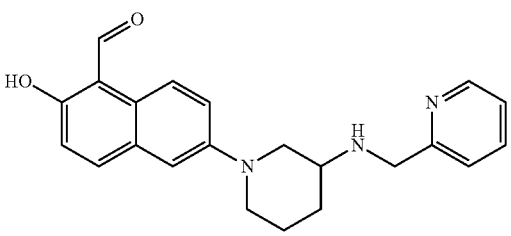 [SMILES: O=Cc1c(O)ccc2cc(N3CCCC(NCc4ccccn4)C3)ccc12] | 361.4 | 362 | 2.99 |
| 3-9 | 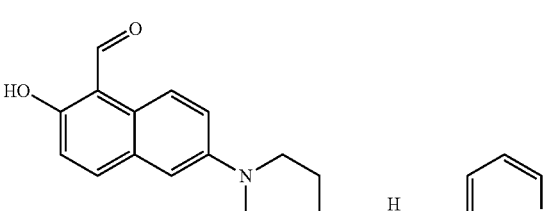 | 375.5 | 376 | 2.45 |

-continued

| No. | | MW | M + H | Rt |
|---|---|---|---|---|
| 3-10 | (structure) | 361.4 | 362 | 2.69 |
| 3-11 | (structure) | 361.4 | 362 | 2.85 |
| 3-12 | (structure) | 361.4 | 362 | 2.60 |
| 3-13 | (structure) | 339.4 | 338 (M − H) | 2.74 |
| 3-14 | (structure) | 389.5 | 390 | 2.97 |
| 3-15 | (structure) | 346.4 | 347 | 3.06 |

-continued
| No. | | MW | M + H | Rt |
|---|---|---|---|---|
| 3-16 | 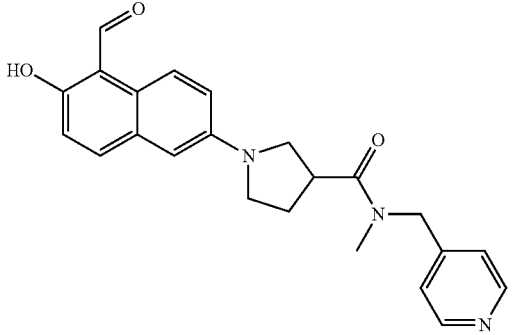 [SMILES: CN(Cc1ccncc1)C(=O)C1CCN(c2ccc3c(C=O)c(O)ccc3c2)C1] | 389.5 | 390 | 2.95 |
| 3-17 | 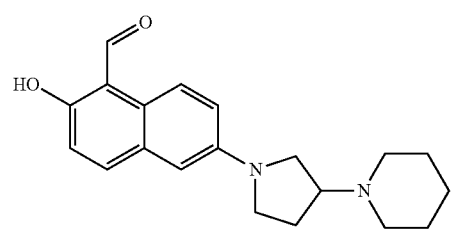 [SMILES: O=Cc1c(O)ccc2cc(N3CCC(N4CCCCC4)C3)ccc12] | 324.4 | 325 | 2.86 |
| 3-18 | 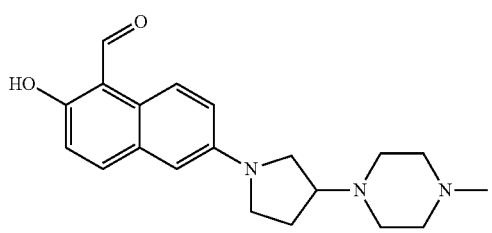 [SMILES: CN1CCN(C2CCN(c3ccc4c(C=O)c(O)ccc4c3)C2)CC1] | 339.4 | 340 | 2.76 |
| 3-19 | 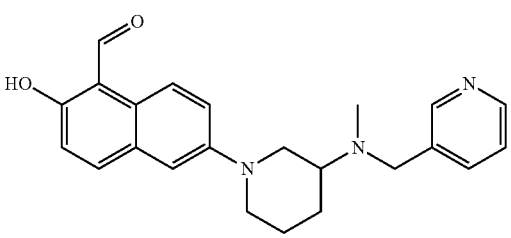 [SMILES: CN(Cc1cccnc1)C1CCCN(c2ccc3c(C=O)c(O)ccc3c2)C1] | 375.5 | 376 | 2.78 |
| 3-20 | 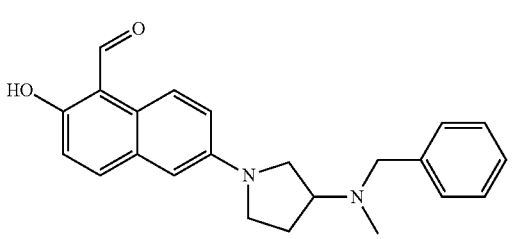 [SMILES: CN(Cc1ccccc1)C1CCN(c2ccc3c(C=O)c(O)ccc3c2)C1] | 360.5 | 361 | 3.04 |
| 3-21 | 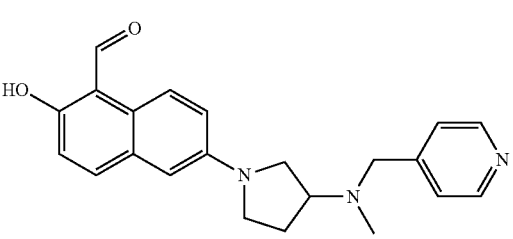 [SMILES: CN(Cc1ccncc1)C1CCN(c2ccc3c(C=O)c(O)ccc3c2)C1] | 361.4 | 362 | 2.69 |

| No. | MW | M + H | Rt |
|---|---|---|---|
| 3-22 | 360.5 | 361 | 3.16 |
| 3-23 | 346.4 | 347 | 3.02 |
| 3-24 | 361.4 | 362 | 2.78 |

Example 4

Synthesis of 2-Hydroxy-6-(4-methanesulfonyl-piperazin-1-yl)-naphthalene-1-carbaldehyde 4-1

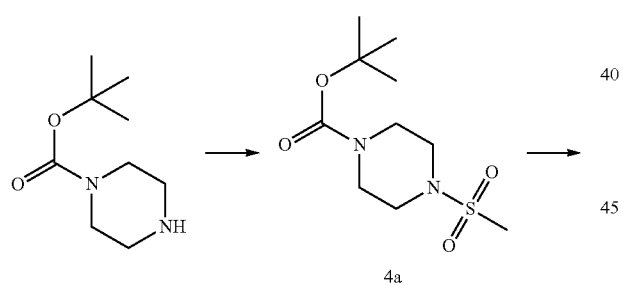

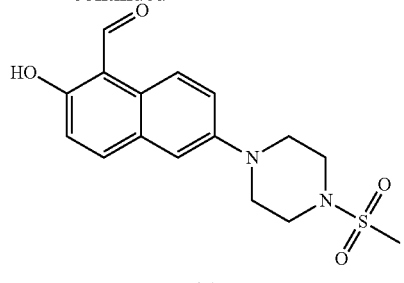

4-1

4-Methanesulfonyl-piperazine-1-carboxylic acid tert-butyl ester 4a

Piperazine-1-carboxylic acid tert-butyl ester (562 mg, 3.02 mmol) and triethylamine (915 mg, 9.06 mmol) were dissolved in 30 mL dichloroethane, cooled to 0° C., and methanesulfonyl chloride (257 µL, 3.32 mmol) was added dropwise, and the mixture was stirred in the cooling bath for 2 h. Then the mixture was extracted with 5% citric acid and brine. The organic layers was dried over sodium sulfate, filtered and evaporated to afford as a white solid (644 mg, 2.44 mmol, 80%).

1-Methanesulfonyl-piperazine hydrochloride 4b

4-Methanesulfonyl-piperazine-1-carboxylic acid tert-butyl ester (640 mg, 2.42 mmol was dissolved in ethyl acetate (20 mL) and ethyl acetate containing HCl was added to the solution at 0° C. and let to reach room temperature. After 3 h stirring, the suspension was filtered and washed with diethyl ether to obtain 4b (420 mg, 2.1 mmol, 86%).

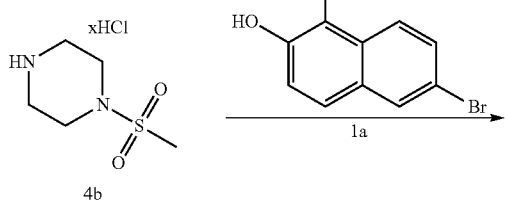

2-Hydroxy-6-(4-methanesulfonyl-piperazin-1-yl)-naphthalene-1-carbaldehyde 4-1

6-Bromo-2-hydroxy-naphthalene-1-carbaldehyde 1a (150 mg, 0.6 mmol), 1-methanesulfonyl-piperazine hydrochloride 4b (132 mg, 0.66 mmol), sodium-tert-butoxide (190 mg, 1.98 mmol), tris-(dibenzylideneacetone)dipalladium(0) (38 mg, 41 μmol), (2-biphenyl)di-tert-butylphosphine (27 mg, 90 μmol) were dissolved in 18 mL of dry dioxane. The resulted suspension was heated to 100° C. for 3 h. The reaction mixture was evaporated and partitioned between 30 mL of dichloromethane and 30 mL of water. The pH of the aqueous phase was adjusted to neutral with acetic acid then was separated, and extracted with another 30 mL portion of dichloromethane. The combined organic phases were dried over sodium sulfate, filtered and evaporated. The resulted solid material was purified by chromatography with chloroform as eluent. The obtained crude product was triturated with diethyl ether to afford 4-1 as a dark yellow solid (78 mg, 0.23 mmol, 39%).

LC/MS ESI: M+H=335, Rt: 3.42 min; $^1$H NMR (400 MHz, DMSO-$d_6$) δ ppm 11.68 (br. s., 1H), 10.76 (s, 1H), 8.80 (d, J=9.3 Hz, 1H), 7.98 (d, J=9.0 Hz, 1H), 7.48 (dd, J=9.3, 2.8 Hz, 1H), 7.27 (d, J=2.8 Hz, 1H), 7.16 (d, J=9.0 Hz, 1H), 3.31 (br. s., 8H), 2.94 (s, 3H).

The following compounds were made by the above procedure:

| No. | | MW | M + H | Rt |
|---|---|---|---|---|
| 4-1 | (structure) | 334.4 | 335 | 3.42 |
| 4-2 | (structure) | 362.4 | 363 | 2.76 |
| 4-3 | (structure) | 348.4 | 349 | 3.05 |
| 4-4 | (structure) | 348.4 | 349 | 3.35 |
| 4-5 | (structure) | 362.4 | 363 | 3.62 |

Example 5

Synthesis of N-[1-(5-Formyl-6-hydroxy-naphthalen-2-yl)-pyrrolidin-3-yl]-N-methyl-acetamide 5-2

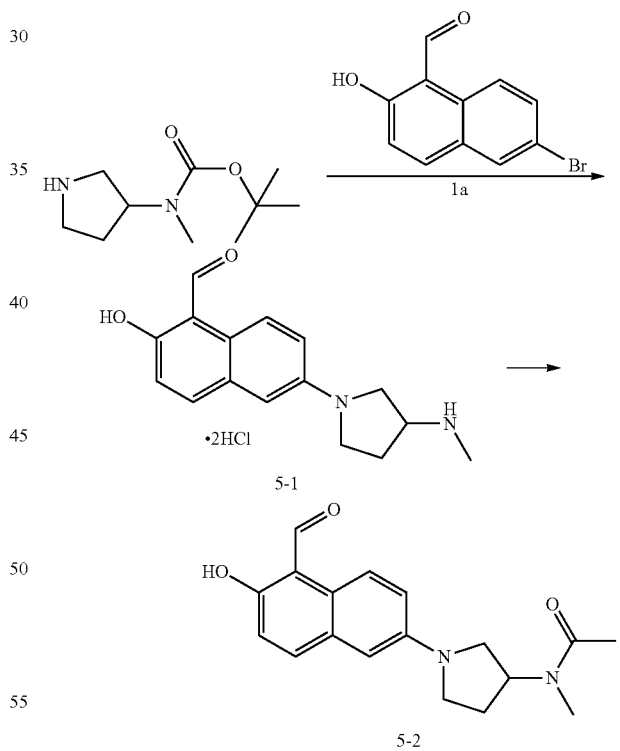

2-Hydroxy-6-(3-methylamino-pyrrolidin-1-yl)-naphthalene-1-carbaldehyde dihydrochloride 5-1

6-Bromo-2-hydroxy-naphthalene-1-carbaldehyde 1a (150 mg, 0.6 mmol), methyl-pyrrolidin-3-yl-carbamic acid tert-butyl ester (144 mg, 0.72 mmol), sodium-tert-butoxide (253 mg, 2.64 mmol), tris-(dibenzylideneacetone)dipalladium(0) (38 mg, 42 μmol), (2-biphenyl)di-tert-butylphosphine (25 mg, 90 μmol) were dissolved in 16 mL of dry dioxane. The resulting tan slurry was heated to 100° C. for 3 h. The reaction mixture was evaporated and partitioned between 20 mL of chloroform and 20 mL of water. The pH of the aqueous phase was adjusted to neutral with acetic acid then was separated, and extracted with another 20 mL portion of chloroform. The combined organic phases were dried over sodium sulfate, filtered and evaporated. The resulting solid material was purified by chromatography with chloroform as eluent. The obtained crude intermediate was triturated with diethyl ether. The resulted solid was dissolved in ethyl acetate containing HCl (10 mL) at 0° C. and let to reach room temperature. After 2 h, the resulting suspension was filtered and washed with diethyl ether to obtain 5-1 (78 mg, 0.23 mmol, 99%).

LC/MS ESI: M+H=271, Rt: 2.67 min; $^1$H NMR (400 MHz, DMSO-$d_6$) salt δ ppm 11.67 (br. s., 1H), 10.75 (s, 1H), 9.37 (br. s., 2H), 8.80 (d, J=9.3 Hz, 1H), 7.95 (d, J=9.0 Hz, 1H), 7.08-7.22 (m, 2H), 6.90 (d, J=2.5 Hz, 1H), 3.84-3.93 (m, 1H), 3.59-3.67 (m, 1H), 3.51-3.59 (m, 2H), 3.28-3.41 (m, 1H), 2.62 (t, J=5.4 Hz, 3H), 2.32-2.45 (m, 1H), 2.14-2.30 (m, 1H).

N-[1-(5-Formyl-6-hydroxy-naphthalen-2-yl)-pyrrolidin-3-yl]-N-methyl-acetamide 5-2

2-Hydroxy-6-(3-methylamino-pyrrolidin-1-yl)-naphthalene-1-carbaldehyde dihydrochloride 5-1 (60 mg, 018 mmol) was dissolved in 3 mL of abs. dichloromethane and acetic anhydride (54 mg, 53 mmol) was added. After 30 min stirring at room temperature 1 mL of saturated sodium bicarbonate was added. The mixture was transferred into a reparatory funnel, and the organic layer was separated, dried over sodium sulfate, evaporated and triturated with diethyl ether. The resulting slurry was filtered off and dried to afford 5-2 (40 mg, 13 mmol, 73%).

LC/MS ESI: M+H=313, Rt: 3.46 min; $^1$H NMR (400 MHz, CDCl$_3$) rotamers A and B in a ratio of 70:30 δ ppm 12.81 (s, 1H, A+B), 10.75 (s, 1H, A+B), 8.17-8.27 (m, 1H, A+B), 7.76-7.87 (m, 1H, A+B), 6.97-7.13 (m, 2H, A+B), 6.78 (br. s., 1H, A+B), 5.37-5.55 (m, 0.7H, A), 4.57-4.79 (m, 0.3H, B), 3.50-3.68 (m, 2H, A+B), 3.24-3.46 (m, 2H, A+B), 2.98 (s, 2.1H, A), 2.92 (s, 0.9H, B), 2.24-2.37 (m, 0.7H, A), 2.23 (s, 0.9H, B), 2.14 (s, 2.1H, A), 2.04-2.13 (m, 0.7H, A).

Example 6

Synthesis of N-[1-(5-Formyl-6-hydroxy-naphthalen-2-yl)-pyrrolidin-3-yl]-acetamide (IRE-1508) 6-1

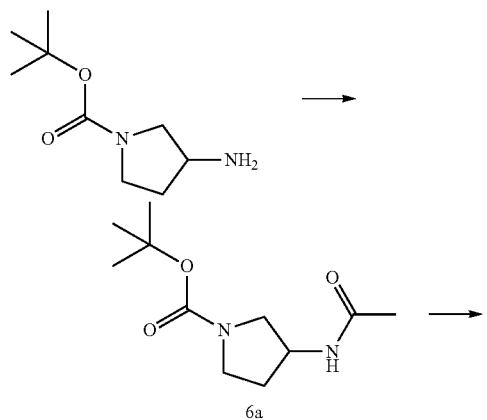

6a

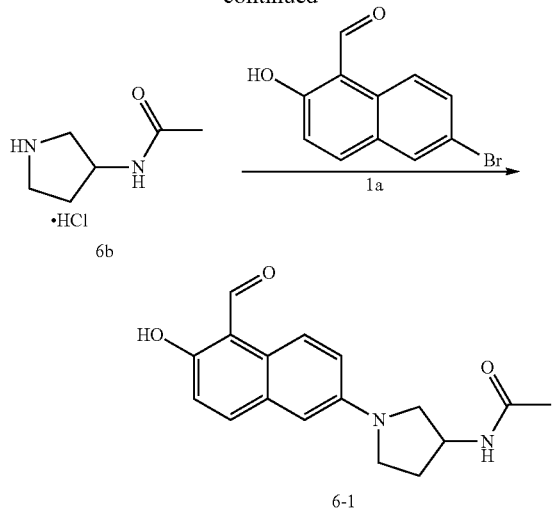

3-Acetylamino-pyrrolidine-1-carboxylic acid tert-butyl ester 6a

3-Amino-pyrrolidine-1-carboxylic acid tert-butyl ester (2.0 g, 10.75 mmol) was dissolved in 20 mL of dichloroethane and acetic anhydride (1.15 g, 11.29 mmol) and triethylamine (1.14 g, 11.29) was added. After stirring for 1 h at room temperature the mixture was evaporated and the residue was pushed through a plug of silica with chloroform as eluent to afford 6a (2.2 g, 9.65 mmol, 90%).

N-Pyrrolidin-3-yl-acetamide hydrochloride 6b

3-Acetylamino-pyrrolidine-1-carboxylic acid tert-butyl ester 6a (2.2 g, 9.65 mmol) was dissolved in ethyl acetate containing HCl (20 mL) at 0° C. and let to reach room temperature. After 2 h stirring, the suspension was evaporated (hygroscopic if filtered). Ethanol and then diethyl ether was evaporated from the oily crude material to remove HCl and afford 6b (1.15 g, 7.02 mmol, 73%) as a brown oil.

N-[1-(5-Formyl-6-hydroxy-naphthalen-2-yl)-pyrrolidin-3-yl]-acetamide 6-1

6-Bromo-2-hydroxy-naphthalene-1-carbaldehyde 1a (151 mg, 0.6 mmol), N-pyrrolidin-3-yl-acetamide hydrochloride 6b (115 mg, 0.90 mmol), sodium-tert-butoxide (280 mg, 3.0 mmol), tris-(dibenzylideneacetone)dipalladium(0) (38 mg, 42 μmol), (2-biphenyl)di-tert-butylphosphine (27 mg, 90 μmol) were dissolved in 12 mL of dry dioxane. The resulting tan slurry was heated to 100° C. for 3 h. The reaction mixture was evaporated and partitioned between 20 mL of chloroform and 20 mL of water. The pH of the aqueous phase was adjusted to neutral with acetic acid then was separated, and extracted with another 20 mL portion of chloroform. The combined organic phases were dried over sodium sulfate, filtered and evaporated. The resulting solid material was purified by eluting with 98:2 chloroform/methanol. The obtained crude product was triturated with diethyl ether to afford 6-1. (34 mg, 0.11 mmol, 19%).

LC/MS ESI: M+H=299, Rt: 3.22 min; $^1$H NMR (400 MHz, DMSO-$d_6$) δ ppm 11.55 (s, 1H), 10.75 (s, 1H), 8.75 (d, J=9.3 Hz, 1H), 8.17 (d, J=7.0 Hz, 1H), 7.92 (d, J=9.0 Hz, 1H), 7.06-7.15 (m, 2H), 6.82 (d, J=2.5 Hz, 1H), 4.34-4.44

(m, 1H), 3.56 (dd, J=9.7, 6.4 Hz, 1H), 3.41-3.50 (m, 1H), 3.34-3.40 (m, 1H), 3.14 (dd, J=9.8, 4.3 Hz, 1H), 2.15-2.26 (m, 1H), 1.86-1.96 (m, 1H), 1.82 (s, 3H).

The following compounds were made by the above procedure:

5 mmol) in dichloromethane (10 mL, distilled from CaH$_2$). The reaction mixture was cooled in ice water, trifluoromethanesulfonic anhydride (1 mL, 1.64 g, 6 mmol) was added dropwise below 5° C. and the mixture was stirred in the cooling bath for 2 h. 1 N Hydrochloric acid (12 mL) was then added; the aqueous layer was separated and extracted with dichloromethane (2×5 mL). The combined organic layers were washed with water (3×5 mL), dried over magnesium sulfate and evaporated to dryness. The oily crude product was purified by column chromatography on silica gel eluting with 2:1 hexane/ethyl acetate. In this manner 7-trifluoromethanesulfonyoxy-2-naphthol 7a (0.70 g, yield: 48%) was obtained as a thick oil which solidified upon standing.

LC/MS ESI: M−H=291, Rt: 3.83 min

This intermediate was used in the next step without further purification.

| No. | | MW | M + H | Rt |
|---|---|---|---|---|
| 6-1 | ![structure] Ch | 189.34 | 299 | 3.22 |
| 6-2 | ![structure] C | 396.5 | 397 | 2.73 |

Example 7

Synthesis of trifluoromethanesulfonic acid 8-formyl-7-hydroxy-naphthalen-2-yl ester 7-1

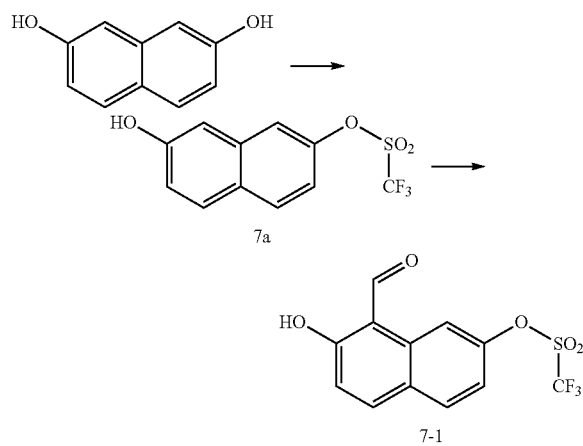

7a 7-1

Trifluoromethanesulfonic acid 7-hydroxy-naphthalen-2-yl ester 7a

Pyridine (2.85 mL, 2.8 g, 35 mmol, dried over KOH) was added to a suspension of 2,7-dihydroxynaphthalene (0.8 g,

Synthesis of trifluoromethanesulfonic acid 8-formyl-7-hydroxy-naphthalen-2-yl ester 7-1

To a solution of 7-trifluoromethanesulfonyoxy-2-naphthol 7a (0.40 g, 1.37 mmol) in dichloromethane (10 mL, distilled from CaH$_2$) stirred in an ice water bath, titanium tetrachloride (0.30 mL, 0.52 g, 2.74 mmol) and then dichloromethyl methyl ether (0.37 mL, 0.47 g, 4.1 mmol) were added below 10° C. The mixture was stirred in the cooling bath for 2 h. 2 N Hydrochloric acid (10 mL) was then added; the aqueous layer was separated and extracted with dichloromethane (2×5 mL). The combined organic layers were washed with brine (5×5 mL), dried over magnesium sulfate and evaporated to dryness. The crude product was purified by column chromatography on silica gel eluting with 4:1 hexane/diethyl ether. In this manner 7-1 (0.26 g, yield: 59%) was obtained as a semisolid. Trituration of a sample with diisopropyl ether yielded a white powder.

LC/MS ESI: M+H=319, Rt: 4.09 min; $^1$H NMR (400 MHz, CDCl$_3$) δ ppm 13.22 (s, 1H), 10.73 (s, 1H), 8.22 (d, J=2.3 Hz, 1H), 8.03 (d, J=9.3 Hz, 1H), 7.92 (d, J=8.8 Hz, 1H), 7.36 (dd, J=9.0, 2.3 Hz, 1H), 7.25 (d, J=9.0 Hz, 1H).

Example 8

Synthesis of (5-formyl-6-hydroxy-naphthalen-2-yloxy)-acetic acid 8-1

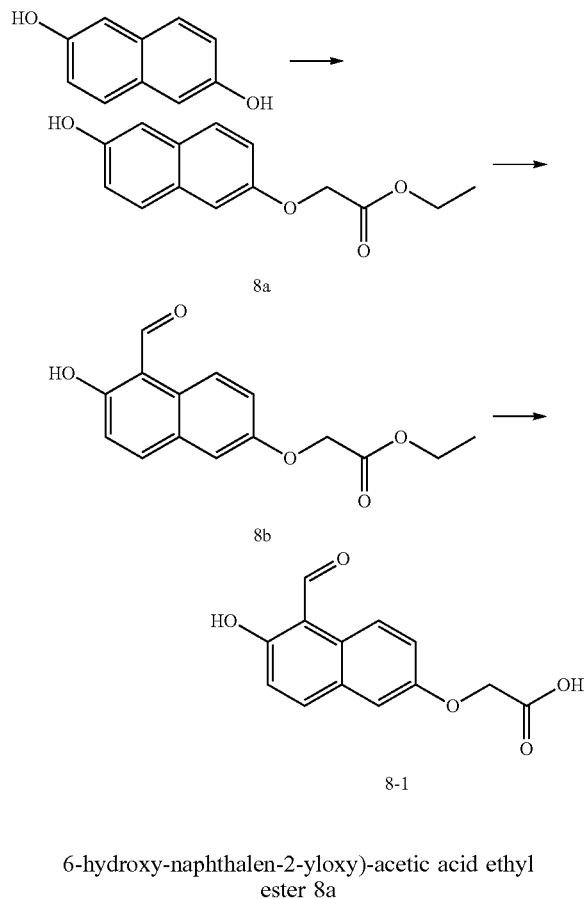

6-hydroxy-naphthalen-2-yloxy)-acetic acid ethyl ester 8a

To a solution of 2,6-dihydroxynaphthalene (3 g, 18.75 mmol) in dimethylformamide (90 mL) NaH (822 mg, ~60% oil dispersion) was added. After 1 h stirring bromoacetic acid ethyl ester (2.29 mL, 20.62 mmol) was added. The suspension was stirred for another 4 h at room temperature. The solvent was evaporated under reduced pressure, then suspended in water (200 mL) and acidified with 10% hydrochloric acid, then extracted with ethyl acetate (2×150 mL). The combined organic layers were dried over magnesium sulfate and evaporated to dryness. The crude product was purified by column chromatography on silica gel, eluting with chloroform to afford 8a as a solid (1.54 g, 6.26 mmol, 33%).

LC/MS ESI: M+H=247, Rt: 3.28 min.

This intermediate was used in the next step without further purification.

(5-formyl-6-hydroxy-naphthalen-2-yloxy)-acetic acid ethyl ester 8b

6-Hydroxy-naphthalen-2-yloxy)-acetic acid ethyl ester 8a (2.11 g, 8.58 mmol) in dichloromethane (45 mL, distilled from CaH$_2$) was added to a stirred solution of titanium tetrachloride (1.55 mL, 14.3 mmol) and dichloromethyl methyl ether (2.3 mL, 25.7 mmol) in dichloromethane (35 mL, distilled from CaH$_2$) at 0° C., and the mixture was stirred in the cooling bath for 1 h, then at room temperature overnight. 1 N hydrochloric acid (80 mL) was then added; the organic layer was separated and extracted with 1 N hydrochloric acid (2×80 mL), then with 100 mL aqueous EDTA disodium salt. The organic layer was washed with 50 mL of saturated sodium bicarbonate, dried over magnesium sulfate and evaporated to dryness. The crude product was purified by column chromatography on silica gel, eluting with hexane/ethyl acetate to afford 8b as a reddish solid (355 mg, 1.29 mmol, 15%).

LC/MS (ESI): M+H=275, Rt: 3.66 min.

(5-formyl-6-hydroxy-naphthalen-2-yloxy)-acetic acid 8-1

(5-Formyl-6-hydroxy-naphthalen-2-yloxy)-acetic acid ethyl ester 8b (340 mg, 1.24 mmol) was dissolved in 40 mL 1:1 mixture of dioxane-10% aq. sodium hydroxide and stirred for 30 min at room temperature. 50 mL Dichloromethane was added to the reaction mixture, the aqueous layer was separated and washed with 50 mL dichloromethane, acidified with 1N hydrochloric acid and the precipitate was filtered off and washed with water to afford 8-1 as a pink solid (270 mg, 1.09 mmol, 88%).

LC/MS ESI: M−H=245, Rt: 2.99 min; $^1$H NMR (400 MHz, DMSO-d$_6$) δ ppm 11.69 (br. s., 1H), 10.76 (s, 1H), 8.86 (m, 1H), 8.06 (d, J=8.8 Hz, 1H), 7.30 (m, 2H), 7.21 (d, J=9.2 Hz, 1H), 4.76 (s, 2H).

Example 9

Synthesis of 2-Hydroxy-7-(2-morpholin-4-yl-2-oxo-ethoxy)-naphthalene-1-carbaldehyde 9-1

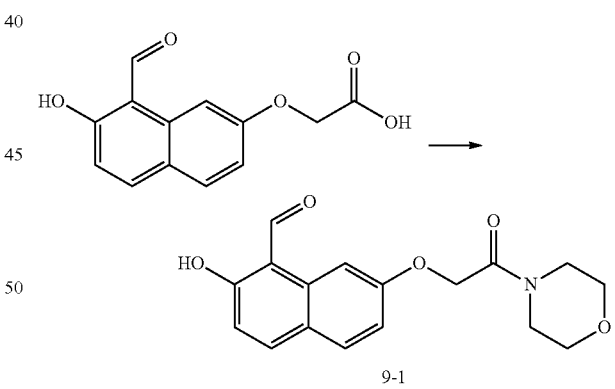

8-Formyl-7-hydroxy-naphthalen-2-yloxy)-acetic acid (123 mg, 0.5 mmol), 1-hydroxybenzotriazole (149 mg, 1.1 mmol), morpholine (95 µL, 1.1 mmol), triethylamine (350 µL, 2.5 mmol) and 1-ethyl-3-(3-dimethylaminopropyl) carbodiimide hydrochloride (210 mg, 1.1 mmol) were dissolved in tetrahydrofuran (4 mL), and the mixture was stirred overnight at room temperature. The solvent was evaporated under reduced pressure and to the residue was poured 30 mL saturated sodium bicarbonate and extracted with chloroform (2×30 mL). The combined organic layers were dried over magnesium sulfate and evaporated to dryness. The crude product was purified by column chromatography on silica gel, eluting with chloroform, then was finally triturated with diethyl ether yielding 9-1 as a yellow powder (65 mg, 0.206 mmol, 41%).

LC/MS ESI: M+H=316, Rt: 3.11 min; $^1$H NMR (400 MHz, DMSO-d$_6$) δ ppm 11.90 (br. s., 1H), 10.77 (s, 1H), 8.38 (d, J=2.5 Hz, 1H), 8.04 (d, J=8.8 Hz, 1H), 7.81 (d, J=9.0 Hz, 1H), 7.10 (dd, J=8.9, 2.6 Hz, 1H), 7.05 (d, J=9.0 Hz, 1H), 4.97 (s, 2H), 3.69 (br. s., 2H), 3.60 (br. s., 2H), 3.54 (br. s., 2H), 3.47 (br. s., 2H).

The following compounds were made by the above procedure:

| No. | | MW | M + H | Rt |
|---|---|---|---|---|
| 9-1 | (structure) | 315.3 | 316 | 3.11 |
| 9-2 | (structure) | 342.4 | 343 | 2.52 |
| 9-3 | (structure) | 358.4 | 359 | 2.50 |
| 9-4 | (structure) | 316.4 | 317 | 2.49 |
| 9-5 | (structure) Che | 328.3 | 329 | 2.99 |
| 9-6 | (structure) Chem | 315.3 | 316 | 3.07 |

Example 10

Synthesis of 2-Hydroxy-7-[2-(4-methyl-piperazin-1-yl)-2-oxo-ethoxy]-naphthalene-1-carbaldehyde 10-1

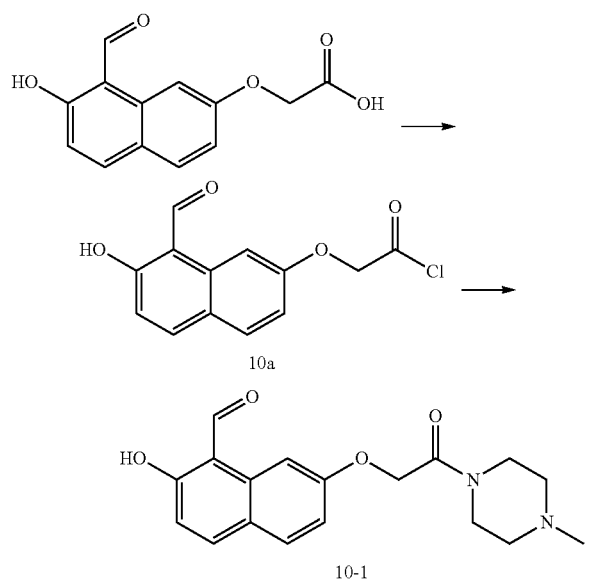

(8-Formyl-7-hydroxy-naphthalen-2-yloxy)-acetyl chloride 10a

Thionyl chloride (20 mL) was added to the 8-formyl-7-hydroxy-naphthalen-2-yloxy)-acetic acid (200 mg, 0.81 mmol), and the mixture was refluxed for 2 h. The solvent was evaporated under reduced pressure and the residue was used in the next step without further purification.

2-Hydroxy-7-[2-(4-methyl-piperazin-1-yl)-2-oxo-ethoxy]-naphthalene-1-carbaldehyde 10-1

To a solution of N-methylpiperazine (123 µL, 0.89 mmol) and triethylamine (340 µL, 2.44 mmol) in 15 mL dichloroethane at 0° C., 8-Formyl-7-hydroxy-naphthalen-2-yloxy)-acetyl chloride 10a was added and the mixture was allowed to warm to room temperature. Then the mixture was extracted with water (25 mL) and the aqueous layer was washed with dichloromethane (2×25 mL). The combined organic layers were dried over magnesium sulfate and evaporated to dryness. The crude product was purified by column chromatography on silica gel, eluting with 40:1 chloroform/methanol. The obtained product was triturated with diethyl ether and filtered to give 10-1 (20 mg, 60.9 µmol, 8%).

LC/MS ESI: M+H=329, Rt: 2.49 min; $^1$H NMR (400 MHz, DMSO-$d_6$) δ ppm 11.92 (br. s., 1H), 10.77 (s, 1H), 8.37 (d, J=2.5 Hz, 1H), 8.04 (d, J=9.0 Hz, 1H), 7.80 (d, J=9.0 Hz, 1H), 7.10 (dd, J=8.8, 2.5 Hz, 1H), 7.05 (d, J=8.8 Hz, 1H), 4.95 (s, 2H), 3.44-3.56 (m, 4H), 2.43 (br. s., 2H), 2.33 (br. s., 2H), 2.23 (s, 3H).

Example 11

Synthesis of 2-Hydroxy-6-[4-(4-methyl-piperazine-1-carbonyl)-phenoxy]-naphthalene-1-carbaldehyde 11-1

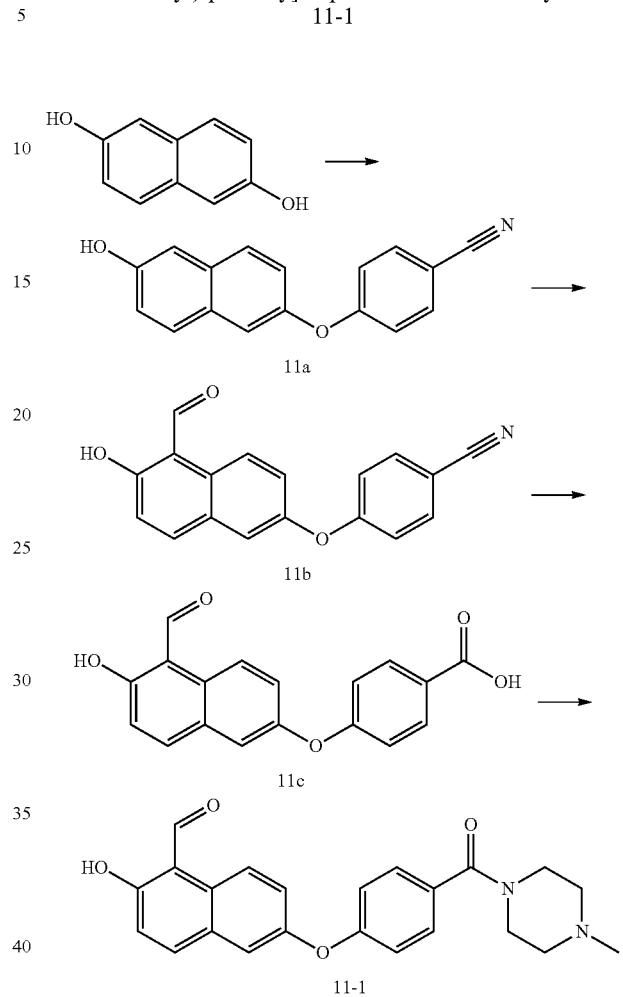

4-(6-Hydroxy-naphthalen-2-yloxy)-benzonitrile 11a

Naphthalene-2,6-diol (2.28 g, 14.25 mmol), 4-fluoro-benzonitrile (1.72 g, 14.25 mmol) and $K_2CO_3$ (1.96 g, 14.25 mmol) were dissolved in 60 mL of DMF and the mixture was heated to 150° C. for 2 h. The reaction mixture was partitioned between water and dichloromethane. The organic layer was separated and extracted, washed with 1N hydrochloric acid, separated, dried over sodium sulfate, filtered and evaporated. The obtained crude product was purified by column chromatography on silica gel, eluting with 20:1 chloroform/methanol to afford 11a (610 mg, 2.34 mmol, 16%).

4-(5-Formyl-6-hydroxy-naphthalen-2-yloxy)-benzonitrile 11b 4-(6-Hydroxy-naphthalen-2-yloxy)-benzonitrile 11a (550 mg, 2.03 mmol) in dichloromethane (10 mL, distilled from $CaH_2$) was added to a stirred solution of titanium tetrachloride (0.67 mL, 3.39 mmol) and dichloromethyl methyl ether (0.62 mL, 6.09 mmol) in dichloromethane (10 mL, distilled from $CaH_2$) at 0° C., and the mixture was stirred at 0° C. for 1 h, then at room temperature overnight. 1 N hydrochloric acid (20 mL) was then added; the organic layer was separated and extracted with 1 N hydrochloric acid (2×20 mL). The organic layer was washed with 10 mL of saturated sodium bicarbonate, dried over magnesium sulfate and evaporated to dryness. The crude product was purified by column chromatography on silica gel, eluting with dichloromethane to afford 11b (190 mg, 0.66 mmol, 32%).

LC/MS ESI: M−H=288, Rt: 4.05 min; $^1$H NMR (400 MHz, DMSO-$d_6$) δ ppm 11.80 (br. s., 1H), 10.79 (s, 1H), 9.06 (d, J=9.2 Hz, 1H), 8.10 (d, J=8.8 Hz, 1H), 7.84 (m, 2H), 7.65 (d, J=2.4 Hz, 1H), 7.45 (dd, J=9.2, 2.8 Hz, 1H) 7.27 (d, J=8.8 Hz, 1H), 7.07 (m, 2H).

4-(5-Formyl-6-hydroxy-naphthalen-2-yloxy)-benzoic acid 11c 4-(5-Formyl-6-hydroxy-naphthalen-2-yloxy)-benzonitrile 11b (170 mg, 0.59 mmol) was dissolved in a mixture of 20 mL of methanol and 20 mL of 10% aqueous sodium hydroxide. The reaction was heated to 80° C. for 12 h. The cooled reaction mixture was acidified with conc. aqueous hydrochloric acid and the resulting precipitate was filtered and the crude product was purified by column chromatography on silica gel, eluting with 20:1 chloroform/methanol, to afford 11-1 (60 mg, 0.19 mmol, 32%).

LC/MS ESI: M−H=307, Rt: 3.69 min; $^1$H NMR (400 MHz, DMSO-$d_6$) δ ppm, 10.79 (s, 1H), 9.04 (d, J=9.6 Hz, 1H), 8.09 (d, J=9.2 Hz, 1H), 7.95 (m, 2H), 7.61 (d, J=2.4 Hz, 1H), 7.45 (dd, J=9.2, 2.8 Hz, 1H), 7.27 (d, J=8.8 Hz, 1H), 7.07 (m, 2H).

2-Hydroxy-6-[4-(4-methyl-piperazine-1-carbonyl)-phenoxy]-naphthalene-1-carbaldehyde 11-1

4-(5-Formyl-6-hydroxy-naphthalen-2-yloxy)-benzoic acid 11c (40 mg, 0.13 mmol), 1-hydroxybenzotriazole (38 mg, 0.29 mmol), N-methyl-piperazine (32 μL, 0.39 mmol), triethylamine (90 μL, 0.65 mmol) and 1-ethyl-3-(3-dimethylaminopropyl) carbodiimide hydrochloride (55 mg, 0.29 mmol) were dissolved in dimethylformamide (4 mL), and the mixture was stirred overnight at room temperature. The solvent was evaporated under reduced pressure and to the residue was poured 10 mL saturated sodium bicarbonate and extracted with chloroform (2×10 mL). The combined organic layers were dried over magnesium sulfate and evaporated to dryness. The crude product 11-1 was purified by column chromatography on silica gel, eluting with chloroform, then was finally isolated as a HCl salt after treatment with ethyl acetate containing HCl (29 mg, 0.07 mmol, 54%).

LC/MS ESI: M+H=391, Rt: 2.89 min; $^1$H NMR (400 MHz, DMSO-$d_6$) δ ppm 11.81 (s, 1H), 10.90 (br, s, 1H), 10.79 (s, 1H), 9.05 (d, J=9.2 Hz, 1H), 8.08 (d, J=8.8 Hz, 1H), 7.56 (d, J=2.8 Hz, 1H), 7.49 (d, J=8.8 Hz, 1H), 7.43 (dd, J=9.2, 2.4 Hz, 1H), 7.30 (d, J=8.8 Hz, 1H), 7.08 (d, J=8.8 Hz, 2H), 4.20 (br, 2H) 3.40 (br, 4H) 3.05 (br, 2H) 2.77 (s, 3H).

Example 12

Synthesis of 2-Hydroxy-6-[4-methyl-5-(morpholine-4-carbonyl)-thiazol-2-yl]-naphthalene-1-carbaldehyde 12-1

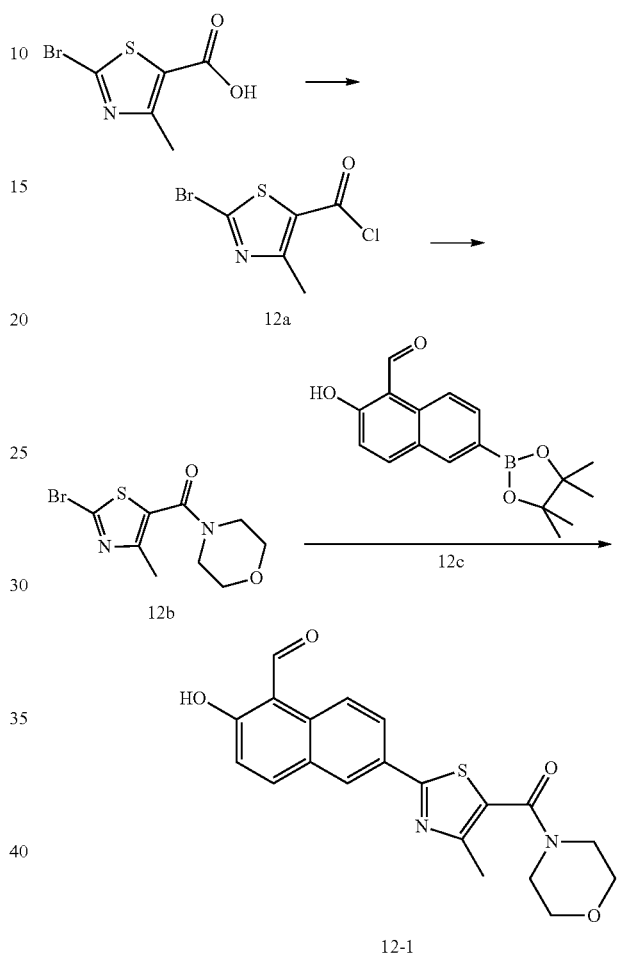

2-Bromo-4-methyl-thiazole-5-carbonyl chloride 12a

2-Bromo-4-methyl-thiazole-5-carboxylic acid (250 mg, 1.13 mmol) was dissolved in 5 mL of thionyl chloride. After refluxing for 1 h the mixture was evaporated, dissolved in 10 mL of toluene and evaporated again to afford 2-bromo-4-methyl-thiazole-5-carbonyl chloride 12a. (228 mg, 0.91 mmol, 84%).

(2-Bromo-4-methyl-thiazol-5-yl)-morpholin-4-yl-methanone 12b

To a stirred mixture of morpholine (87 mg, 1.0 mmol) and diisopropyl-ethyl-amine (184 mg, 1.43 mmol) in 7 mL of abs. dichloroethane at 0° C., 2-bromo-4-methyl-thiazole-5-carbonyl chloride 12a (228 mg, 0.95 mmol) in 7 mL of abs. dichloroethane was added dropwise. The mixture was stirred for an additional 2 h at room temperature. The reaction mixture was extracted with 15 mL of saturated sodium bicarbonate; the organic layer was separated, dried over sodium sulfate, filtered and evaporated to afford (2-bromo- 4-methyl-thiazol-5-yl)-morpholin-4-yl-methanone 12b as a yellow oil. (226 mg, 78 mmol, 82%).

2-Hydroxy-6-[4-methyl-5-(morpholine-4-carbonyl)-thiazol-2-yl]-naphthalene-1-carbaldehyde 12-1

(2-bromo-4-methyl-thiazol-5-yl)-morpholin-4-yl-methanone 12b (226 mg, 0.78 mmol), 2-Hydroxy-6-(4,4,5,5-tetramethyl-[1,3,2]dioxaborolan-2-yl)-naphthalene-1-carbaldehyde (12c, WO2008154484) (231 mg, 0.78 mmol), sodium carbonate (660 mg, 6.24 mmol), and tetrakis(triphenylphosphine)palladium (27 mg, 0.023 mmol) were dissolved in a mixture of 18 mL DMF and 18 mL water. The reaction mixture was stirred at 120° C. under argon for 1 h. The reaction mixture was evaporated to dryness and the solid residue was partitioned between chloroform and water. The aqueous phase was acidified with acetic acid to pH 6. The organic phase was separated, and the aqueous layer was extracted once more with chloroform. The combined organic phases were dried over sodium sulfate, filtered and evaporated. The residue was purified by column chromatography with chloroform as eluent. The crude product was triturated with diethyl ether, filtered off and air dried, affording 12-1 (116 mg, 0.31 mmol, 39%).

LC/MS ESI: M+H=383, Rt: 3.47 min; $^1$H NMR (400 MHz, CDCl$_3$) δ ppm 13.21 (s, 1H), 10.83 (s, 1H), 8.41 (d, J=9.0 Hz, 1H), 8.36 (d, J=1.5 Hz, 1H), 8.13 (dd, J=8.9, 1.5 Hz, 1H), 8.06 (d, J=9.3 Hz, 1H), 7.21 (d, J=9.0 Hz, 1H), 3.73-3.78 (m, 4H), 3.65-3.73 (m, 4H), 2.55 (s, 3H).

The following compounds were made by the above procedure.

| No. | | MW | M + H |
|---|---|---|---|
| 12-1 | | 382.4 | 383 |
| 12-2 | | 381.5 | 382 |
| 12-3 | | 381.5 | 382 |

-continued
| No. | | MW | M + H |
|---|---|---|---|
| 12-4 | 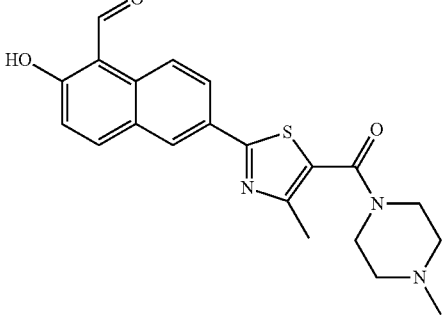 | 395.5 | 396 |
| 12-5 | 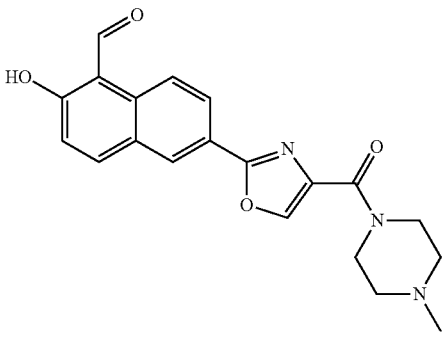 [SMILES: CN1CCN(C(=O)c2coc(-c3ccc4c(C=O)c(O)ccc4c3)n2)CC1] | 365.4 | 366 |
| 12-6 | 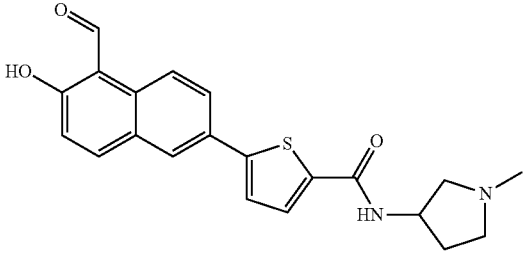 [SMILES: CN1CCC(NC(=O)c2ccc(-c3ccc4c(C=O)c(O)ccc4c3)s2)C1] | 380.5 | 381 |
| 12-7 | 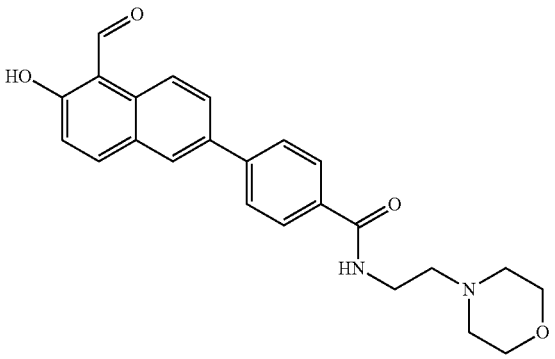 [SMILES: O=Cc1c(O)ccc2cc(-c3ccc(C(=O)NCCN4CCOCC4)cc3)ccc12] | 404.5 | 405 |
| 12-8 | 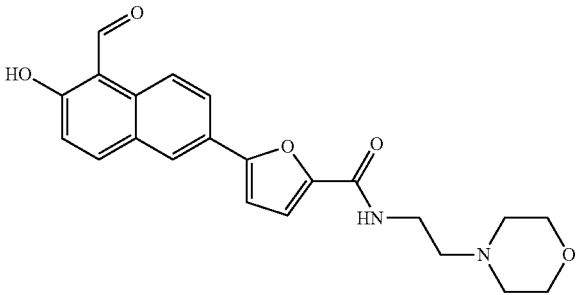 [SMILES: O=Cc1c(O)ccc2cc(-c3ccc(C(=O)NCCN4CCOCC4)o3)ccc12] | 394.4 | 395 |

-continued
| No. | | MW | M + H |
|---|---|---|---|
| 12-9 | 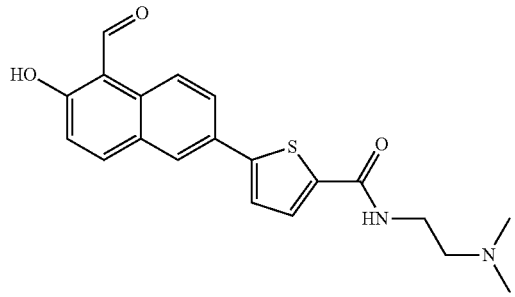 [SMILES: CN(C)CCNC(=O)c1ccc(-c2ccc3c(C=O)c(O)ccc3c2)s1] | 368.5 | 369 |
| 12-10 | 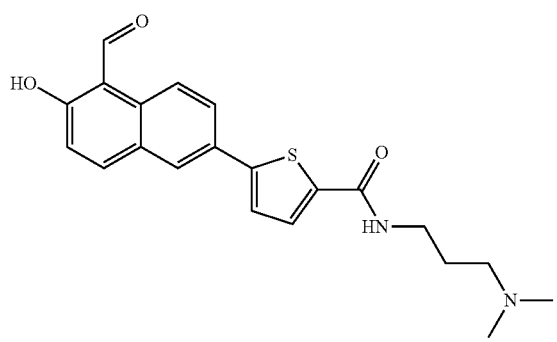 [SMILES: CN(C)CCCNC(=O)c1ccc(-c2ccc3c(C=O)c(O)ccc3c2)s1] | 382.5 | 3.83 |
| 12-11 | 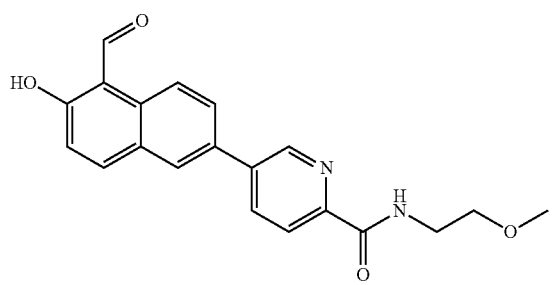 [SMILES: COCCNC(=O)c1ccc(-c2ccc3c(C=O)c(O)ccc3c2)cn1] | 350.4 | 351 |
| 12-12 | 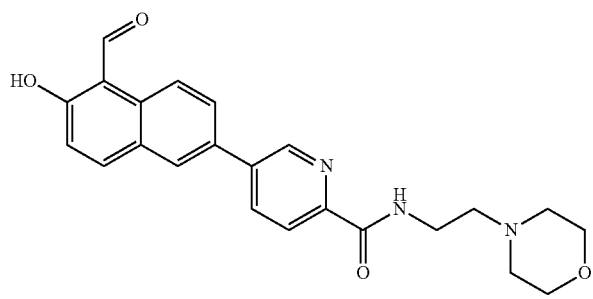 [SMILES: O=Cc1c(O)ccc2cc(-c3ccc(C(=O)NCCN4CCOCC4)nc3)ccc12] | 405.5 | 406 |
| 12-13 | 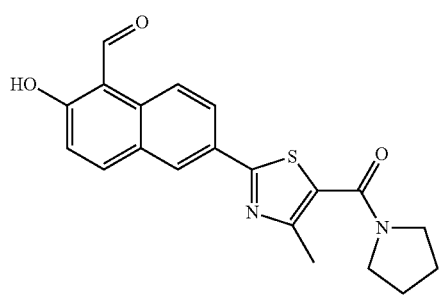 [SMILES: Cc1nc(-c2ccc3c(C=O)c(O)ccc3c2)sc1C(=O)N1CCCC1] | 366.4 | 367 |

| No. | | MW | M + H |
|---|---|---|---|
| 12-14 | 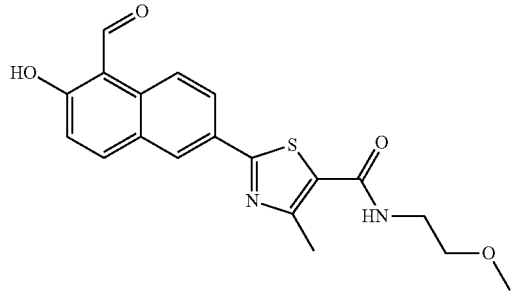 | 370.4 | 371 |
| 12-15 | 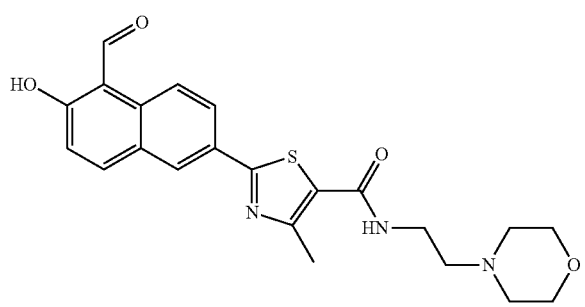 [SMILES: Cc1nc(-c2ccc3c(C=O)c(O)ccc3c2)sc1C(=O)NCCN1CCOCC1] | 425.5 | 426 |
| 12-16 | 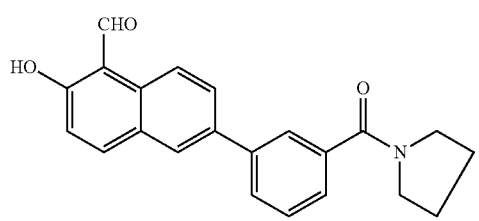 | 345.2 | 346 |
| 12-17 | 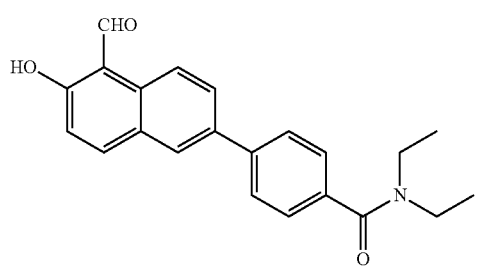 [SMILES: CCN(CC)C(=O)c1ccc(-c2ccc3c(C=O)c(O)ccc3c2)cc1] | 347.1 | 348 |
| 12-18 | 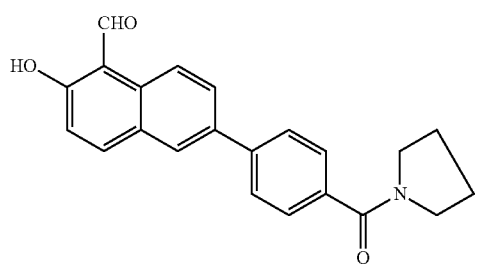 | 345.2 | 346 |

-continued

| No. | | MW | M + H |
|---|---|---|---|
| 12-19 | | 374.1 | 375 |
| 12-20 | | 346.1 | 347 |

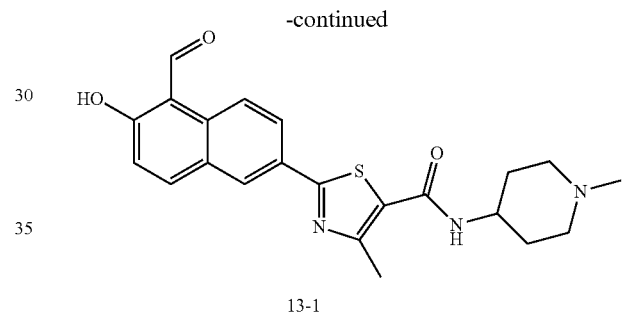

Example 13

Synthesis of 2-(5-Formyl-6-hydroxy-naphthalen-2-yl)-4-methyl-thiazole-5-carboxylic acid (1-methyl-piperidin-4-yl)-amide 13-1

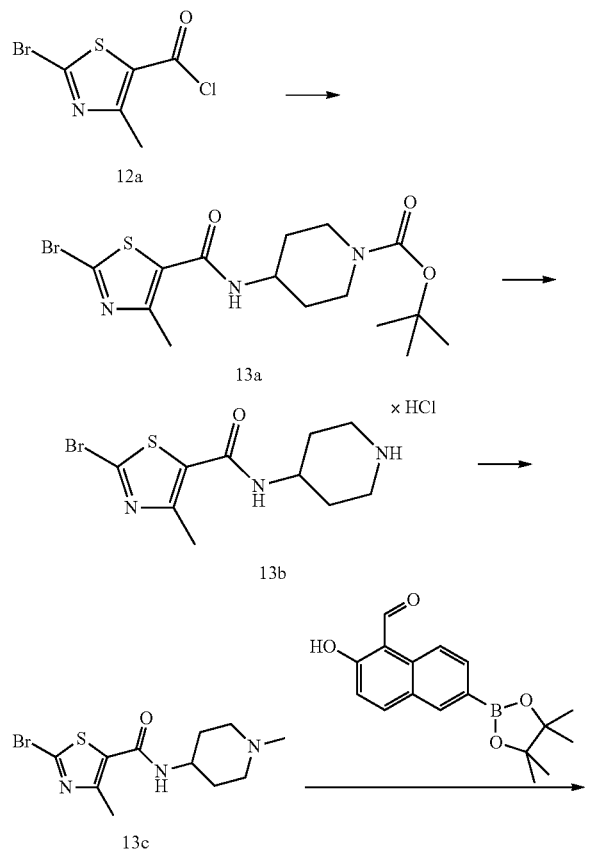

4-[(2-Bromo-4-methyl-thiazole-5-carbonyl)-amino]piperidine-1-carboxylic acid tert-butyl ester 13a To a stirred mixture of 4-amino-piperidine-1-carboxylic acid tert-butyl ester (801 mg, 4.0 mmol) and diisopropyl-ethyl-amine (517 mg, 4.0 mmol) in 40 mL of abs. dichloromethane at 0° C., 2-bromo-4-methyl-thiazole-5-carbonyl chloride 12a (960 mg, 4.0 mmol) in 10 mL of abs. dichloroethane was added dropwise. The mixture was stirred for an additional 2 h at room temperature. The reaction mixture was extracted with 50 mL of saturated sodium bicarbonate; the organic layer was separated, dried over sodium sulfate, filtered and evaporated to afford 13a (1.1 g, 2.72 mmol, 68%).

2-Bromo-4-methyl-thiazole-5-carboxylic acid piperidin-4-ylamide hydrochloride 13b 4-[(2-Bromo-4-methyl-thiazole-5-carbonyl)-amino]-piperidine-1-carboxylic acid tert-butyl ester 13a (660 mg, 1.63 mmol) was suspended in cca. 4M HCl in ethyl acetate (20 mL) at ° C. and let to warm up to room temperature. After 3 h stirring, the suspension was evaporated and filtered with diethyl ether to obtain 13b (276 mg, 0.81 mmol, 50%).

2-Bromo-4-methyl-thiazole-5-carboxylic acid (1-methyl-piperidin-4-yl)-amide 13c To a solution of 2-bromo-4-methyl-thiazole-5-carboxylic acid piperidin-4-ylamide hydrochloride 13b (457 mg, 1.34 mmol) in methanol (5 mL), sodium bicarbonate (124 mg, 1.48 mmol), 37% aqueous formaldehyde (1.091 g, 13.5 mmol) and NaBH$_3$CN (101 mg, 1.6 mmol) were added. The reaction was stirred overnight at room temperature, then evaporated. The residue was suspended in saturated sodium bicarbonate and extracted with ethyl acetate. The combined organic phase were dried over sodium sulfate, filtered and evaporated. The residue was purified by column chromatography with chloroform:methanol as eluent, to afford 13c as a solid (250 mg, 0.78 mmol, 58%).

2-(5-Formyl-6-hydroxy-naphthalen-2-yl)-4-methyl-thiazole-5-carboxylic acid (1-methyl-piperidin-4-yl)-amide 13-1

2-hydroxy-6-(4,4,5,5-tetramethyl-[1,3,2]dioxaborolan-2-yl)-naphthalene-1-carbaldehyde (12c, 149 mg, 0.5 mmol), 2-bromo-4-methyl-thiazole-5-carboxylic acid (1-methyl-piperidin-4-yl)-amide 13c (159 mg, 0.5 mmol), sodium carbonate (318 mg, 3 mmol), and tetrakis(triphenylphosphine) palladium (17 mg, 0.015 mmol) were dissolved in a mixture of 5 mL DMF and 5 mL water. The reaction mixture was stirred at 100° C. under argon for 1 h. The reaction mixture was evaporated to dryness and the solid residue was partitioned between dichloromethane and water. The organic phase was separated, and the aqueous layer was extracted once more with chloroform. The combined organic phases were dried over sodium sulfate, filtered and evaporated. The residue was purified by column chromatography with chloroform:methanol as eluent. The crude product was triturated with diethyl ether, filtered off and air dried, affording 13-1 (45 mg, 0.11 mmol, 22%).

LC/MS ESI: M+H=410, Rt: 2.79 min; $^1$H NMR (400 MHz, DMSO-d$_6$) δ ppm 10.70 (s, 1H), 9.09 (d, J=9.0 Hz, 1H), 8.38 (d, J=1.8 Hz, 1H), 8.19 (d, J=7.5 Hz, 1H), 8.13 (d, J=9.3 Hz, 1H), 8.02 (dd, J=8.9, 1.9 Hz, 1H), 7.18 (d, J=9.0 Hz, 1H), 3.72-3.82 (m, 1H), 2.86-2.97 (m, 2H), 2.61 (s, 3H), 2.31 (s, 3H), 2.20-2.29 (m, 2H), 1.79-1.89 (m, 2H), 1.62-1.72 (m, 2H).

The following compounds were made by the above procedure.

| No. | MW | M + H | Rt |
|---|---|---|---|
| 13-1 | 409.5 | 410 | 2.80 |
| 13-2 | 408.5 | 409 | 2.81 |
| 13-3 | 408.5 | 409 | 2.78 |

-continued
| No. | | MW | M + H | Rt |
|---|---|---|---|---|
| 13-4 | 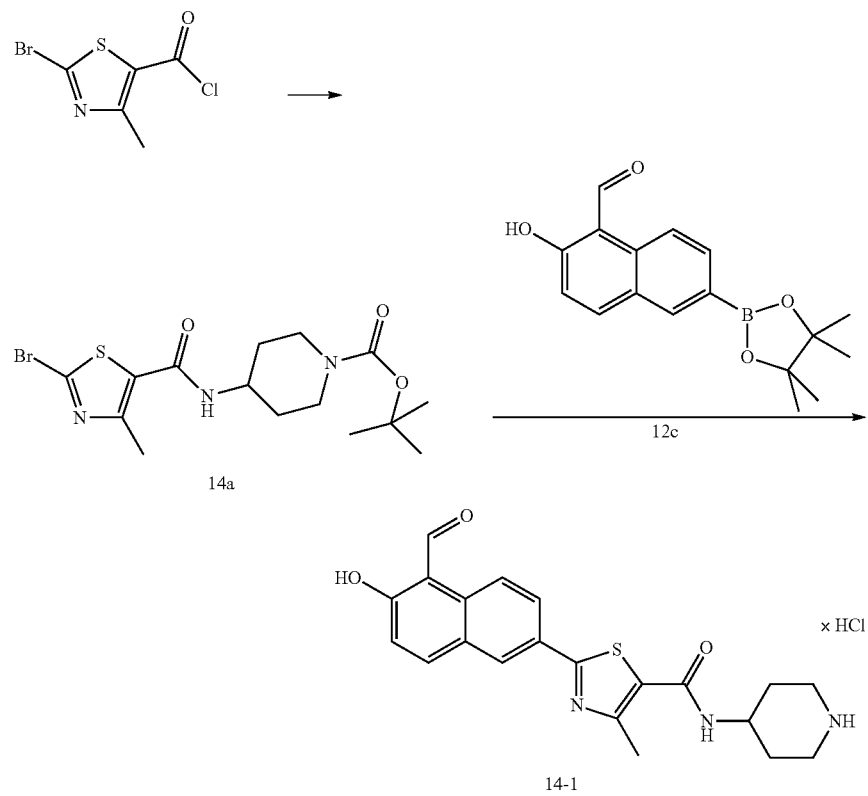 | 394.5 | 395 | 2.76 |
| 13-5 | | 388.5 | 389 | 2.91 |
Example 14
Synthesis of 2-(5-Formyl-6-hydroxy-naphthalen-2-yl)-4-methyl-thiazole-5-carboxylic acid piperidin-4-ylamide hydrochloride 14-1

4-[(2-Bromo-4-methyl-thiazole-5-carbonyl)-amino]piperidine-1-carboxylic acid tert-butyl ester 14a To a stirred mixture of 4-amino-piperidine-1-carboxylic acid tert-butyl ester (801 mg, 4.0 mmol) and diisopropyl-ethyl-amine (517 mg, 4.0 mmol) in 40 mL of abs. dichloromethane at 0° C., 2-bromo-4-methyl-thiazole-5-carbonyl chloride (see Example "Arev"/stepA; 960 mg, 4.0 mmol) in 10 mL of abs. dichloroethane was added dropwise. The mixture was stirred for an additional 2 h at room temperature. The reaction mixture was extracted with 50 mL of saturated sodium bicarbonate; the organic layer was separated, dried over sodium sulfate, filtered and evaporated to afford 14a. (1.1 g, 2.72 mmol, 68%).

2-(5-Formyl-6-hydroxy-naphthalen-2-yl)-4-methyl-thiazole-5-carboxylic acid piperidin-4-ylamide hydrochloride 14-1

2-Hydroxy-6-(4,4,5,5-tetramethyl-[1,3,2]dioxaborolan-2-yl)-naphthalene-1-carbaldehyde 12c (298 mg, 1 mmol), 4-[(2-Bromo-4-methyl-thiazole-5-carbonyl)-amino]-piperidine-1-carboxylic acid tert-butyl ester 14a (404 mg, 1 mmol), sodium carbonate (636 mg, 6 mmol), and tetrakis(triphenylphosphine)palladium (34 mg, 0.03 mmol) were dissolved in a mixture of 9 mL DMF and 9 mL water. The reaction mixture was stirred at 100° C. under argon for 1 h. The reaction mixture was evaporated to dryness and the solid residue was partitioned between chloroform and brine. The organic phase was separated, and the aqueous layer was extracted once more with chloroform. The combined organic phases were dried over sodium sulfate, filtered and evaporated. The residue was purified by column chromatography with chloroform as eluent. The crude product was triturated with diethyl ether, filtered off and air dried. The resulted solid was dissolved in 5 mL methanol, and ethyl acetate containing HCl (2 mL) was added at 0° C. and allowed to reach room temperature. After 3 h stirring, the suspension concentrated under reduced pressure and triturated with diethyl ether to obtain 14-1 (163 mg, 0.38 mmol, 38%).

LC/MS ESI: M+H=396, Rt: 2.80 min; $^1$H NMR (400 MHz, DMSO-$d_6$) δ ppm 12.09 (br. s., 1H), 10.79 (s, 1H), 9.09 (d, J=9.0 Hz, 1H), 8.86-9.06 (m, 2H), 8.50 (d, J=2.0 Hz, 1H), 8.46 (d, J=7.5 Hz, 1H), 8.29 (d, J=9.0 Hz, 1H), 8.11 (dd, J=9.0, 2.0 Hz, 1H), 7.40 (d, J=9.0 Hz, 1H), 3.96-4.10 (m, 1H), 3.29 (d, J=12.8 Hz, 2H), 2.91-3.07 (m, 2H), 2.63 (s, 3H), 1.91-2.07 (m, 2H), 1.72-1.87 (m, 2H).

The following compounds were made by the above procedure:

| No. | | MW | M + H | Rt |
|---|---|---|---|---|
| 14-1 | | 395.5 | 396 | 2.80 |
| 14-2 | | 394.5 | 395 | 2.73 |
| 14-3 | | 394.5 | 395 | 2.00 |

-continued

| No. | | MW | M + H | Rt |
|---|---|---|---|---|
| 14-4 | | 394.5 | 395 | 1.98 |
| 14-5 | | 428.5 | 429 | 1.98 |
| 14-6 | | 380.5 | 381 | 2.89 |
| 14-7 | | 380.5 | 381 | 2.68 |
| 14-8 | | 374.4 | 375.2 | 2.90 |

-continued
| No. | | MW | M + H | Rt |
|---|---|---|---|---|
| 14-9 | 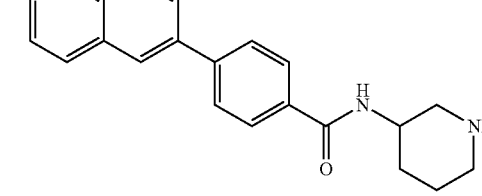 | 374.4 | 375 | 2.71 |
| 14-10 | 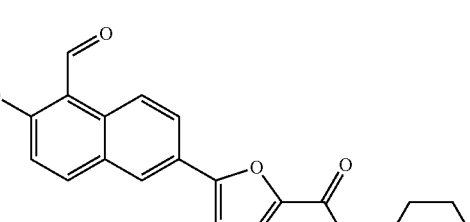 | 364.4 | 365 | 2.67 |
| 14-11 | 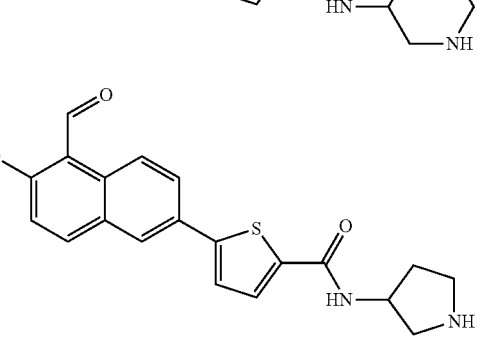 | 366.4 | 367 | 2.63 |
| 14-12 | 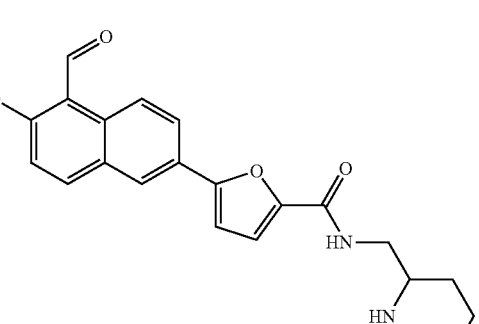 | 378.4 | 379 | 2.69 |
| 14-13 | 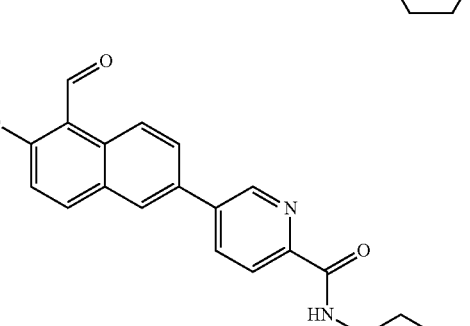 | 375.4 | 376 | 2.82 |

Example 15

Synthesis of 2-Hydroxy-6-(3-morpholin-4-yl-3-oxo-propenyl)-naphthalene-1-carbaldehyde 15-3

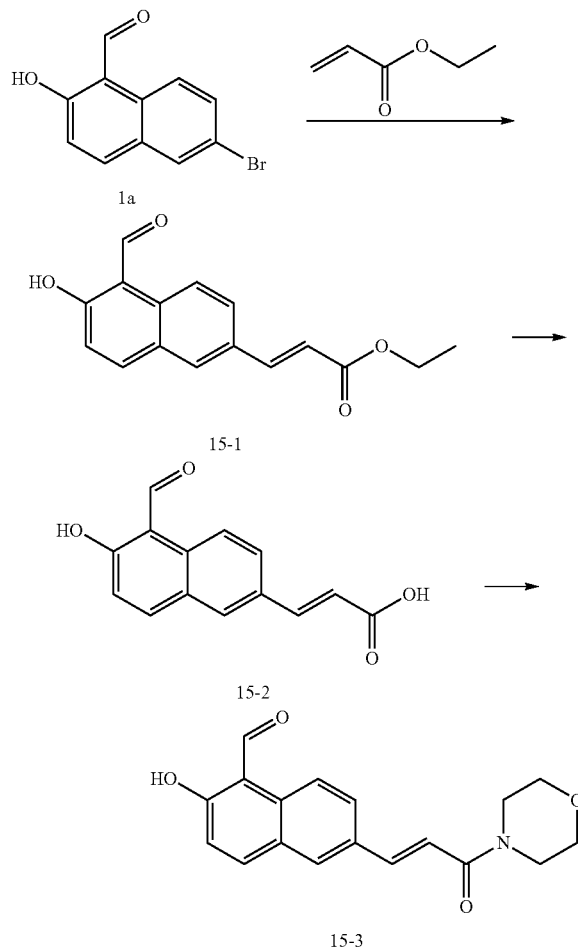

3-(5-formyl-6-hydroxy-naphthalen-2-yl)-acrylic acid ethyl ester 15-1

To a solution of 6-bromo-2-hydroxy-naphthalene-1-carbaldehyde 1a (1 g, 4 mmol) in 4 mL dimethylformamide, ethyl acrylate (521 µL, 4.8 mmol), triethylamine (780 µL, 5.6 mmol) and tetrakis(triphenylphosphine)palladium (23 mg, 0.02 mmol) were added and the mixture was stirred under nitrogen at 100° C. for 1 h. The solvent was evaporated under reduced pressure, then the residue was suspended in water (500 mL) and extracted with dichloromethane (2×50 mL). The combined organic layers were dried over magnesium sulfate and evaporated to dryness. The crude product was purified by column chromatography on silica gel, eluting with toluene to afford 15-1 as a yellow solid (600 mg, 2.22 mmol, 55%).

LC/MS ESI: M+H=271, Rt: 3.18 min; $^1$H NMR (400 MHz, CDCl$_3$) δ ppm 13.17 (s, 1H), 10.81 (s, 1H), 8.36 (d, J=8.8 Hz, 1H), 8.00 (d, J=9.0 Hz, 1H), 7.89 (s, 1H), 7.74-7.84 (m, 2H), 7.18 (d, J=9.0 Hz, 1H), 6.54 (d, J=15.8 Hz, 1H), 4.30 (q, J=7.0 Hz, 2H), 1.36 (t, J=7.2 Hz, 3H).

3-(5-Formyl-6-hydroxy-naphthalen-2-yl)-acrylic acid 15-2

3-(5-Formyl-6-hydroxy-naphthalen-2-yl)-acrylic acid ethyl ester 15-1 (534 mg; 1.97 mmol) was dissolved in a mixture 25 mL of dioxane and 20 mL of 1N sodium hydroxide and was heated to 50° C. for 0.5 h. The reaction mixture was extracted with 30 mL of chloroform and the aqueous layer was cooled to 0° C. and 6N hydrochloric acid was added dropwise. The precipitated solid was filtered, washed with distilled water to afford 15-2. (418 mg, 1.55 mmol, 87%).

$^1$H NMR (400 MHz, DMSO-d$_6$) δ ppm 12.39 (br. s., 1H), 12.04 (s, 1H), 10.79 (s, 1H), 8.95 (d, J=9.0 Hz, 1H), 8.10-8.22 (m, 2H), 7.96 (dd, J=8.9, 1.6 Hz, 1H), 7.69 (d, J=16.1 Hz, 1H), 7.29 (d, J=9.0 Hz, 1H), 6.63 (d, J=15.8 Hz, 1H).

2-Hydroxy-6-(3-morpholin-4-yl-3-oxo-propenyl)-naphthalene-1-carbaldehyde 15-3

3-(5-Formyl-6-hydroxy-naphthalen-2-yl)-acrylic acid 15-2 (73 mg, 0.3 mmol), 1-hydroxybenzotriazole (89 mg, 0.66 mmol), morpholine (58 mg, 0.66 mmol) and triethylamine (151 mg, 1.5 mmol) were dissolved in 5 mL THF. 1-Ethyl-3-(3-dimethylaminopropyl)carbodiimide hydrochloride (127 mg, 0.66 mmol) was added with stirring at room temperature. After 2 h, 5 mL of 2N aqueous hydrochloric acid was added and the mixture was stirred for an additional 2 h. The reaction mixture was evaporated to dryness and the solid residue was partitioned between 15 mL of chloroform and 15 mL of saturated sodium bicarbonate. The aqueous phase was extracted with an additional 15 mL portion of chloroform; the combined organic phases were extracted with brine, dried over sodium sulfate, filtered off and evaporated. The solid material was purified by chromatography on silica, with chloroform as eluent to afford 15-3. (50 mg, 0.16 mmol, 54%).

$^1$H NMR (400 MHz, CDCl$_3$) δ ppm 13.14 (br. s., 1H), 10.81 (s, 1H), 8.34 (d, J=8.8 Hz, 1H), 8.00 (d, J=9.0 Hz, 1H), 7.89 (s, 1H), 7.82 (d, J=15.6 Hz, 1H), 7.80 (d, J=7.0 Hz, 1H), 7.18 (d, J=9.0 Hz, 1H), 6.95 (d, J=15.3 Hz, 1H), 3.75 (br. s., 8H).

The following compounds were made by the above procedure.

| No. | | NMR |
|---|---|---|
| 15-1 | (structure) | $^1$H NMR (400 MHz, CDCl$_3$) δ ppm 13.17 (s, 1H), 10.81 (s, 1H), 8.36 (d, J = 8.8 Hz, 1H), 8.00 (d, J = 9.0 Hz, 1H), 7.89 (s, 1H), 7.74-7.84 (m, 2H), 7.18 (d, J = 9.0 Hz, 1H), 6.54 (d, J = 15.8 Hz, 1H), 4.30 (q, J = 7.0 Hz, 2H), 1.36 (t, J = 7.2 Hz, 3H). |

-continued

| No. | | NMR |
|---|---|---|
| 15-2 | ![structure] | ¹H NMR (400 MHz, DMSO-d₆) δ ppm 12.39 (br. s., 1H), 12.04 (s, 1H), 10.79 (s, 1H), 8.95 (d, J = 9.0 Hz, 1H), 8.10-8.22 (m, 2H), 7.96 (dd, J = 8.9, 1.6 Hz, 1H), 7.69 (d, J = 16.1 Hz, 1H), 7.29 (d, J = 9.0 Hz, 1H), 6.63 (d, J = 15.8 Hz, 1H) |
| 15-3 | ![structure] | ¹H NMR (400 MHz, CDCl₃) δ ppm 13.14 (br. s., 1H), 10.81 (s, 1H), 8.34 (d, J = 8.8 Hz, 1H), 8.00 (d, J = 9.0 Hz, 1H), 7.89 (s, 1H), 7.82 (d, J = 15.6 Hz, 1H), 7.80 (d, J = 7.0 Hz, 1H), 7.18 (d, J = 9.0 Hz, 1H), 6.95 (d, J = 15.3 Hz, 1H), 3.75 (br. s., 8H). |
| 15-4 | ![structure] | ¹H NMR (400 MHz, CDCl₃) δ ppm 13.14 (s, 1H), 10.81 (s, 1H), 8.34 (d, J = 8.8 Hz, 1H), 8.00 (d, J = 9.3 Hz, 1H), 7.89 (d, J = 1.5 Hz, 1H), 7.74-7.84 (m, 2H), 7.17 (d, J = 9.0 Hz, 1H), 7.00 (d, J = 15.6 Hz, 1H), 3.22 (s, 3H), 3.10 (s, 3H). |
| 15-5 | ![structure] | MW, 324.1, M + 1 325 |

2-Hydroxy-6-(3-morpholin-4-yl-3-oxo-propyl)-naphthalene-1-carbaldehyde 16-3

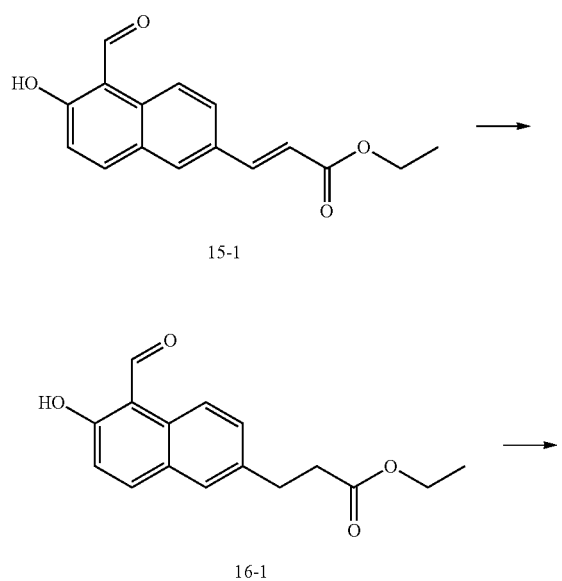

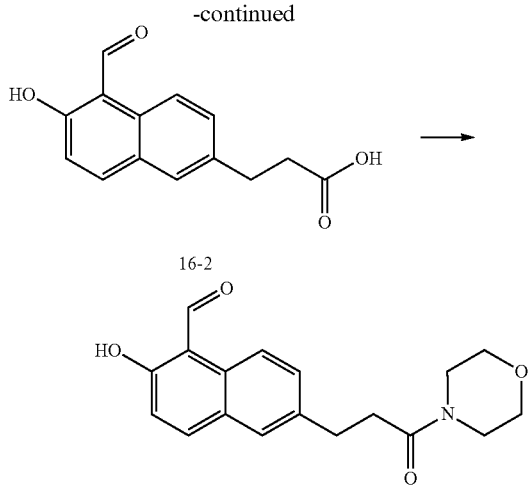

3-(5-Formyl-6-hydroxy-naphthalen-2-yl)-acrylic acid ethyl ester (15-1, 570 mg, 2.11 mmol) was dissolved in 10 mL ethyl acetate and 50 mg of Pd/C (10%) was added. The mixture was stirred at room temperature for 72 h under hydrogen atmosphere. The catalyst was filtered off, and the filtrate was evaporated under reduced pressure. The obtained tawny oil was purified by column chromatography on silica gel, eluting with a 98:2 mixture of toluene:methanol to afford 16-1 as a solid (212 mg, 0.78 mmol, 37%).

LC/MS ESI: M+H=273, Rt: 3.72 min; $^1$H NMR (400 MHz, CDCl$_3$) δ ppm 13.06 (s, 1H), 10.80 (s, 1H), 8.28 (d, J=8.5 Hz, 1H), 7.92 (d, J=9.0 Hz, 1H), 7.61 (s, 1H), 7.49 (dd, J=8.8, 1.5 Hz, 1H), 7.13 (d, J=9.0 Hz, 1H), 4.13 (q, J=7.0 Hz, 2H), 3.10 (t, J=7.7 Hz, 2H), 2.71 (t, J=7.7 Hz, 2H), 1.23 (t, J=7.2 Hz, 3H).

3-(5-Formyl-6-hydroxy-naphthalen-2-yl)-propionic acid ethyl ester 16-1 (158 mg, 0.58 mmol) was added to 50 mL of a 1:1 mixture of dioxane-sodium hydroxide (10%) and stirred for 30 min at room temperature. 50 mL Dichloromethane was added, the aqueous layer was separated and washed with 50 mL of dichloromethane. The aqueous layer was acidified with 1N hydrochloric acid, and the precipitate was filtered and washed three times with water., then dried under an infrared lamp to afford 16-2 as a solid (94 mg, 0.39 mmol, 63%).

LC/MS ESI: M+H=245, Rt: 2.28 min; $^1$H NMR (400 MHz, DMSO-d$_6$) δ ppm 12.14 (br. s., 1H), 11.89 (br. s., 1H), 10.79 (s, 1H), 8.83 (d, J=8.8 Hz, 1H), 8.06 (d, J=9.0 Hz, 1H), 7.70 (s, 1H), 7.52 (dd, J=8.9, 1.6 Hz, 1H), 7.21 (d, J=9.0 Hz, 1H), 2.95 (t, J=7.5 Hz, 2H), 2.62 (t, J=7.5 Hz, 2H).

3-(5-Formyl-6-hydroxy-naphthalen-2-yl)-propionic acid 16-2 (150 mg, 0.67 mmol), 1-hydroxybenzotriazole (109 mg, 0.8 mmol), morpholine (64 mg, 0.74 mmol), triethylamine (270 mg, 2.68 mmol) and 1-ethyl-3-(3-dimethylaminopropyl) carbodiimide hydrochloride (153 mg, 0.8 mmol) were dissolved in dimethylformamide (4 mL), and the mixture was stirred overnight at room temperature. The solvent was evaporated under reduced pressure, 30 mL 1N hydrochloric acid was added and the suspension was extracted with chloroform (2×30 mL), then the combined organic layers were washed with 30 mL saturated sodium bicarbonate. The organic layer was dried over magnesium sulfate and evaporated to dryness. The crude product was purified by preparative HPLC to afford 16-3 (26 mg, 83 μmol, 14%).

LC/MS ESI: M+H=314, Rt: 2.92 min; $^1$H NMR (400 MHz, DMSO-d$_6$) δ ppm 11.95 (br. s., 1H), 10.79 (s, 1H), 8.83 (d, J=8.8 Hz, 1H), 8.05 (d, J=9.0 Hz, 1H), 7.71 (s, 1H), 7.53 (dd, J=8.8, 1.5 Hz, 1H), 7.20 (d, J=9.0 Hz, 1H), 3.45-3.53 (m, 4H), 3.39-3.45 (m, 4H), 2.95 (t, J=7.7 Hz, 2H), 2.70 (t, J=7.7 Hz, 2H).

The following compounds were made by the above procedure:

| No. | | MW | M + H | Rt |
|---|---|---|---|---|
| 16-1 | ethyl 3-(5-formyl-6-hydroxy-naphthalen-2-yl)propanoate | 272.3 | 273 | 3.75 |
| 16-2 | 3-(5-formyl-6-hydroxy-naphthalen-2-yl)propanoic acid | 244.3 | 245 | 2.28 |
| 16-3 | 3-(5-formyl-6-hydroxy-naphthalen-2-yl)-1-morpholinopropan-1-one | 313.4 | 314 | 2.92 |
| 16-4 | 3-(5-formyl-6-hydroxy-naphthalen-2-yl)-N,N-dimethylpropanamide | 271.3 | 272 | 2.99 |

Example 17

Synthesis of 4-Chloro-3-(5-formyl-6-hydroxy-naphthalen-2-yl)-benzoic acid 17-1

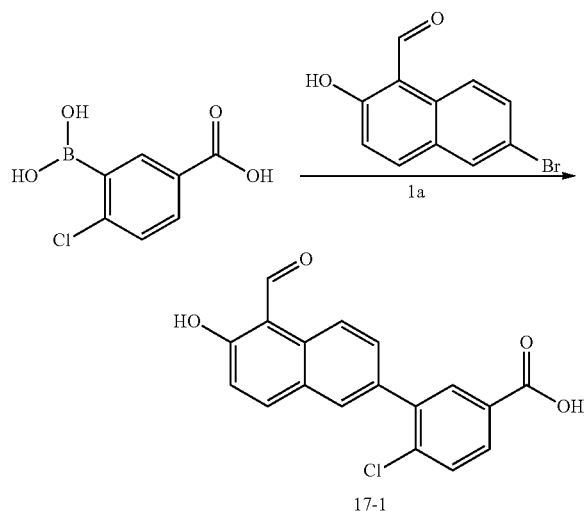

4-Chloro-3-(5-formyl-6-hydroxy-naphthalen-2-yl)-benzoic acid 17-1

6-Bromo-2-hydroxy-naphthalene-1-carbaldehyde 1a (1.5 g, 6.0 mmol), 2-chloro-5-carboxyphenylboronic acid (1.36 g, 6.6 mmol), sodium carbonate (660 mg, 36 mmol), and tetrakis(triphenylphosphine)palladium (200 mg, 0.17 mmol) were dissolved in a mixture of 100 mL DMF and 100 mL water. The reaction mixture was stirred at 100° C. under argon for 6 h. The reaction mixture was extracted two times with 150 mL 1N sodium hydroxide. The combined aqueous phases were extracted three times with 50 mL of chloroform. The aqueous layer was separated, cooled to 0° C., and was stirred vigorously, while 5N hydrochloric acid was added dropwise. The precipitated white solid was filtered, washed with water and diethyl ether. A 100 mg portion of the crude product was purified by chromatography on silica eluting with 95:5 chloroform/methanol to afford analytically pure 17-1. (59 mg, 0.18 mmol, 44%).

$^1$H NMR (400 MHz, DMSO-$d_6$) δ ppm 13.38 (br. s., 1H), 12.04 (br. s., 1H), 10.84 (s, 1H), 9.03 (d, J=9.0 Hz, 1H), 8.23 (d, J=9.0 Hz, 1H), 8.02 (d, J=2.0 Hz, 1H), 8.00 (d, J=1.8 Hz, 1H), 7.96 (dd, J=8.3, 2.0 Hz, 1H), 7.75 (d, J=8.3 Hz, 1H), 7.73 (dd, J=9.0, 2.0 Hz, 1H), 7.31 (d, J=9.0 Hz, 1H).

The following compounds were made by the above procedure:

| No. | | NMR |
|---|---|---|
| 17-1 | (structure) | $^1$H NMR (400 MHz, DMSO-$d_6$) δ ppm 13.38 (br. s., 1H), 12.04 (br. s., 1H), 10.84 (s, 1H), 9.03 (d, J = 9.0 Hz, 1H), 8.23 (d, J = 9.0 Hz, 1H), 8.02 (d, J = 2.0 Hz, 1H), 8.00 (d, J = 1.8 Hz, 1H), 7.96 (dd, J = 8.3, 2.0 Hz, 1H), 7.75 (d, J = 8.3 Hz, 1H), 7.73 (dd, J = 9.0, 2.0 Hz, 1H), 7.31 (d, J = 9.0 Hz, 1H). |
| 17-2 | (structure) | $^1$H NMR (400 MHz, DMSO-$d_6$) δ ppm 12.34 (br. s., 1H), 10.93 (s, 1H), 9.20-9.31 (m, 4H), 8.22 (d, J = 8.8 Hz, 1H), 8.07 (d, J = 8.3 Hz, 1H), 7.87 (dd, J = 8.4, 1.9 Hz, 1H), 7.30 (d, J = 9.0 Hz, 1H). |
| 17-3 | (structure) | $^1$H NMR (400 MHz, DMSO-$d_6$) δ ppm 13.43 (br. s., 1H), 12.01 (br. s., 1H), 10.84 (s, 1H), 9.04 (d, J = 9.0 Hz, 1H), 8.22 (d, J = 9.0 Hz, 1H), 8.06 (d, J = 1.5 Hz, 1H), 8.02 (d, J = 2.0 Hz, 1H), 7.99 (dd, J = 8.0, 1.8 Hz, 1H), 7.73 (dd, J = 8.8, 2.0 Hz, 1H), 7.66 (d, J = 7.8 Hz, 1H), 7.31 (d, J = 9.0 Hz, 1H). |

Example 18

Synthesis of 5-(5-Formyl-6-hydroxy-naphthalen-2-yl)-4-methyl-thiophene-2-carboxylic acid 18-1

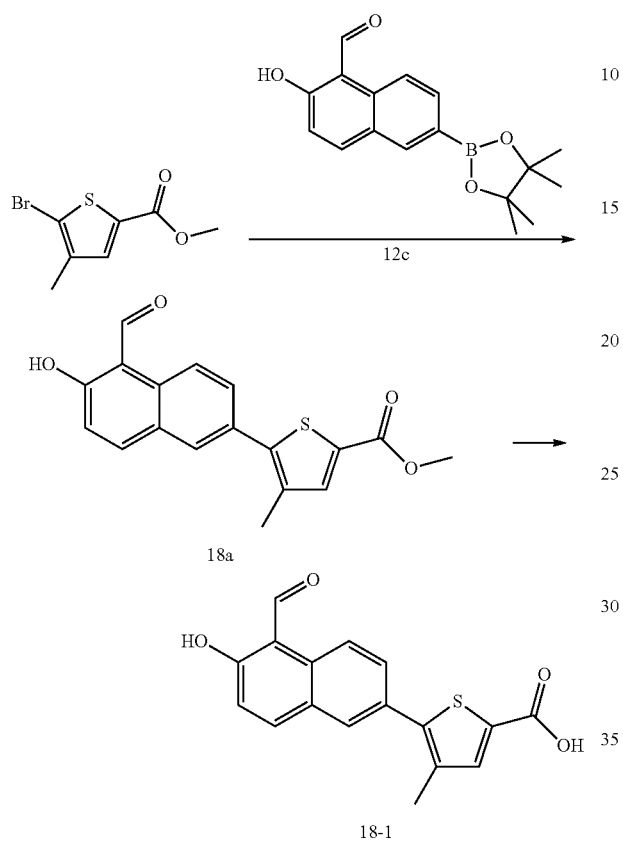

5-(5-Formyl-6-hydroxy-naphthalen-2-yl)-4-methyl-thiophene-2-carboxylic acid methyl ester 18a 2-Hydroxy-6-(4,4,5,5-tetramethyl-[1,3,2]dioxaborolan-2-yl)-naphthalene-1-carbaldehyde 12c (1.20 g, 4.0 mmol), 5-bromo-4-methyl-thiophene-2-carboxylic acid methyl ester (1.03 g, 4.40 mmol), sodium carbonate (2.54 g, 24.0 mmol), and tetrakis(triphenylphosphine)palladium (138 mg, 0.12 mmol) were dissolved in a mixture of 100 mL DMF and 100 mL water. The reaction mixture was stirred at 105° C. under argon for 3 h. The reaction mixture was evaporated to dryness and the solid residue was partitioned between chloroform and water, while the aqueous phase was acidified with acetic acid to pH 6. The organic phase was separated, and the aqueous layer was extracted once more with chloroform. The combined organic phases were dried over sodium sulfate, filtered and evaporated. The obtained crude product 18a (900 mg, 2.76 mmol, 96%) was used in the next step without purification.

5-(5-Formyl-6-hydroxy-naphthalen-2-yl)-4-methyl-thiophene-2-carboxylic acid 18-1

5-(5-Formyl-6-hydroxy-naphthalen-2-yl)-4-methyl-thiophene-2-carboxylic acid methyl ester 18a (835 mg; 2.56 mmol) was dissolved in a mixture 30 mL of dioxane and 30 mL of 1N sodium hydroxide and was stirred at 50° C. for 1 h. Charcoal was added to the mixture and was stirred for an additional 0.5 h, then filtered. The reaction mixture was washed with 30 mL of chloroform, the aqueous layer was cooled to 0° C. and 6N hydrochloric acid was added dropwise. The precipitating solid was filtered, washed with distilled water to afford 18-1. (675 mg, 2.16 mmol, 84%).

$^1$H NMR (400 MHz, DMSO-$d_6$) δ ppm 13.07 (br. s., 1H), 11.99 (s, 1H), 10.81 (s, 1H), 9.04 (d, J=8.8 Hz, 1H), 8.23 (d, J=8.8 Hz, 1H), 8.07 (d, J=2.0 Hz, 1H), 7.77 (dd, J=8.8, 2.0 Hz, 1H), 7.65 (s, 1H), 7.31 (d, J=9.0 Hz, 1H), 2.36 (s, 3H).

Example 19

Synthesis of 6-[2-Chloro-5-(morpholine-4-carbonyl)-phenyl]-2-hydroxy-naphthalene-1-carbaldehyde 19-1

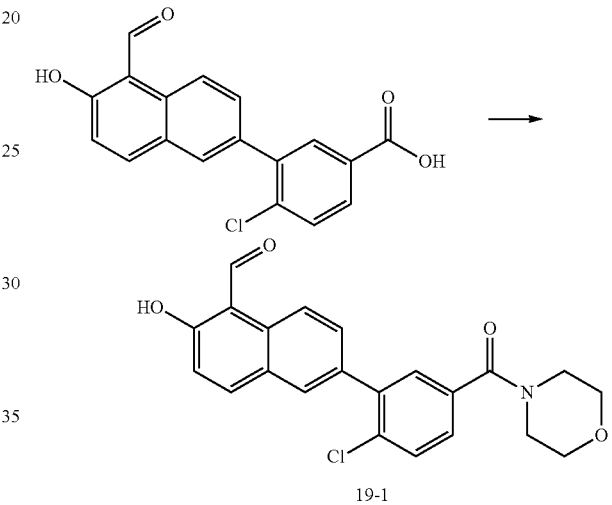

6-[2-Chloro-5-(morpholine-4-carbonyl)-phenyl]-2-hydroxy-naphthalene-1-carbaldehyde 19-1

Crude 5-chloro-6-(5-formyl-6-hydroxy-naphthalen-2-yl)-pyridine-2-carboxylic acid (see Example "O1"; 98 mg, 0.3 mmol), 1-hydroxybenzotriazole (89 mg, 0.66 mmol), 2-methoxy-ethylamine (57 mg, 0.66 mmol) and triethylamine (151 mg, 1.5 mmol) were dissolved in 5 mL of THF. 1-Ethyl-3-(3-dimethylaminopropyl)carbodiimide hydrochloride (127 mg, 0.66 mmol) was added to the stirred solution at room temperature. After 2 h, 5 mL of 2N aqueous hydrochloric acid was added and the mixture was stirred for an additional 2 h. The reaction mixture was evaporated to dryness and the solid residue was partitioned between 15 mL of chloroform and 15 mL of saturated sodium bicarbonate. The aqueous phase was extracted with an additional 15 mL portion of chloroform; the combined organic phases were extracted with brine, dried over sodium sulfate, filtered off and evaporated. The solid material was crystallized with 2-propanol to afford 19-1. (66 mg, 0.15 mmol, 56%).

$^1$H NMR (400 MHz, CDCl$_3$) δ ppm 13.17 (s, 1H), 10.86 (s, 1H), 8.43 (d, J=9.0 Hz, 1H), 8.03 (d, J=9.0 Hz, 1H), 7.87 (d, J=2.0 Hz, 1H), 7.73 (dd, J=8.7, 1.9 Hz, 1H), 7.57 (d, J=8.3 Hz, 1H), 7.51 (d, J=2.0 Hz, 1H), 7.37 (dd, J=8.2, 2.1 Hz, 1H), 7.20 (d, J=9.0 Hz, 1H), 3.72 (br. s., 8H).

The following compounds were made by the above procedure:

| No. | | NMR |
|---|---|---|
| 19-1 | | ¹H NMR (400 MHz, CDCl₃) δ ppm 13.17 (s, 1H), 10.86 (s, 1H), 8.43 (d, J = 9.0 Hz, 1H), 8.03 (d, J = 9.0 Hz, 1H), 7.87 (d, J = 2.0 Hz, 1H), 7.73 (dd, J = 8.7, 1.9 Hz, 1H), 7.57 (d, J = 8.3 Hz, 1H), 7.51 (d, J = 2.0 Hz, 1H), 7.37 (dd, J = 8.2, 2.1 Hz, 1H), 7.20 (d, J = 9.0 Hz, 1H), 3.72 (br. s., 8H). |
| 19-2 | | ¹H NMR (400 MHz, CDCl₃) δ ppm 13.11 (br. s., 1H), 10.85 (s, 1H), 8.44 (d, J = 8.8 Hz, 1H), 8.15 (t, J = 1.8 Hz, 1H), 8.01-8.08 (m, 2H), 7.90 (dd, J = 8.8, 2.0 Hz, 1H), 7.82 (ddd, J = 7.8, 1.8, 1.3 Hz, 1H), 7.75 (d, J = 8.0 Hz, 1H), 7.55 (t, J = 7.8 Hz, 1H), 7.19 (d, J = 9.0 Hz, 1H), 6.62 (br. s., 1H), 3.68-3.74 (m, 2H), 3.60 (t, J = 5.3 Hz, 2H), 3.41 (s, 3H). |
| 19-3 | | ¹H NMR (400 MHz, CDCl₃) δ ppm 13.14 (s, 1H), 10.85 (s, 1H), 8.43 (d, J = 8.5 Hz, 1H), 8.13-8.17 (m, 1H), 8.02-8.07 (m, 2H), 7.90 (dd, J = 8.8, 2.0 Hz, 1H), 7.81 (d, J = 7.8 Hz, 1H), 7.75 (d, J = 7.8 Hz, 1H), 7.54 (t, J = 7.8 Hz, 1H), 7.19 (d, J = 9.3 Hz, 1H), 6.56 (br. s., 1H), 3.06 (d, J = 4.8 Hz, 3H). |
| 19-4 | | ¹H NMR (400 MHz, CDCl₃) δ ppm 13.15 (s, 1H), 10.85 (s, 1H), 8.44 (d, J = 9.3 Hz, 1H), 8.06 (d, J = 9.3 Hz, 1H), 8.03 (d, J = 2.0 Hz, 1H), 7.87-7.94 (m, 3H), 7.76 (d, J = 8.8 Hz, 2H), 7.20 (d, J = 9.0 Hz, 1H), 6.59 (t, J = 4.8 Hz, 1H), 3.67-3.74 (m, 2H), 3.60 (t, J = 5.3 Hz, 2H), 3.42 (s, 3H). |
| 19-5 | | ¹H NMR (400 MHz, DMSO-d₆) δ ppm 10.82 (s, 1H), 9.09 (d, J = 9.0 Hz, 1H), 8.94 (t, J = 6.0 Hz, 1H), 8.79 (d, J = 2.0 Hz, 1H), 8.56 (dd, J = 9.0, 2.0 Hz, 1H), 8.28 (dd, J = 8.0, 1.0 Hz, 1H), 8.22 (d, J = 9.0 Hz, 1H), 8.08 (t, J = 7.8 Hz, 1H), 7.99 (dd, J = 7.7, 0.9 Hz, 1H), 7.27 (d, J = 9.0 Hz, 1H), 3.32-3.39 (m, 2H), 1.55-1.70 (m, 2H), 0.93 (t, J = 7.4 Hz, 3H). |
| 19-6 | | ¹H NMR (400 MHz, DMSO-d₆) δ ppm 11.97 (br. s., 1H), 10.84 (s, 1H), 9.02 (d, J = 8.8 Hz, 1H), 8.21 (d, J = 9.3 Hz, 1H), 8.00 (s, 1H), 7.73 (d, J = 8.8 Hz, 1H), 7.67 (d, J = 8.0 Hz, 1H), 7.52 (d, J = 1.3 Hz, 1H), 7.47 (d, J = 8.3 Hz, 1H), 7.30 (d, J = 9.0 Hz, 1H), 2.98 (br. s., 6H). |

| No. | | NMR |
|---|---|---|
| 19-7 | 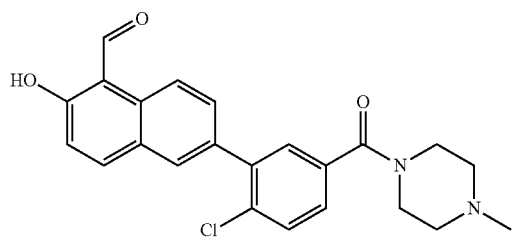 [SMILES: CN1CCN(C(=O)c2ccc(Cl)c(-c3ccc4c(C=O)c(O)ccc4c3)c2)CC1] | ¹H NMR (400 MHz, DMSO-d₆) δ ppm 12.09 (br. s., 1H), 10.83 (s, 1H), 9.02 (d, J = 9.0 Hz, 1H), 8.20 (d, J = 9.0 Hz, 1H), 7.99 (d, J = 2.0 Hz, 1H), 7.72 (dd, J = 9.0, 2.0 Hz, 1H), 7.67 (d, J = 8.3 Hz, 1H), 7.49 (d, J = 1.8 Hz, 1H), 7.44 (dd, J = 8.2, 2.1 Hz, 1H), 7.29 (d, J = 9.0 Hz, 1H), 3.60 (br. s., 4H), 2.33 (br. s., 4H), 2.19 (s, 3H). |
| 19-8 | 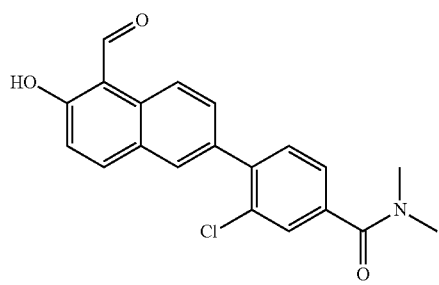 [SMILES: CN(C)C(=O)c1ccc(-c2ccc3c(C=O)c(O)ccc3c2)c(Cl)c1] | ¹H NMR (400 MHz, DMSO-d₆) δ ppm 12.05 (br. s., 1H), 10.83 (s, 1H), 9.03 (d, J = 8.8 Hz, 1H), 8.21 (d, J = 9.0 Hz, 1H), 8.00 (d, J = 2.0 Hz, 1H), 7.72 (dd, J = 8.8, 2.0 Hz, 1H), 7.63 (d, J = 1.5 Hz, 1H), 7.58 (d, J = 7.8 Hz, 1H), 7.49 (dd, J = 7.9, 1.6 Hz, 1H), 7.30 (d, J = 9.0 Hz, 1H), 3.00 (br. s., 6H). |
| 19-9 | 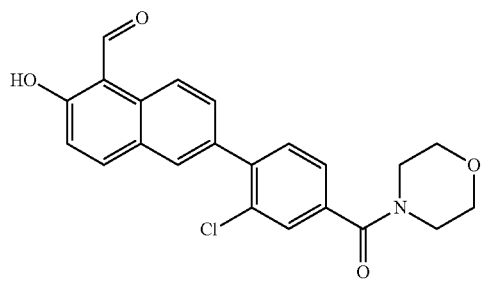 [SMILES: O=Cc1c(O)ccc2cc(-c3ccc(C(=O)N4CCOCC4)cc3Cl)ccc12] | ¹H NMR (400 MHz, DMSO-d₆) δ ppm 12.00 (br. s., 1H), 10.84 (s, 1H), 9.03 (d, J = 8.8 Hz, 1H), 8.21 (d, J = 9.0 Hz, 1H), 7.99 (d, J = 2.0 Hz, 1H), 7.72 (dd, J = 8.8, 2.0 Hz, 1H), 7.65 (d, J = 1.5 Hz, 1H), 7.59 (d, J = 7.8 Hz, 1H), 7.50 (dd, J = 7.8, 1.5 Hz, 1H), 7.30 (d, J = 9.0 Hz, 1H), 3.64 (br. s., 6H), 3.45 (br. s., 2H). |
| 19-10 | 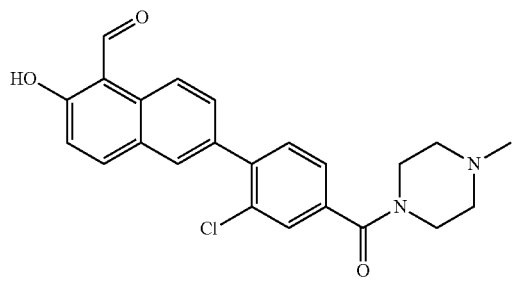 [SMILES: CN1CCN(C(=O)c2ccc(-c3ccc4c(C=O)c(O)ccc4c3)c(Cl)c2)CC1] | ¹H NMR (400 MHz, DMSO-d₆) δ ppm 11.86 (br. s., 1H), 10.84 (s, 1H), 9.03 (d, J = 8.8 Hz, 1H), 8.21 (d, J = 9.0 Hz, 1H), 8.00 (d, J = 2.0 Hz, 1H), 7.72 (dd, J = 8.8, 2.0 Hz, 1H), 7.62 (d, J = 1.8 Hz, 1H), 7.59 (d, J = 7.8 Hz, 1H), 7.47 (dd, J = 7.8, 1.6 Hz, 1H), 7.30 (d, J = 9.0 Hz, 1H), 3.65 (br. s., 2H), 3.41 (br. s., 2H), 2.38 (br. s., 4H), 2.25 (s, 3H). |
| 19-11 | 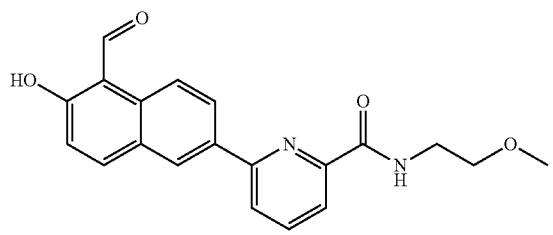 [SMILES: COCCNC(=O)c1cccc(-c2ccc3c(C=O)c(O)ccc3c2)n1] | ¹H NMR (400 MHz, CDCl₃) δ ppm 13.20 (s, 1H), 10.87 (s, 1H), 8.41-8.54 (m, 3H), 8.31 (dd, J = 8.8, 2.0 Hz, 1H), 8.20 (dd, J = 6.7, 2.1 Hz, 1H), 8.11 (d, J = 9.3 Hz, 1H), 7.93-8.01 (m, 2H), 7.22 (d, J = 9.0 Hz, 1H), 3.72-3.79 (m, 2H), 3.64 (t, J = 5.3 Hz, 1H), 3.45 (s, 3H). |

-continued

| No. | | NMR |
|---|---|---|
| 19-12 | | $^1$H NMR (400 MHz, DMSO-d$_6$) δ ppm 12.00 (br. s., 1H), 10.83 (s, 1H), 9.04 (d, J = 8.8 Hz, 1H), 8.49 (q, J = 4.5 Hz, 1H), 8.30 (d, J = 1.8 Hz, 1H), 8.23 (d, J = 9.0 Hz, 1H), 8.02 (dd, J = 9.0, 2.0 Hz, 1H), 7.97 (d, J = 8.3 Hz, 2H), 7.91 (d, J = 8.3 Hz, 2H), 7.30 (d, J = 9.0 Hz, 1H), 2.82 (d, J = 4.5 Hz, 3H) |
| 19-13 | | $^1$H NMR (400 MHz, CDCl$_3$) δ ppm 13.18 (s, 1H), 10.84 (s, 1H), 8.41-8.49 (m, 2H), 8.38 (s, 1H), 8.19-8.30 (m, 2H), 8.08 (d, J = 9.0 Hz, 1H), 7.93-8.02 (m, 2H), 7.35 (d, J = 8.3 Hz, 2H), 7.20 (d, J = 9.0 Hz, 1H), 6.90 (d, J = 8.3 Hz, 2H), 4.69 (d, J = 6.0 Hz, 2H), 3.80 (s, 3H). |
| 19-14 | | $^1$H NMR (400 MHz, CDCl$_3$) δ ppm 13.19 (s, 1H), 10.87 (s, 1H), 8.48 (d, J = 9.0 Hz, 1H), 8.42 (d, J = 1.8 Hz, 1H), 8.29 (dd, J = 8.9, 1.9 Hz, 1H), 8.14-8.24 (m, 2H), 8.12 (d, J = 9.0 Hz, 1H), 7.94-8.00 (m, 2H), 7.22 (d, J = 9.0 Hz, 1H), 3.12 (d, J = 5.0 Hz, 3H). |
| 19-15 | | $^1$H NMR (400 MHz, DMSO-d$_6$) δ ppm 11.96 (br. s., 1H), 10.80 (s, 1H), 8.99 (d, J = 9.0 Hz, 1H), 8.47 (q, J = 4.5 Hz, 1H), 8.22 (d, J = 2.0 Hz, 1H), 8.20 (d, J = 9.0 Hz, 1H), 7.96 (dd, J = 8.9, 2.1 Hz, 1H), 7.72 (d, J = 3.8 Hz, 1H), 7.62 (d, J = 3.8 Hz, 1H), 7.29 (d, J = 9.0 Hz, 1H), 2.79 (d, J = 4.5 Hz, 3H). |
| 19-16 | | $^1$H NMR (400 MHz, DMSO-d$_6$) δ ppm 11.98 (br. s., 1H), 10.79 (s, 1H), 8.99 (d, J = 9.0 Hz, 1H), 8.58 (t, J = 5.4 Hz, 1H), 8.23 (d, J = 2.0 Hz, 1H), 8.20 (d, J = 9.0 Hz, 1H), 7.96 (dd, J = 8.9, 2.1 Hz, 1H), 7.80 (d, J = 4.0 Hz, 1H), 7.63 (d, J = 4.0 Hz, 1H), 7.28 (d, J = 9.0 Hz, 1H), 3.40-3.48 (m, 4H), 3.28 (s, 3H). |
| 19-17 | | $^1$H NMR (400 MHz, DMSO-d$_6$) δ ppm 12.00 (br. s., 1H), 10.81 (s, 1H), 9.03 (d, J = 9.0 Hz, 1H), 8.22 (d, J = 9.0 Hz, 1H), 8.04 (d, J = 2.0 Hz, 1H), 7.75 (dd, J = 8.8, 2.0 Hz, 1H), 7.37 (s, 1H), 7.30 (d, J = 9.0 Hz, 1H), 3.67-3.74 (m, 4H), 3.61-3.67 (m, 4H), 2.35 (s, 3H). |

-continued

| No. | NMR |
|---|---|
| 19-18 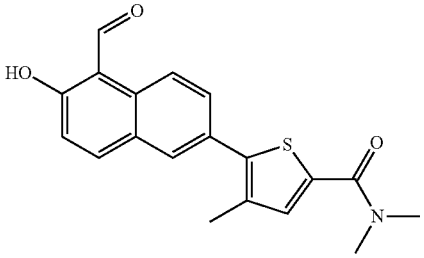 [SMILES: Cc1cc(C(=O)N(C)C)sc1-c1ccc2c(C=O)c(O)ccc2c1] | $^1$H NMR (400 MHz, CDCl$_3$) δ ppm 13.15 (s, 1H), 10.84 (s, 1H), 8.40 (d, J = 9.3 Hz, 1H), 8.01 (d, J = 9.0 Hz, 1H), 7.88 (d, J = 1.8 Hz, 1H), 7.74 (dd, J = 8.7, 1.9 Hz, 1H), 7.24 (s, 1H), 7.19 (d, J = 9.0 Hz, 1H), 3.23 (br. s., 6H), 2.37 (s, 3H). |
| 19-19 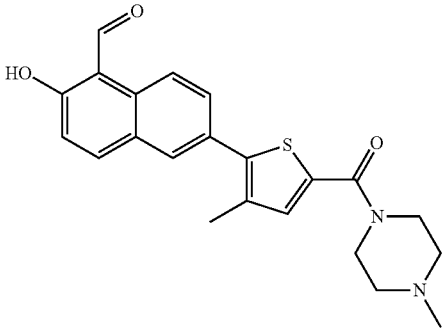 [SMILES: Cc1cc(C(=O)N2CCN(C)CC2)sc1-c1ccc2c(C=O)c(O)ccc2c1] | $^1$H NMR (400 MHz, DMSO-d$_6$) δ ppm 10.81 (s, 1H), 9.03 (d, J = 8.8 Hz, 1H), 8.21 (d, J = 9.0 Hz, 1H), 8.03 (d, J = 1.8 Hz, 1H), 7.75 (dd, J = 8.8, 2.0 Hz, 1H), 7.33 (s, 1H), 7.29 (d, J = 9.0 Hz, 1H), 3.64-3.75 (m, 4H), 2.36-2.43 (m, 4H), 2.35 (s, 3H), 2.23 (s, 3H). |
| 19-20 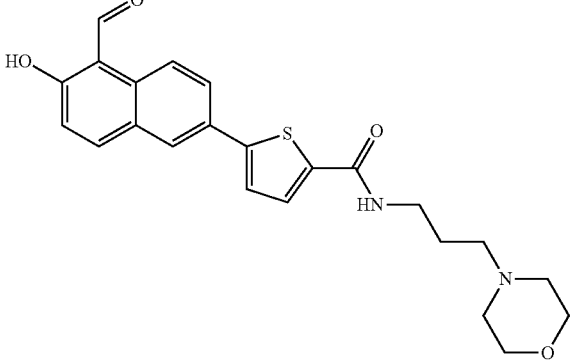 | $^1$H NMR (400 MHz, DMSO-d$_6$) δ ppm 12.10 (br. s., 1H), 10.79 (s, 1H), 9.00 (d, J = 9.0 Hz, 1H), 8.52 (t, J = 5.5 Hz, 1H), 8.22 (d, J = 2.3 Hz, 1H), 8.19 (d, J = 9.0 Hz, 1H), 7.96 (dd, J = 9.0, 2.0 Hz, 1H), 7.76 (d, J = 4.0 Hz, 1H), 7.63 (d, J = 4.0 Hz, 1H), 7.29 (d, J = 9.0 Hz, 1H), 3.54-3.62 (m, 4H), 3.26-3.32 (m, 4H), 2.32-2.47 (m, 4H), 1.64-1.77 (m, 2H). |
| 19-21 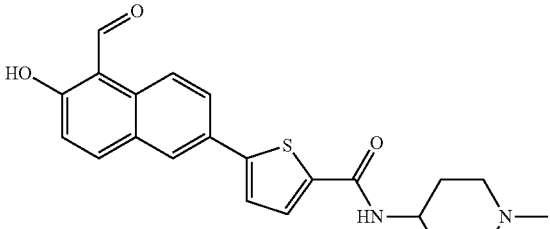 | $^1$H NMR (400 MHz, CDCl$_3$) δ ppm 13.18 (br. s., 1H), 10.81 (s, 1H), 8.37 (d, J = 8.8 Hz, 1H), 7.96-8.05 (m, 2H), 7.86 (dd, J = 8.9, 1.9 Hz, 1H), 7.50 (d, J = 4.0 Hz, 1H), 7.36 (d, J = 3.8 Hz, 1H), 7.19 (d, J = 9.0 Hz, 1H), 5.90 (d, J = 8.0 Hz, 1H), 3.89-4.11 (m, 1H), 2.82-2.95 (m, 2H), 2.36 (s, 3H), 2.18-2.28 (m, 2H), 2.02-2.12 (m, 2H), 1.58-1.74 (m, 2H). |

| No | Stucture | MW | M + 1 |
|---|---|---|---|
| 19-22 | 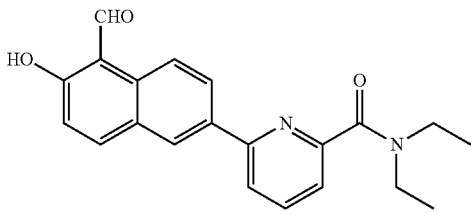 [SMILES: CCN(CC)C(=O)c1cccc(-c2ccc3c(C=O)c(O)ccc3c2)n1] | 348.1 | 349 |

-continued
| No | Structure | MW | M + 1 |
|---|---|---|---|
| 19-23 | 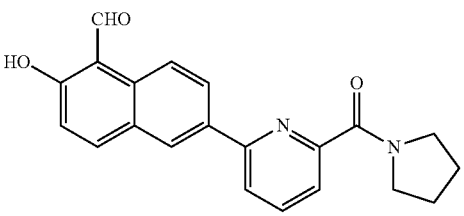 [SMILES: O=Cc1c(O)ccc2cc(-c3cccc(C(=O)N4CCCC4)n3)ccc12] | 346.1 | 347 |
| 19-24 | 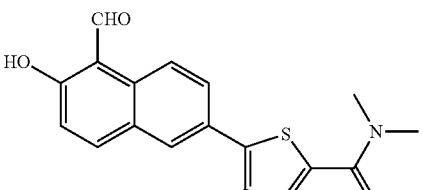 | 339.1 | 340 |
| 19-25 | 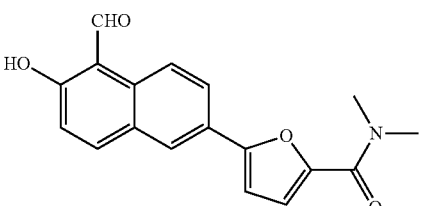 | 309.1 | 310 |
| 19-26 | 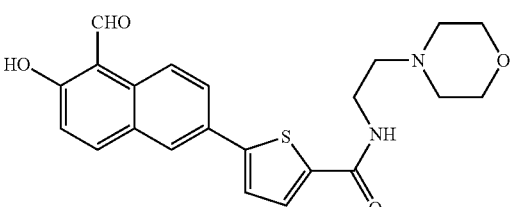 | 410.1 | 411 |
| 19-27 | 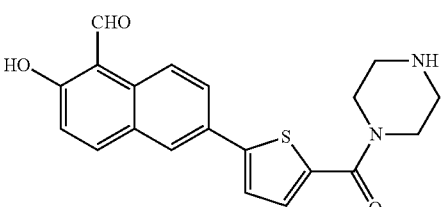 | 366.1 | 367 |
| 19-28 | 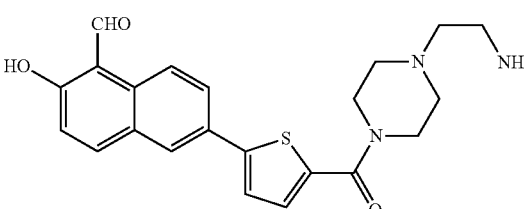 | 409.1 | 410 |
| 19-29 | 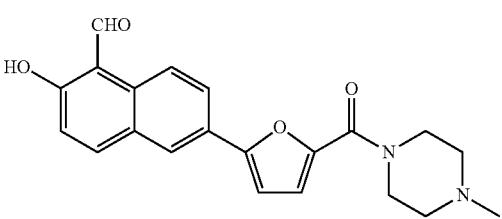 [SMILES: CN1CCN(C(=O)c2ccc(-c3ccc4c(C=O)c(O)ccc4c3)o2)CC1] | 364.1 | 365 |

-continued

| No | Stucture | MW | M + 1 |
|---|---|---|---|
| 19-30 | | 375.2 | 376 |
| 19-31 | | 375.2 | 376 |
| 19-32 | | 375.2 | 376 |
| 19-33 | | 375.2 | 376 |
| 19-34 | | 375.2 | 376 |
| 19-35 | | 378.1 | 379 |

-continued
| No | Structure | MW | M + 1 |
|---|---|---|---|
| 19-36 | 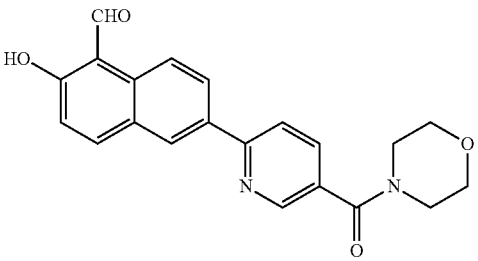 [SMILES: O=Cc1c(O)ccc2cc(-c3ccc(C(=O)N4CCOCC4)cn3)ccc12] | 362.1 | 363 |
| 19-37 | 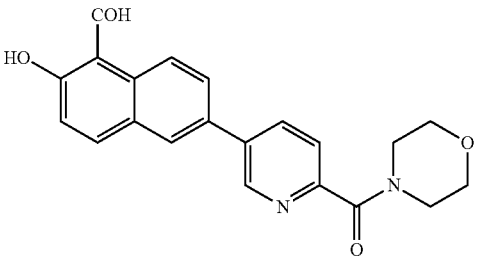 | 362.1 | 363 |
| 19-38 | 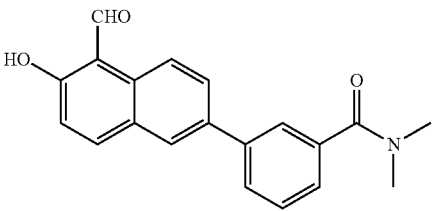 [SMILES: CN(C)C(=O)c1cccc(-c2ccc3c(C=O)c(O)ccc3c2)c1] | 319.1 | 320 |
| 19-39 | 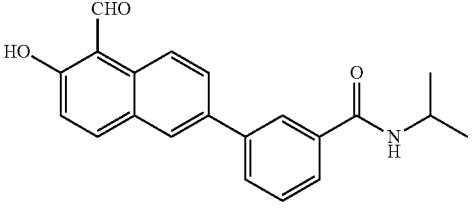 [SMILES: CC(C)NC(=O)c1cccc(-c2ccc3c(C=O)c(O)ccc3c2)c1] | 333.1 | 334 |
| 19-40 | 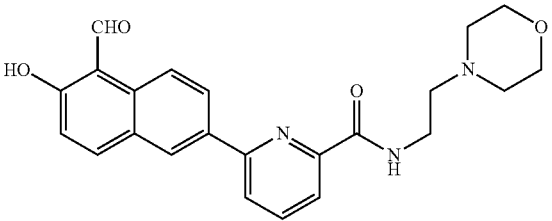 [SMILES: O=Cc1c(O)ccc2cc(-c3cccc(C(=O)NCCN4CCOCC4)n3)ccc12] | 405.2 | 406 |
| 19-41 | 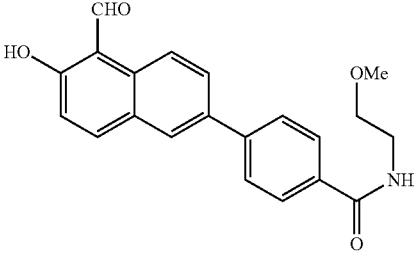 [SMILES: COCCNC(=O)c1ccc(-c2ccc3c(C=O)c(O)ccc3c2)cc1] | 349.1 | 350 |

-continued

| No | Structure | MW | M + 1 |
|---|---|---|---|
| 19-42 | | 364.1 | 365 |
| 19-43 | | 334.1 | 335 |
| 19-44 | | 346.2 | 347 |

Example 20

Synthesis of 2-Hydroxy-6-[2-(4-methyl-piperazin-1-yl)-thiazol-5-yl]-naphthalene-1-carbaldehyde 20-1

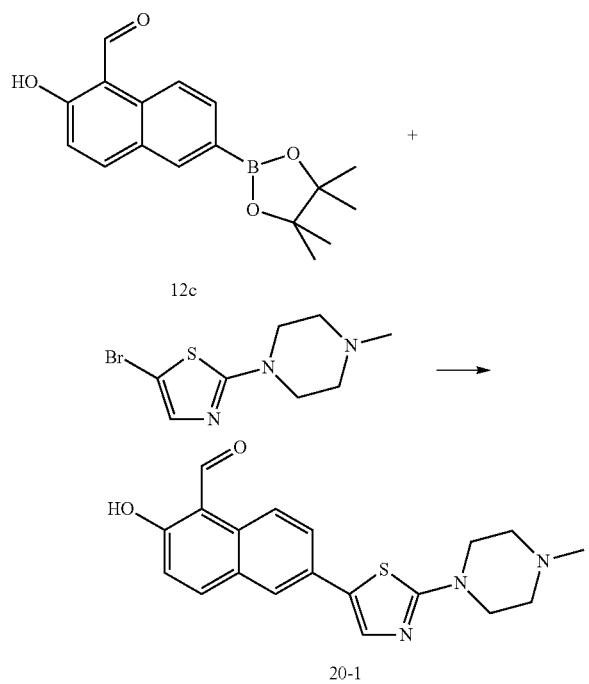

2-Hydroxy-6-[2-(4-methyl-piperazin-1-yl)-thiazol-5-yl]-naphthalene-1-carbaldehyde 20-1

2-Hydroxy-6-(4,4,5,5-tetramethyl-[1,3,2]dioxaborolan-2-yl)-naphthalene-1-carbaldehyde 12c (119 mg, 0.40 mmol), 1-(5-bromo-thiazol-2-yl)-4-methyl-piperazine (126 mg, 0.48 mmol), sodium carbonate (170 mg, 1.60 mmol), and tetrakis(triphenylphosphine)palladium (14 mg, 0.023 mmol) were dissolved in a mixture of 10 mL DMF and 5 mL water. The reaction mixture was stirred at 120° C. under argon for 2 h. The reaction mixture was evaporated to dryness and the solid residue was partitioned between chloroform and water, while the aqueous phase was acidified with acetic acid to neutral pH. The organic phase was separated, and the aqueous layer was extracted once more with chloroform. The combined organic phases were dried over sodium sulfate, filtered and evaporated. The residue was purified by column chromatography eluting with 98:2 chloroform/methanol. The crude product was triturated with diethyl ether, filtered off and air dried, affording 20-1 (85 mg, 0.24 mmol, 60%).

LC/MS ESI: M+H=354, Rt: 2.88 min; $^1$H NMR (400 MHz, CDCl$_3$) δ ppm 13.05 (s, 1H), 10.80 (s, 1H), 8.31 (d, J=9.3 Hz, 1H), 7.94 (d, J=9.0 Hz, 1H), 7.70-7.75 (m, 2H), 7.50 (s, 1H), 7.15 (d, J=9.3 Hz, 1H), 3.52-3.65 (m, 4H), 2.50-2.59 (m, 4H), 2.37 (s, 3H).

The following compounds were made by the above procedure.

| No. | MW | M+H |
|---|---|---|
| 20-1 | 353.4 | 354 |
| 20-2 | 296.3 | 297 |
| 20-3 | 348.4 | 349 |
| 20-4 | 353.4 | 354 |

Example 21

IRE-1α Assay

A fusion protein comprising glutathione S transferase (GST) and human IRE-1α (GST-IRE-1α) obtained from a 500 ml baculovirus-infected insect cell culture can be used to measure IRE-1α activity in vitro.

Five μl of a reaction mixture comprising 1× reaction buffer (5× reaction buffer is 100 mM Hepes pH 7.5, 250 mM KOAc, 2.5 mM MgCl$_2$), 3 mM DTT, and 0.4% polyethylene glycol water is added to each well of 384 well plates. Twenty-five nanoliters of a 1 mM test compound solution are added to test wells. Three μl of a 128 ng/ml IRE-1α preparation are added to each test well and to positive control wells (final concentration 5.82 ng/well). Negative control wells contain only reaction mixture and test compound.

After spinning the plates at 1200 rpm for 30 seconds, 3 μl of an IRE-1α human mini-XBP-1 mRNA stem-loop substrate 5'-CAGUCCGCAGCACUG-3' (SEQ ID NO:1), labeled with the fluorescent dye Cy5 at the 5' end and Black Hole Quencher 2 (BH2) at the 3' end, are added to each well of a control plate. The plates are again spun at 1200 rpm for 30 seconds. Final concentrations for the assay are: 63 nM IRE-1α substrate, 5.82 ng IRE-1α protein, and 2.5 μM test compound.

The plates are covered with lids and incubated for one hour at 30° C. The plates are then transferred to an ACQUEST™ microplate reader. Data is analyzed using data analysis software, and the percent activity of IRE-1α is calculated.

Example 22

Determination of IC$_{50}$ for Inhibition of IRE-1α

IC$_{50}$ for inhibition of IRE-1α of compounds identified in Table 1 was measured as described in Example 21.

Example 23

Kinase Selectivity Assays

Compounds of the invention are assayed for their ability to inhibit 86 different kinases at a concentration of 10 μM. The results of the assays demonstrate that these compounds are selective for IRE-1α.

Example 24

Cell-Based Assays

Human myeloma MM.1s cells are incubated with a compound of the invention for 1.25 hours before stressing the cells withwith 2 mM dithiothreitol (DTT). After an additional 45 minutes (2 hours total) with compound and DTT, the cells are harvested with TRIZOL® (a mono-phasic solution of phenol and guanidine isothiocyanate), and total RNA is prepared as directed by the manufacturer (Invitrogen). Human XBP-1 is amplified by RT-PCR with the following primers, which flank the 26 base unconventional intron excised by IRE-1α:

(forward) (SEQ ID NO: 2)
CCTGGTTGCTGAAGAGGAGG
and (reverse) (SEQ ID NO: 3)
CCATGGGAGATGTTCTGGAG.

In unstressed cells, IRE-1α is inactive and hence, the 26 base intron is left in the XBP-1 mRNA. RT-PCR of unstressed (U) cells then generates the upper band. When cells are stressed (S) with the endoplasmic reticulum (ER) stressing agent DTT, IRE-1α is activated due to accumulating unfolded protein and the resulting RT-PCR product is 26 base pairs shorter. Increasing amounts of the compound block IRE-1α-mediated XBP-1 splicing as demonstrated by a shift from a lower band to an upper band. Compound potency reflects SAR in the in vitro enzyme assay.

Determination of Cellular ED$_{50}$ for IRE-1α Inhibitors

Compounds which pass specificity assays are assayed for cellular EC$_{50}$ using endogenous XBP-1 splicing in myeloma cells. XBP-1 is regulated through the excision of a 26 nucleotide intron from the XBP-1 mRNA by the highly specific endoribonuclease activity of IRE-1α. This splicing event induces a frame shift in the ORF of the C-terminus of XBP-1 leading to the translation of the larger 54 kD active transcription factor rather than the inactive 33 kD form. This splicing event is used to measure IRE-1α activity on XBP-1 mRNA in cells and tissues.

Briefly, compounds are incubated in the presence or absence of an ER stress agent (e.g., DTT), and the ratio of XBP-1u (unspliced) to XBP-1s (spliced) is quantified by RT-PCR. The $ED_{50}$ is determined as the 50% XBP-1s to total XPB-1 levels. Compounds which have $EC_{50}$s equal to or below 10 µM are used in standard apoptosis assays, including Annexin V staining and CASPASE-GLO®.

Proliferation assays using myeloma cell lines (U266, RPMI8226 and MM.1s) are used to determine $ED_{50}$. Compounds are used as single agents and in combination with other chemotherapeutic drugs. IRE-1α inhibitor compounds inhibit the proliferation of RPMI8226 myeloma cells, which have endogenous activation of the pathway and are further induced by the addition of bortezomib. When an IRE-1α inhibitor compound is used in combination with MG-132, increased apoptosis is observed with U266 myeloma cells.

Example 25

Animal Model/Preclinical Validation Studies

The preclinical validation strategy employs a set of animal models representing normal tissues under chemical stress and multiple myeloma xenografts. The normal animal model is employed as a surrogate model where dose-related on-target activity of compounds can be confirmed in tissues sensitive to standard UPR inducing agents such as tunicamycin (Wu et al., Dev Cell. 2007 Sep.; 13(1d):351-64). Normal mouse tissues are not under ER stress, and therefore the XBP-1 mRNA remains as the inactive, unspliced form. Upon induction with tunicamycin, tissues induce active XBP-1 mRNA splicing, and this activity is suppressed by IRE-1α inhibitors. This on-target ER stress animal model is a useful screening and early pharmacokinetic tool.

Antibody production is evaluated in a second surrogate model. However, in cell-based models, IRE-1α inhibitors have been shown to potently inhibit antibody production.

Final efficacy studies are performed in myeloma xenograft models, as described below.

Example 26

RPMI8226 Xenograft Efficacy Model

SCID mice are evaluated for their ability to support implantation of desired tumor cells in support of model development and characterization. Mice are injected intravenously (5) or implanted either subcutaneously (SC) or intraperitoneally (IP). To generate a relevant animal model mimicking human disease, it is desirable that all three approaches are evaluated for improved implantation rates and relevant disease progression, as is well known in the art. SC injections provide an easy way to measure tumor growth and efficacy, and IV and IP injections represent a more physiologically relevant model of human tumor spread. SC injections are given primarily in the flank, while IV injections are administered in the tail vein. Mice are manually restrained for SC and IP injections, and a Broome mouse restrainer is used for IV injections.

Example 27

Evaluation of IRE-1α Inhibitor Compounds in a Xenograft Efficacy Model

SCID mice are implanted with tumor cells (human RPMI8226 myeloma cells) via IP, IV or SC routes based on the results from the xenograft model development studies (above). Mice are treated with compound or mock treated (vehicle) for a period of up to 4-5 weeks. Compound administration can be via IV, IP, PO or SC routes. In some cases, tunicamycin is administered via IP injection in order to stimulate stress in the animal. This stress mimics the stress an animal may undergo during times of tumor growth. The tunicaymycin injection mimics tumor growth during times of stress and permits evaluation of biomarkers which indicate the effectiveness of a compound (such as XBP-1 splicing) by RT-PCR, immunohistochemistry, or Western blots.

Mice are monitored for tumor growth, regression and general health. Tumors are collected and characterized by immunohistochemistry and/or FACS analysis. Tumor growth is measured by calipers, ultrasound, or by abdominal lavage. Biomarkers in the blood or tumor can evaluated (primarily XBP-1 splicing).

In some experiments, blood samples are collected at various time points during the dosing (i.e., day 1 or week 4 etc.) to evaluate the pharmacokinetic profile. The time points of blood collection vary depending on the pharmacokinetic properties of the drug being tested. The volume of blood sample is 100 microliters/per time point, and mice are bled twice after drug administration within a 24 hour period via retro-orbital sinus. If the same mouse is used, blood samples are collected once from each eye during 24 hours.

Tumor cells are cultured and injected IP, IV (tail vein) or SC (flank) in the mouse using a 21G needle in a volume of approx 100 µL. Mice are treated with compounds or vehicle alone as a control by IV, IP, SC or PO routes 5 days per week for up to 4-5 weeks. Blood is collected via retroorbital bleed (100 µA) at 2 time points (different eyes). The endpoint of the study depends on the overall health of the mice: while mice are euthanized at the end of 4-5 weeks in most studies, mice are maintained until day 40 in a few studies if their general health will allow. The reason for maintaining studies for 40 days is to determine if the tested compounds have a long term effect on inhibiting tumor growth. Euthanization of mice in which tumor regression is observed will depend on the experimental design. In screening mode, the experiment will end with tumors in the control/untreated group reach 1.5 cm, are ulcerated or when loss of motility is observed in that group. In follow up experiments, mice in which tumor regression is observed may be maintained longer, until they show signs of tumor growth of ill health.

Therapeutic dosing with bortezomib 0.75 mg/kg IV twice weekly of SCID mice bearing human myeloma RPMI8226 tumor xenografts resulted in suppression of tumor growth. However, after cessation of bortezomib therapy, tumors often recurred and grew into large masses. Therefore, mice will be treated in combination as with both bortezomib (as indicated) and twice daily with 10-60 mg/kg IRE-1α/XBP-1 inhibitors such as compound 17-1 by oral, IP or IV administration. Compounds which reduce the incidence of tumor recurrence are identified.

Example 28

Combination Therapies

The spliced form of XBP-1, as a homodimer and heterodimer with ATF-6, transcriptionally regulates genes involved in adapting to ER stress (Wu et al., Dev Cell. 2007 Sep.; 13(1d):351-64). Many of these downstream targets are major chaperones, co-chaperones and ERAD components of the ER. Chaperones such as GRP78 and GRP94 are stable and long lived proteins with half lives on the order of days (Wu et al., Dev Cell. 2007 Sep.; 13(1d):351-64). Therefore, treatment of cancer with an IRE-1α/XBP-1 inhibitor may require up to 5 to 6 days of treatment in each cycle.

In some embodiments, combination therapy given in cycles such as with proteasome inhibitors involves giving the patient 2 days of pretreatment with IRE-1α/XBP-1 inhibitor and then simultaneously with the chemotherapeutic agent until a pharmacodynamic effect is achieved (typically 24 hours post bortezomib infusion). Bortezomib is typically administered on three week cycles, every 1, 4, 8 and 11 days (of 21). Dosing is 1.3 mg/m$^2$ by IV administration. IRE-1α/XBP-1 inhibitors can be administered 2 day prior and 24 hours post infusion of bortezomib at 10 to 100 mg/kg by the IV or oral route once, twice or three times daily depending on the PK/PD relationship.

A similar protocol can be employed with Hsp90 and or HDAC inhibitors. Alternatively, both agents are administered simultaneously for the duration of each cycle depending on the PK/PD relation of the inhibitor. IRE-1α/XBP-1 inhibitors can be given to breast cancer patients in combination with Tamoxifen (Gomez et al., FASEB J. 2007 Dec.; 21(2):4013-27) or in combination with Sorafinib to various other cancers including kidney carcinoma and hepatocellular carcinoma (Rahmani et al., Mol Cell Biol. 2007 Aug.; 27(15):5499-513).

In general, because many kinase inhibitors often are not selective on their targeted kinase and often affect many additional kinases; they may cause non-specific cellular stress which may activate the UPR. Therefore, combination approaches may be useful using IRE-1α/XBP-1 inhibitors as sensitizing agents.

Example 29

Compound No. 12-4 Inhibits XPB1 Splicing In Vivo in a Model of ER Stress

SCID mice were treated with tunicamycin 1 mg/kg IP. Compound no. 12-4 was administered orally two hours later at one of three doses: 100 mg/kg, 50 mg/kg, or 25 mg/kg (2 hour exposure) in 10% hydroxypropyl-beta-cyclodextrin (HPBCD). The total exposure to tunicamycin was 4 hours, and the total exposure to compound 12-4 was 2 hours. See FIG. 1A.

Livers and kidneys were harvested and total RNA was prepared using Trizol. RT-PCR was performed using murine specific XBP1 primers flanking the 26-nt intron and products were separated on 4% agarose gel. The results are shown in FIG. 1B (liver) and FIG. 1C, in which each lane represents an individual mouse (n=4). A dose-dependent inhibition of XBP-1 slicing is visible for both the liver and kidney.

The invention claimed is:

1. A compound having a structural formula (1c):

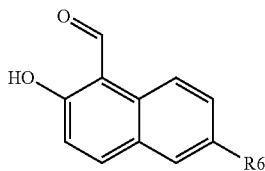
(1c)

or a pharmaceutically acceptable salt thereof,
wherein R6 is:

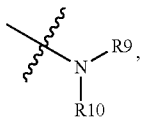
(a)

wherein R9 and R10, together with the nitrogen atom to which they are attached, form a 5-membered or a 6-membered saturated heterocycle containing 1 or 2 N, substituted with C1-C6 alkyl or

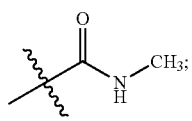 [SMILES: *C(=O)NC]

(b) furyl substituted with

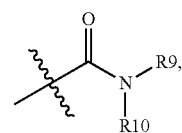

wherein (a) R9 and R10 independently are C1-C6 alkyl or (b) R9 and R10, together with the nitrogen atom to which they are attached, form a 6-membered saturated heterocycle having 2 nitrogen atoms;

(c) pyrimidinyl substituted with

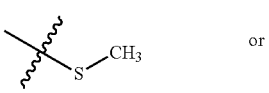
(a)

or

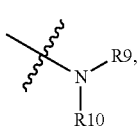
(b)

in which R9 and R10, together with the nitrogen atom to which they are attached, form a 6-membered saturated heterocycle having 2 nitrogen atoms;

(d) thiazolyl substituted with C1-C6 alkyl or

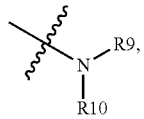

wherein (a) R9 and R10 independently are hydrogen or C1-C6 alkoxyl C1-C6 alkyl or (b) R9 and R10, together with the nitrogen atom to which they are attached, form a 5-membered saturated ring containing one nitrogen atom or a 6-membered saturated heterocycle containing 1 or 2 heteroatoms selected from nitrogen and oxygen;

(e) oxazolyl substituted with

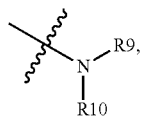

wherein (a) R9 and R10 independently are hydrogen or C1-C6 alkyl or (b) R9 and R10, together with the nitrogen atom to which they are attached, form a 6-membered heterocycle containing two nitrogen atoms;

(f) triazolyl substituted with C1-C6 alkoxyl C1-C6 alkyl or

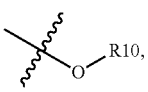

wherein R10 is C1-C6 alkyl; or

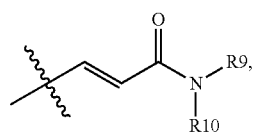
(g)

wherein (a) R9 and R10 independently are C1-C6 alkyl or (b) R9 and R10, together with the nitrogen atom to which they are attached, form a 6-membered saturated heterocycle containing the nitrogen atom and one oxygen atom.

2. A pharmaceutical composition comprising a compound of claim 1 or pharmaceutically acceptable salt of the compound; and a pharmaceutically acceptable vehicle.

3. A method of inhibiting IRE-1α, comprising contacting IRE-1α with a compound of claim 1 or pharmaceutically acceptable salt of the compound thereby inhibiting the IRE-1α.

4. A method of treating a disease associated with the unfolded protein response, comprising administering to a patient in need thereof an effective amount of a compound of claim 1 or pharmaceutically acceptable salt of the compound.

5. A compound having structural formula (1a):

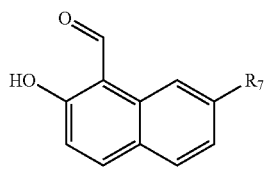
(1a)

or a pharmaceutically acceptable salt thereof, wherein R7 is phenyl substituted with

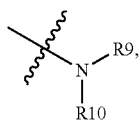

wherein R9 and R10, together with the nitrogen atom to which they are attached, form a 6-membered saturated heterocycle containing 2 nitrogen atoms, substituted with C1-C6 alkyl.

6. A pharmaceutical composition comprising a compound of claim 5 or a pharmaceutically acceptable salt of the compound; and a pharmaceutically acceptable vehicle.

7. A method of inhibiting IRE-1α, comprising contacting IRE-1α with a compound of claim 5 or pharmaceutically acceptable salt of the compound thereby inhibiting the IRE-1α.

8. A method of treating a disease associated with the unfolded protein response, comprising administering to a patient in need thereof an effective amount of a compound of claim 5 or pharmaceutically acceptable salt of the compound.

9. The compound of claim 5, wherein the C1-C6 alkyl is selected from the group consisting of C1-C5 alkyl, C1-C4 alkyl, and C1-C3 alkyl.

10. The compound of claim 5, wherein the C1-C6 alkyl is selected from the group consisting of isopropyl, sec-butyl, tert-butyl, n-butyl, and 2-butyl.

11. The compound of claim 1, wherein R6 is

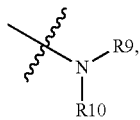

wherein R9 and R10, together with the nitrogen atom to which they are attached, form a 5-membered or a 6-membered saturated heterocycle containing 1 or 2 N, substituted with C1-C6 alkyl or

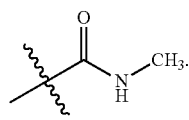

12. The compound of claim 1, wherein R6 is furyl substituted with

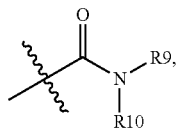

wherein (a) R9 and R10 independently are C1-C6 alkyl or (b) R9 and R10, together with the nitrogen atom to which they are attached, form a 6-membered saturated heterocycle having 2 nitrogen atoms.

13. The compound of claim 1, wherein R6 is pyrimidinyl substituted with

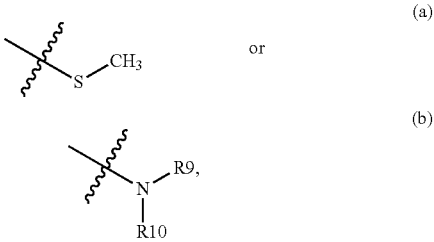

in which R9 and R10, together with the nitrogen atom to which they are attached, form a 6-membered saturated heterocycle having 2 nitrogen atoms.

14. The compound of claim 1, wherein R6 is thiazolyl substituted with C1-C6 alkyl or

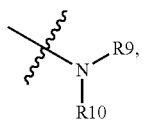

wherein (a) R9 and R10 independently are hydrogen or C1-C6 alkoxyl C1-C6 alkyl or (b) R9 and R10, together with the nitrogen atom to which they are attached, form a 5-membered saturated ring containing one nitrogen atom or a 6-membered saturated heterocycle containing 1 or 2 heteroatoms selected from nitrogen and oxygen.

15. The compound of claim 1, wherein R6 is oxazolyl substituted with

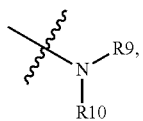

wherein (a) R9 and R10 independently are hydrogen or C1-C6 alkyl or (b) R9 and R10, together with the nitrogen atom to which they are attached, form a 6-membered heterocycle containing two nitrogen atoms.

16. The compound of claim 1, wherein R6 is triazolyl substituted with C1-C6 alkoxyl C1-C6 alkyl or

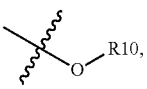

wherein R10 is C1-C6 alkyl.

17. The compound of claim 1, wherein R6 is
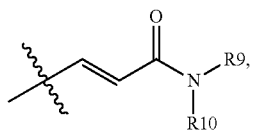
wherein (a) R9 and R10 independently are C1-C6 alkyl or (b) R9 and R10, together with the nitrogen atom to which they are attached, form a 6-membered saturated heterocycle containing the nitrogen atom and one oxygen atom.
* * * * *

SEQUENCE LISTING

```
<160> NUMBER OF SEQ ID NOS: 3

<210> SEQ ID NO 1
<211> LENGTH: 15
<212> TYPE: DNA
<213> ORGANISM: Artificial Sequence
<220> FEATURE:
<223> OTHER INFORMATION: mini-XBP-1 mRNA stem-loop substrate

<400> SEQUENCE: 1
caguccgcag gacug                                                        15

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
cctggttgct gaagaggagg                                                   20

<210> SEQ ID NO 3
<211> LENGTH: 21
<212> TYPE: DNA
<213> ORGANISM: Artificial Sequence
<220> FEATURE:
<223> OTHER INFORMATION: primer

<400> SEQUENCE: 3
ccatggggag atgttctgga g                                                 21
```